US 6,638,927 B2

(12) United States Patent
Renhowe et al.

(10) Patent No.: US 6,638,927 B2
(45) Date of Patent: Oct. 28, 2003

(54) GUANIDINOBENZAMIDES

(75) Inventors: Paul A. Renhowe, Danville, CA (US);
Daniel Chu, Santa Clara, CA (US);
Rustum S. Boyce, San Francisco, CA (US); Zhi-Jie Ni, Fremont, CA (US);
David Duhl, Oakland, CA (US); Effie Tozzo, Newton, MA (US); Kirk Johnson, Moraga, CA (US); David C. Myles, Kensington, CA (US)

(73) Assignee: Chiron Corporation, Emeryville, CA (US)

( * ) Notice: Subject to any disclaimer, the term of this patent is extended or adjusted under 35 U.S.C. 154(b) by 59 days.

(21) Appl. No.: 09/945,384

(22) Filed: Aug. 31, 2001

(65) Prior Publication Data

US 2002/0137939 A1 Sep. 26, 2002

Related U.S. Application Data

(60) Provisional application No. 60/230,565, filed on Aug. 31, 2000, and provisional application No. 60/245,579, filed on Nov. 6, 2000.

(51) Int. Cl.$^7$ .................. C07D 295/20; C07D 213/40; A61K 31/155; A61K 31/495; A61P 3/00
(52) U.S. Cl. .................. 514/218; 544/400; 544/374; 514/252.12; 514/254.1; 540/575; 564/163; 564/164
(58) Field of Search .................. 544/400, 374; 514/252.12, 218, 254.1; 540/575; 564/163, 164

(56) References Cited

U.S. PATENT DOCUMENTS

| | | | |
|---|---|---|---|
| 4,732,916 A | 3/1988 | Satoh et al. .................. 514/620 |
| 4,874,864 A | 10/1989 | Schnur et al. .................. 546/153 |
| 4,921,939 A | * 5/1990 | Nofre et al. .................. 558/414 |
| 4,948,891 A | 8/1990 | Schnur et al. .................. 548/329 |
| 4,948,901 A | 8/1990 | Schnur et al. .................. 548/329 |
| 5,086,057 A | 2/1992 | Sasagawa .................. 514/267 |
| 5,124,328 A | 6/1992 | Fisher et al. .................. 514/235.8 |
| 5,352,704 A | 10/1994 | Okuyama et al. .................. 514/619 |
| 5,362,902 A | 11/1994 | Barnish et al. .................. 560/13 |
| 5,547,966 A | 8/1996 | Atwal et al. .................. 514/352 |
| 5,637,439 A | 6/1997 | Kaneko et al. .................. 430/264 |
| 5,750,573 A | 5/1998 | Bianchi et al. .................. 514/597 |
| 5,885,985 A | 3/1999 | Macdonald et al. .................. 514/217 |
| 5,889,025 A | 3/1999 | Lohray et al. .................. 514/326 |
| 5,952,381 A | 9/1999 | Chen et al. .................. 514/565 |
| 5,962,530 A | 10/1999 | Engel et al. .................. 514/595 |
| 6,020,349 A | 2/2000 | Ankerson et al. .................. 514/341 |
| 6,030,985 A | 2/2000 | Gentile et al. .................. 514/307 |
| 6,127,343 A | 10/2000 | Ankersen et al. .................. 514/20 |

FOREIGN PATENT DOCUMENTS

| | | |
|---|---|---|
| EP | 0343894 | 11/1989 |
| WO | WO 96/24580 | 8/1996 |
| WO | WO 97/19911 | 6/1997 |
| WO | WO 97/41119 | 11/1997 |
| WO | WO 98/07420 | 2/1998 |
| WO | WO 99/64002 | 12/1999 |
| WO | WO 00/17191 | 3/2000 |
| WO | WO/0074679 | 12/2000 |
| WO | WO 01/10842 | 2/2001 |
| WO | WO 01/55106 | 8/2001 |
| WO | WO 01/55107 | 8/2001 |
| WO | WO 01/55109 | 8/2001 |
| WO | WO 01/70337 | 9/2001 |
| WO | WO 01/70708 | 9/2001 |

OTHER PUBLICATIONS

CAS printout for Hirata et al., Chem Abstract 127: 142754.*
CAS Printout for Julia et al., Chem Abstract 69: 10170.*
Fisher et al. Melanocortin–4 receptor: a novel signalling pathway involved in body wieght regulation, Int. J. Obes. Relat. Metab. 1999, Suppl 1:54–8.*
Julia, M., et al., "Amidines and guanidines related to congocidine. III. Urea and triazene diamidines," *Bull. Soc. Chim. Fr.*, No. 1, pp. 376–382, 1968, published by Masson Editeur, Paris, France.

* cited by examiner

Primary Examiner—Mukund J. Shah
Assistant Examiner—Hong Liu
(74) Attorney, Agent, or Firm—Foley & Lardner

(57) ABSTRACT

Compounds of formula IA and IB are new

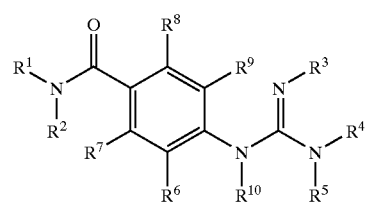

IA

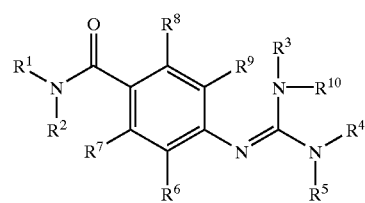

IB where the variables $R^1$ through $R^{10}$ have the values set forth herein. Such compounds have use in treating diseases such as obesity and type II diabetes, and may be provided as pharmaceutical formulations in conjunction with a pharmaceutically acceptable carrier.

14 Claims, 6 Drawing Sheets

GUANIDINOBENZAMIDES

CROSS-REFERENCES TO RELATED APPLICATIONS

This application claims priority to U.S. Provisional Application No. 60/230,565 filed Aug. 31, 2000, and U.S. Provisional Application No. 60/245,579 filed Nov. 6, 2000, the entire disclosures of which are incorporated herein by reference and for all purposes.

FIELD OF THE INVENTION

This invention relates to melanocortin-4 receptor (MC4-R) agonists and methods of their preparation. The invention also relates to methods of treating melanocortin-4 receptor-mediated diseases, such as obesity or diabetes, by activating the melanocortin-4 receptor with compounds provided herein.

BACKGROUND OF THE INVENTION

Melanocortins are peptide products resulting from post-translational processing of pro-opiomelanocortin and are known to have a broad array of physiological activities. The natural melanocortins include the different types of melanocyte stimulating hormone (α-MSH, β-MSH, γ-MSH) and ACTH. Of these, α-MSH and ACTH are considered to be the main endogenous melanocortins.

The melanocortins mediate their effects through melanocortin receptors (MC-Rs), a subfamily of G-protein coupled receptors. There are at least five different receptor subtypes (MC1-R to MC5-R). MC1-R mediates pigmentation of the hair and skin. MC2-R mediates the effects of ACTH on steroidogenesis in the adrenal gland. MC3-R and MC4-R are predominantly expressed in the brain. MC5-R is considered to have a role in the exocrine gland system.

The melanocortin-4 receptor (MC4-R) is a seven-transmembrane receptor. MC4-R may participate in modulating the flow of visual and sensory information, coordinate aspects of somatomotor control, and/or participate in the modulation of autonomic outflow to the heart. K. G. Mountjoy et al., *Science*, 257:1248–125 (1992). Significantly, inactivation of this receptor by gene targeting has resulted in mice that develop a maturity onset obesity syndrome associated with hyperphagia, hyperinsulinemia, and hyperglycemia. D. Husznar et al., *Cell*, 88(1): 131–41 (1997). MC4-R has also been implicated in other disease states including erectile disorders, cardiovascular disorders, neuronal injuries or disorders, inflammation, fever, cognitive disorders, and sexual behavior disorders. M. E. Hadley and C. Haskell-Luevano, *The proopiomelanocortin system, Ann. N. Y. Acad. Sci.*, 885:1 (1999).

Furthermore, observations in connection with endogenous MCx-R antagonists indicate that MC4-R is implicated in endogenous energy regulation. For example, an agouti protein is normally expressed in the skin and is an antagonist of the cutaneous MC receptor involved in pigmentation, MC1-R. M. M. Ollmann et al., *Science*, 278:135–138 (1997). However, overexpression of agouti protein in mice leads to a yellow coat color due to antagonism of MC1-R and increased food intake and body weight due to antagonism of MC4-R. L. L. Kiefer et al., *Biochemistry*, 36: 2084–2090 (1997); D. S. Lu et al., *Nature*, 371:799–802 (1994). Agouti related protein (AGRP), an agouti protein homologue, antagonizes MC4-R but not MC1-R. T. M. Fong et al., *Biochem. Biophys. Res. Commun.* 237:629–631 (1997). Administration of AGRP in mice increases food intake and causes obesity but does not alter pigmentation. M. Rossi et al., *Endocrinology*, 139:4428–4431 (1998). Together, this research indicates that MC4-R participates in energy regulation, and therefore, identifies this receptor as a target for a rational drug design for the treatment of obesity.

In connection with MC4-R and its uncovered role in the etiology of obesity and food intake, the prior art includes reports of compounds and compositions that act as agonists or antagonists of MC4-R. As examples, U.S. Pat. No. 6,060,589 describes polypeptides that are capable of modulating signaling activity of melanocortin receptors. Also, U.S. Pat. Nos. 6,054,556 and 5,731,408 describe families of agonists and antagonists for MC4-R receptors that are lactam heptapeptides having a cyclic structure. WO 01/10842 discloses MC4-R binding compounds having a multitude of structures and methods of using such compounds to treat MC4-R associated disorders. Some of the compounds described include amidino- and guanidino-containing arenes and heteroarenes.

Other guanidine-containing compounds having a variety of biological activities are also known in the prior art. For example, U.S. Pat. No. 4,732,916 issued to Satoh et al. discloses guanidine compounds useful as antiulcer agents; U.S. Pat. Nos. 4,874,864, 4,949,891, and 4,948,901 issued to Schnur et al. and EP 0343 894 disclose guanidino compounds useful as protease inhibitors and as anti-plasmin and anti-thrombin agents; and U.S. Pat. No. 5,352,704 issued to Okuyama et al. discloses a guanidino compound useful as an antiviral agent. Guanidine-containing compounds are also disclosed in other references. For example, U.S. Pat. No. 6,030,985 issued to Gentile et al. discloses guanidine compounds useful for treating and preventing conditions in which inhibition of nitric oxide synthetase is beneficial such as stroke, schizophrenia, anxiety, and pain. U.S. Pat. No. 5,952,381 issued to Chen et al. discloses certain guanidine compounds for use in selectively inhibiting or antagonizing $\alpha_v\beta_3$ integrins.

Various 5-, 6-, and 7-membered fully saturated 1-azacarbocyclic-2-ylidene derivatives of guanidine are disclosed as having anti-secretory and hypoglycemic activities by U.S. Pat. No. 4,211,867 issued to Rasmussen. Such compounds are also taught as useful for the treatment of cardiovascular disease. Other guanidine derivatives are disclosed by U.S. Pat. No. 5,885,985 issued to Macdonald et al. as useful in therapy to treat inflammation.

Nevertheless, there remains a need for potent and specific agonists of MC4-R that are low molecular weight non-peptide small molecules. Methods of treating a melanocortin-4 receptor mediated disease, such as obesity, with such non-peptide drugs, are also particularly desirable.

SUMMARY OF THE INVENTION

The instant invention provides potent and specific agonists of MC4-R that are low molecular weight non-peptide small molecules. Thus, there has been provided, in accordance with one aspect of the invention, a compound of either formula IA or IB:

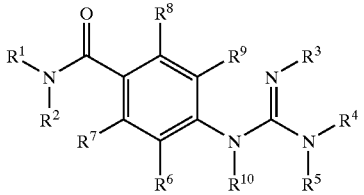

IA

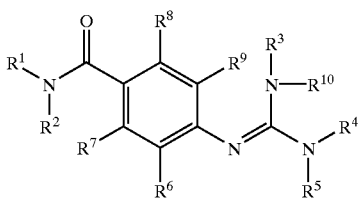

IB wherein
- $R^1$ is selected from the group consisting of H, and substituted and unsubstituted arylalkyl, heteroarylalkyl, aryl, heteroaryl, heterocyclyl, cycloalkyl, heterocyclylalkyl, cycloalkylalkyl, alkenyl, alkynyl, and alkyl groups;
- $R^2$ is selected from the group consisting of substituted and unsubstituted arylalkyl, heteroarylalkyl, aryl, heteroaryl, heterocyclyl, cycloalkyl, heterocyclylalkyl, cycloalkylalkyl, alkenyl, alkynyl, and alkyl groups;
- $R^3$ is selected from the group consisting of substituted and unsubstituted alkyl, alkenyl, alkynyl, cycloalkyl, heteroaryl, heterocyclyl, heterocyclylalkyl, arylalkyl, heteroarylalkyl, and cycloalkylalkyl groups;
- $R^4$ is selected from the group consisting of H, and substituted and unsubstituted alkyl, alkenyl, alkynyl, cycloalkyl, aryl, heteroaryl, heterocyclyl, arylalkyl, heteroarylalkyl, and cycloalkylalkyl groups;
- $R^5$ is selected from the group consisting of substituted and unsubstituted alkyl, alkenyl, alkynyl, cycloalkyl, aryl, heteroaryl, heterocyclyl, arylalkyl, heteroarylalkyl, and cycloalkylalkyl groups; or
- $R^4$ and $R^5$, together with the nitrogen to which they are bound, form a substituted or unsubstituted heterocyclyl or heteroaryl group;
- $R^6$, $R^7$, $R^8$, and $R^9$ may be the same or different, and are each independently selected from the group consisting of H, Cl, I, F, Br, OH, $NH_2$, CN, $NO_2$, and substituted and unsubstituted alkoxy, amino, alkyl, alkenyl, alkynyl, alkylamino, dialkylamino, cycloalkyl, heterocyclylamino, heteroarylamino, aminocarbonyl, alkylaminocarbonyl, dialkylaminocarbonyl, cycloalkylaminocarbonyl, arylaminocarbonyl, heterocyclylaminocarbonyl, and heteroarylaminocarbonyl groups; and
- $R^{10}$ is selected from the group consisting of H, and substituted and unsubstituted alkyl, alkenyl, alkynyl, cycloalkylalkyl, aryl, and arylalkyl groups.

Compounds provided by the invention further include prodrugs of the compounds of either formula IA or IB, pharmaceutically acceptable salts thereof, stereoisomers thereof, tautomers thereof, hydrates thereof, hydrides thereof, or solvates thereof.

In one embodiment, $R^2$ is selected from the group consisting of substituted and unsubstituted arylalkyl, alkenyl, heteroarylalkyl, and heterocyclylalkyl groups.

In another embodiment, $R^3$ is selected from the group consisting of substituted and unsubstituted cycloalkyl, alkenyl, alkyl, and aryl groups.

In another embodiment, $R^4$ and $R^5$ may be the same or different and are each independently selected from the group consisting of substituted and unsubstituted alkyl, arylalkyl, and heteroarylalkyl groups.

In another embodiment, $R^4$ and $R^5$, together with the nitrogen to which they are bound, form a substituted or unsubstituted heterocyclyl group.

In another embodiment, $R^4$ and $R^5$, together with the nitrogen to which they are bound, form a substituted or unsubstituted saturated heterocyclyl group comprising at least one heteroatom selected from the group consisting of O, S, and N in addition to the N atom to which $R^4$ and $R^5$ are bound.

There has also been provided, in accordance with another aspect of the invention, a compound of either formula IIA or IIB:

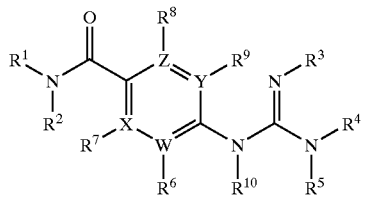

IIA

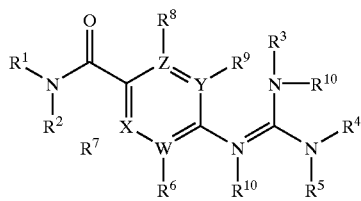

IIB wherein
- at least one of W, X, Y, or Z is a nitrogen atom, forming, e.g., a pyridyl group;
- $R^1$ is selected from the group consisting of H, and substituted and unsubstituted arylalkyl, heteroarylalkyl, aryl, heteroaryl, heterocyclyl, cycloalkyl, heterocyclylalkyl, cycloalkylalkyl, alkenyl, alkynyl, and alkyl groups;
- $R^2$ is selected from the group consisting of substituted and unsubstituted arylalkyl, heteroarylalkyl, aryl, heteroaryl, heterocyclyl, cycloalkyl, heterocyclylalkyl, cycloalkylalkyl, alkenyl, alkynyl, and alkyl groups;
- $R^3$ is selected from the group consisting of H and substituted and unsubstituted alkyl, alkenyl, alkynyl, cycloalkyl, heteroaryl, heterocyclyl, heterocyclylalkyl, arylalkyl, heteroarylalkyl, and cycloalkylalkyl groups;
- $R^4$ is selected from the group consisting of H, and substituted and unsubstituted alkyl, alkenyl, alkynyl, cycloalkyl, aryl, heteroaryl, heterocyclyl, arylalkyl, heteroarylalkyl, and cycloalkylalkyl groups;
- $R^5$ is selected from the group consisting of substituted and unsubstituted alkyl, alkenyl, alkynyl, cycloalkyl, aryl, heteroaryl, heterocyclyl, arylalkyl, heteroarylalkyl, and cycloalkylalkyl groups; or
- $R^4$ and $R^5$, together with the nitrogen to which they are bound, form a substituted or unsubstituted heterocyclyl or heteroaryl group;
- $R^6$, $R^7$, $R^8$, and $R^9$ may be the same or different, and are each independently selected from the group consisting of H, Cl, I, F, Br, OH, $NH_2$, CN, $NO_2$, and substituted and unsubstituted alkoxy, amino, alkyl, alkenyl, alkynyl, alkylamino, dialkylamino, cycloalkyl, heterocyclylamino, heteroarylamino, aminocarbonyl, alkylaminocarbonyl, dialkylaminocarbonyl, cycloalkylaminocarbonyl, arylaminocarbonyl, heterocyclylaminocarbonyl, and heteroarylaminocarbonyl groups;

wherein $R^6$ may be absent if W is a nitrogen atom;
wherein $R^7$ may be absent if X is a nitrogen atom;
wherein $R^8$ may be absent if Z is a nitrogen atom;
wherein $R^9$ may be absent if Y is a nitrogen atom; and
$R^{10}$ is selected from the group consisting of H, and substituted and unsubstituted alkyl, alkenyl, alkynyl, cycloalkylalkyl, aryl, and arylalkyl groups.

Compounds of either formula IIA or IIB provided by the invention further include prodrugs thereof, pharmaceutically acceptable salts thereof, stereoisomers thereof, tautomers thereof, hydrates thereof, hydrides thereof, or solvates thereof.

In another embodiment, $R^2$ is selected from the group consisting of substituted and unsubstituted arylalkyl, alkenyl, heteroarylalkyl, and heterocyclylalkyl groups.

In another embodiment, $R^3$ is selected from the group consisting of substituted and unsubstituted cycloalkyl, alkenyl, alkyl, and aryl groups.

In another embodiment, $R^4$ and $R^5$ may be the same or different and are each independently selected from the group consisting of substituted and unsubstituted alkyl, arylalkyl, and heteroarylalkyl groups.

In another embodiment, $R^4$ and $R^5$, together with the nitrogen to which they are bound, form a substituted or unsubstituted heterocyclyl group.

In another embodiment, $R^4$ and $R^5$, together with the nitrogen to which they are bound, form a substituted or unsubstituted saturated heterocyclyl group comprising at least one heteroatom selected from the group consisting of O, S, and N in addition to the N atom to which $R^4$ and $R^5$ are bound.

There has also been provided, in accordance with another aspect of the invention, a composition comprising a compound according to the instant invention and a pharmaceutically acceptable carrier.

There has also been provided, in accordance with another aspect of the invention, a method of treating an MC4-R mediated disease, comprising administering to a subject in need thereof, a compound or composition of the instant invention.

In one embodiment, a disease to be treated by those methods of the instant invention is obesity or type II diabetes.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENT

Figure 1:
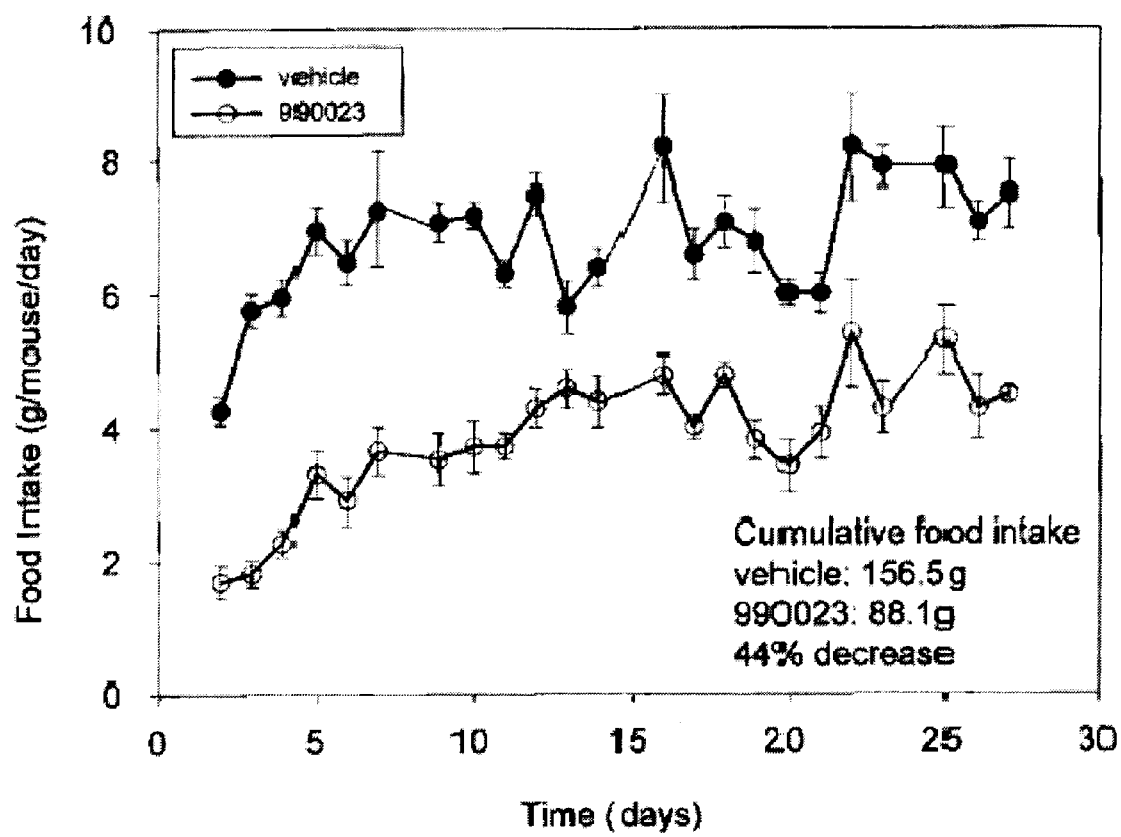
FIG. 1 is a graph showing the reduction in food intake in obese mice treated intraperitoneally ("IP") with 4-[(N-cyclohexyl-3,5-dimethyl-piperazine-1-carboximidoyl)-amino]-N-[2-(2,4-dichlorophenyl)-ethyl]-benzamide for 4 weeks.

The instant invention relates to novel classes of small molecule melanocortin-4 receptor (MC4-R) agonists. These compounds can be formulated into compositions and are useful in activating MC4-R, or in the treatment of MC4-R-mediated diseases, such as obesity, type II diabetes, erectile dysfunction, polycystic ovary disease, complications resulting from or associated with obesity and diabetes, and Syndrome X.

The following definitions are used throughout this specification.

Alkyl groups include straight chain and branched alkyl groups having 1 to about 8 carbon atoms. Examples of straight chain alkyl groups include methyl, ethyl, propyl, butyl, pentyl, hexyl, heptyl, and octyl groups. Examples of branched alkyl groups, include, but not limited to, isopropyl, sec-butyl, t-butyl, and isopentyl groups. Representative substituted alkyl groups may be substituted one or more times with, for example, amino, thio, alkoxy, or halo groups such as F, Cl, Br, and I groups.

Cycloalkyl groups are cyclic alkyl groups such as, but not limited to, cyclopropyl, cyclobutyl, cyclopentyl, cyclohexyl, cycloheptyl, and cyclooctyl groups. Cycloalkyl groups also includes rings that are substituted with straight or branched chain alkyl groups as defined above, and further include cycloalkyl groups that are substituted with other rings including fused rings such as, but not limited to, decalinyl, tetrahydronaphthyl, and indanyl. Cycloalkyl groups also include polycyclic cycloalkyl groups such as, but not limited to, norbornyl, adamantyl, bornyl, camphenlyl, isocamphenyl, and carenyl groups. Representative substituted cycloalkyl groups may be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which may be substituted with, for example, alkyl, alkoxy, amino, thio, or halo groups.

Alkenyl groups are straight chain, branched or cyclic lower alkyl groups having 2 to about 8 carbon atoms, and further including at least one double bond, as exemplified, for instance, by vinyl, propenyl, 2-butenyl, 3-butenyl, isobutenyl, cyclohexenyl, cyclopentenyl, cyclohexadienyl, butadienyl, pentadienyl, and hexadienyl groups among others.

Alkynyl groups are straight chain or branched lower alkyl groups having 2 to about 8 carbon atoms, and further including at least one triple bond, as exemplified by groups, including, but not limited to, ethynyl, propynyl, and butynyl groups.

Aryl groups are cyclic aromatic hydrocarbons that do not contain heteroatoms. Thus aryl groups include, but are not limited to, phenyl, azulene, heptalene, biphenylene, indacene, fluorene, phenanthrene, triphenylene, pyrene, naphthacene, chrysene, biphenyl, anthracenyl, and naphthenyl groups. Although the phrase "aryl groups" includes groups containing fused rings, such as fused aromatic-aliphatic ring systems, it does not include aryl groups that have other groups, such as alkyl or halo groups, bonded to one of the ring members. Rather, groups such as tolyl are referred to as substituted aryl groups. The phrase "aryl groups" includes groups bonded to one or more carbon atom(s), and/or nitrogen atom(s), in the compounds of formulas I and II. Representative substituted aryl groups may be mono-substituted or substituted more than once, such as, but not limited to, 2-, 3-, 4-, 5-, or 6-substituted phenyl or benzyl groups, which may be substituted with groups including, but not limited to, amino, alkoxy, alkyl, or halo.

Cycloalkylalkyl groups are alkyl groups as defined above in which a hydrogen or carbon bond of an alkyl group is replaced with a bond to a cycloalkyl group as defined above.

Arylalkyl groups are alkyl groups as defined above in which a hydrogen or carbon bond of an alkyl group is replaced with a bond to an aryl group as defined above.

Heterocyclyl groups are nonaromatic ring compounds containing 3 or more ring members, of which, one or more is a heteroatom such as, but not limited to, N, O, and S. The phrase "heterocyclyl group" includes fused ring species including those comprising fused aromatic and nonaromatic groups. The phrase also includes polycyclic ring systems containing a heteroatom such as, but not limited to quinuclidyl. However, the phrase does not include heterocyclyl groups that have other groups, such as alkyl or halo groups, bonded to one of the ring members. Rather, these are referred to as "substituted heterocyclyl groups". Heterocyclyl groups include, but are not limited to, piperazino, morpholino, thiomorpholino, pyrrolidino, piperidino and homopiperazino groups. Representative substituted heterocyclyl groups may be mono-substituted or substituted more than once, such as, but not limited to morpholino or piperazino groups, which are 2-, 3-, 4-, 5-, or 6-substituted, or disubstituted with groups including, but not limited to, amino, alkoxy, alkyl, or halo.

Heteroaryl groups are aromatic ring compounds containing 3 or more ring members, of which, one or more is a heteroatom such as, but not limited to, N, O, and S. Heteroaryl groups include, but are not limited to, groups such as furan, thiophene, pyrrole, isopyrrole, diazole, imidazole, isoimidazole, triazole, dithiole, oxathiole, isoxazole, oxazole, thiazole, isothiazole, oxadiazole, oxatriazole, dioxazole, oxathiazole, pyran, dioxin, pyridine, pyrimidine, pyridazine, pyrazine, triazine, oxazine, isoxazine, oxathiazine, azepin, oxepin, thiepin, diazepine, benzofuran, and isobenzofuran. Although the phrase "heteroaryl groups" includes fused ring compounds, the phrase does not include heteroaryl groups that have other groups bonded to one of the ring members, such as alkyl groups. Rather, heteroaryl groups with such substitution are referred to as "substituted heteroaryl groups". Representative substituted heteroaryl groups may be substituted one or more times with groups including, but not limited to, amino, alkoxy, alkyl, or halo.

Heterocyclylalkyl groups are alkyl groups as defined above in which a hydrogen or carbon bond of an alkyl group is replaced with a bond to a heterocyclyl group as defined above.

Heteroarylalkyl groups are alkyl groups as defined above in which a hydrogen or carbon bond of an alkyl group is replaced with a bond to a heteroaryl group as defined above.

Aminocarbonyl groups are groups of the formula RR'NC(O)—, wherein R or R' may be the same or different, and each is independently selected from H, or substituted or unsubstituted alkyl, cycloalkyl, aryl, heterocyclyl or heteroaryl groups, as defined above.

In general, "substituted" refers to a group as defined above in which one or more bonds to a hydrogen atom contained therein are replaced by a bond to non-hydrogen or non-carbon atoms such as, but not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, amides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups and also substituted cycloalkyl groups also include groups in which one or more bonds to a carbon(s) or hydrogen(s) atom is replaced by a bond to a heteroatom such as oxygen in carbonyl, carboxyl, and ester groups; nitrogen in groups such as imines, oximes, hydrazones, and nitriles.

Substituted cycloalkyl, substituted aryl, substituted heterocyclyl and substituted heteroaryl also include rings and fused ring systems in which a bond to a hydrogen atom is replaced with a bond to a carbon atom. Therefore, substituted cycloalkyl, substituted aryl, substituted heterocyclyl and substituted heteroaryl groups may be substituted with alkyl groups as defined above.

Pharmaceutically acceptable salts include a salt with an inorganic base, organic base, inorganic acid, organic acid, or basic or acidic amino acid. As salts of inorganic bases, the invention includes, for example, alkali metals such as sodium or potassium, alkali earth metals such as calcium and magnesium or aluminum, and ammonia. As salts of organic bases, the invention includes, for example, trimethylamine, triethylamine, pyridine, picoline, ethanolamine, diethanolamine, triethanolamine. As salts of inorganic acids, the instant invention includes, for example, hydrochloric acid, hydroboric acid, nitric acid, sulfuric acid, and phosphoric acid. As salts of organic acids, the instant invention includes, for example, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. As salts of basic amino acids, the instant invention includes, for example, arginine, lysine and ornithine. Acidic amino acids include, for example, aspartic acid and glutamic acid.

Prodrugs, as used in the context of the instant invention, includes those derivatives of the instant compounds which undergo in vivo metabolic biotransformation, by enzymatic or nonenzymatic processes, such as hydrolysis, to form a compound of the invention. Prodrugs can be employed to improve pharmaceutical or biological properties, as for example solubility, melting point, stability and related physicochemical properties, absorption, pharmacodynamics and other delivery-related properties.

The instant invention provides potent and specific agonists of MC4-R that are low molecular weight, non-peptide small molecules. In accordance with one aspect of the invention, the invention provides a first group of compounds of either formula IA or IB such as shown below.

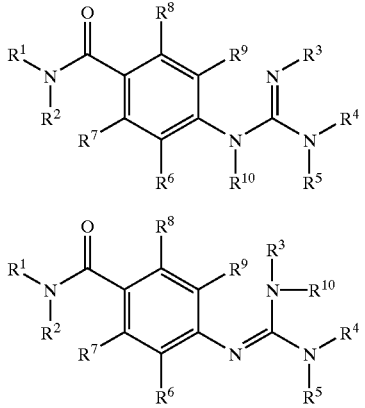

Compounds of the invention further include prodrugs of the first group of compounds of either formula IA or IB, pharmaceutically acceptable salts thereof, stereoisomers thereof, tautomers thereof, hydrates thereof, hydrides thereof, or solvates thereof.

In the first group of compounds of formula IA and IB, $R^1$ is selected from H, substituted or unsubstituted arylalkyl groups, substituted or unsubstituted heteroarylalkyl groups, substituted or unsubstituted aryl groups, substituted or unsubstituted heteroaryl groups, substituted or unsubstituted heterocyclyl groups, substituted or unsubstituted cycloalkyl groups, substituted or unsubstituted heterocyclylalkyl groups, substituted or unsubstituted cycloalkylalkyl groups, substituted or unsubstituted alkenyl groups, substituted or unsubstituted alkynyl groups, or substituted or unsubstituted alkyl groups. In various embodiments, $R^1$ is H.

In the first group of compounds of formula IA and IB, $R^2$ is selected from substituted or unsubstituted arylalkyl groups, substituted or unsubstituted heteroarylalkyl groups, substituted or unsubstituted aryl groups, substituted or unsubstituted heteroaryl groups, substituted or unsubstituted heterocyclyl groups, substituted or unsubstituted cycloalkyl groups, substituted or unsubstituted heterocyclylalkyl groups, substituted or unsubstituted cycloalkylalkyl groups, substituted or unsubstituted alkenyl groups, substituted or unsubstituted alkynyl groups, or substituted or unsubstituted alkyl groups. In various embodiments, $R^2$ is selected from substituted or unsubstituted arylalkyl groups, substituted or unsubstituted alkenyl groups, substituted or unsubstituted heteroarylalkyl groups, or substituted or unsubstituted heterocyclylalkyl groups. In still other embodiments, $R^2$ is a 2,4-disubstituted phenethyl groups such as, but not limited to a 2,4-dihalophenethyl group or a 2,4-dialkylphenethyl group. In still other embodiment, $R^2$ is selected from phenethyl, 2,4-dichlorophenethyl, 4-methoxyphenethyl, 4-bromophenethyl, 4-methylphenethyl, 4-chlorophenethyl, 4-chlorobenzyl, 4-ethylphenethyl, cyclohexenylethyl, 2-methoxyphenethyl, 2-chlorophenethyl, 2-fluorophenethyl, 3-methoxyphenethyl, 3-fluorophenethyl, thienylethyl, indolylethyl, 4-hydroxyphenethyl, 3,4-dimethoxyphenethyl, 2-chloro-4-iodophenethyl, 2-fluoro-4-methylphenethyl, 2-fluoro-4-bromophenethyl, 2-fluoro-4-methoxyphenethyl, 2-trifluoromethyl-4-fluorophenethyl, 2,4-difluorophenethyl, 2,4-dimethylphenethyl, or 2,4-dimethoxyphenethyl groups.

In the first group of compounds of formula IA and IB, $R^3$ is selected from substituted or unsubstituted alkyl groups, substituted or unsubstituted alkenyl groups, substituted or unsubstituted alkynyl groups, substituted or unsubstituted cycloalkyl groups, substituted or unsubstituted heteroaryl groups, substituted or unsubstituted heterocyclyl groups, substituted or unsubstituted heterocyclylalkyl groups, substituted or unsubstituted arylalkyl groups, substituted or unsubstituted heteroarylalkyl groups, or substituted or unsubstituted cycloalkylalkyl groups. In various embodiments, $R^3$ is selected from substituted or unsubstituted cycloalkyl groups, substituted or unsubstituted polycyclic cycloalkyl groups, substituted or unsubstituted alkenyl groups, substituted or unsubstituted alkyl groups, or substituted or unsubstituted aryl groups. In another embodiment, $R^3$ is selected from substituted or unsubstituted cyclohexyl groups, substituted or unsubstituted 2-alkylcyclohexyl groups, substituted or unsubstituted 2,2-dialkylcyclohexyl groups, substituted or unsubstituted 2,3-dialkylcyclohexyl groups, substituted or unsubstituted 2,4-dialkylcyclohexyl groups, substituted or unsubstituted 2,5-dialkylcyclohexyl groups, substituted or unsubstituted 2,6-dialkylcyclohexyl groups, substituted or unsubstituted 3,4-dialkylcyclohexyl groups, substituted or unsubstituted 3-alkylcyclohexyl groups, substituted or unsubstituted 4-alkylcyclohexyl groups, substituted or unsubstituted 3,3,5-trialkylcyclohexyl groups, substituted or unsubstituted cyclohexylmethyl groups, substituted or unsubstituted 2-aminocyclohexyl groups, substituted or unsubstituted 3-aminocyclohexyl groups, substituted or unsubstituted 4-aminocyclohexyl groups, substituted or unsubstituted 2,3-diaminocyclohexyl groups, substituted or unsubstituted 2,4-diaminocyclohexyl groups, substituted or unsubstituted 3,4-diaminocyclohexyl groups, substituted or unsubstituted 2,5-diaminocyclohexyl groups, substituted or unsubstituted 2,6-diaminocyclohexyl groups, substituted or unsubstituted 2,2-diaminocyclohexyl groups, substituted or unsubstituted 2-alkoxycyclohexyl groups, substituted or unsubstituted 3-alkoxycyclohexyl groups, substituted or unsubstituted 4-alkoxycyclohexyl groups, substituted or unsubstituted 2,3-dialkoxycyclohexyl groups, substituted or unsubstituted 2,4-dialkoxycyclohexyl groups, substituted or unsubstituted 3,4-dialkoxycyclohexyl groups, substituted or unsubstituted 2,5-dialkoxycyclohexyl groups, substituted or unsubstituted 2,6-dialkoxycyclohexyl groups, substituted or unsubstituted 2,2-dialkoxycyclohexyl groups, substituted or unsubstituted 2-alkylthiocyclohexyl groups, substituted or unsubstituted 3-alkylthiocyclohexyl groups, 4-alkylthiocyclohexyl groups, substituted or unsubstituted 2,3-dialkylthiocyclohexyl groups, substituted or unsubstituted 2,4-dialkylthiocyclohexyl groups, substituted or unsubstituted 3,4-dialkylthiocyclohexyl groups, substituted or unsubstituted 2,5-dialkylthiocyclohexyl groups, substituted or unsubstituted 2,6-dialkylthiocyclohexyl groups, substituted or unsubstituted 2,2-dialkylthiocyclohexyl groups, substituted or unsubstituted cyclopentyl groups, substituted or unsubstituted cycloheptyl groups, substituted or unsubstituted cyclohexenyl groups, substituted or unsubstituted isopropyl groups, substituted or unsubstituted n-butyl groups, substituted or unsubstituted cyclooctyl groups, substituted or unsubstituted 2-arylcyclohexyl groups, substituted or unsubstituted 2-phenylcyclohexyl groups, substituted or unsubstituted 2-arylalkylcyclohexyl groups, substituted or unsubstituted 2-benzylcyclohexyl groups, substituted or unsubstituted 4-phenylcyclohexyl groups, substituted or unsubstituted adamantyl groups, substituted or unsubstituted isocamphenyl groups, substituted or unsubstituted carenyl groups, substituted or unsubstituted 7,7-dialkylnorbornyl groups, substituted or unsubstituted bornyl groups, substituted or unsubstituted norbornyl groups, or substituted or unsubstituted decalinyl groups. In another embodiment, $R^3$ is selected from substituted or unsubstituted cyclohexyl groups, substituted or unsubstituted 2-methylcyclohexyl groups, substituted or unsubstituted 2,2-dimethylcyclohexyl groups, substituted or unsubstituted 2,3-dimethylcyclohexyl groups, substituted or unsubstituted 2,4-dimethylcyclohexyl groups, substituted or unsubstituted 2,5-dimethylcyclohexyl groups, substituted or unsubstituted 2,6-dimethylcyclohexyl groups, substituted or unsubstituted 3,4-dimethylcyclohexyl groups, substituted or unsubstituted 3-methylcyclohexyl groups, substituted or unsubstituted 4-methylcyclohexyl groups, substituted or unsubstituted cyclohex-3-enyl groups, substituted or unsubstituted 3,3,5-trimethylcyclohexyl groups, substituted or unsubstituted 4-t-butylcyclohexyl groups, substituted or unsubstituted 2-methylcycloheptyl groups, substituted or unsubstituted cyclohexylmethyl groups, substituted or unsubstituted isopinocampheyl groups, substituted or unsubstituted 7,7-dimethylnorbornyl groups, substituted or unsubstituted 4-isopropylcyclohexyl groups, or 3-methylcycloheptyl groups.

In the first group of compounds of formula IA and IB, $R^4$ is selected from hydrogen, substituted or unsubstituted alkyl groups, substituted or unsubstituted alkenyl groups, substituted or unsubstituted alkynyl groups, substituted or unsubstituted cycloalkyl groups, substituted or unsubstituted aryl groups, substituted or unsubstituted heteroaryl groups, substituted or unsubstituted heterocyclyl groups, substituted or unsubstituted arylalkyl groups, substituted or unsubstituted heteroarylalkyl groups, or substituted or unsubstituted cycloalkylalkyl groups.

In the first group of compounds of formula IA and IB, $R^5$ is selected from substituted or unsubstituted alkyl groups, substituted or unsubstituted alkenyl groups, substituted or unsubstituted alkynyl groups, substituted or unsubstituted cycloalkyl groups, substituted or unsubstituted aryl groups, substituted or unsubstituted heteroaryl groups, substituted or unsubstituted heterocyclyl groups, substituted or unsubstituted arylalkyl groups, substituted or unsubstituted heteroarylalkyl groups, or substituted or unsubstituted cycloalkylalkyl groups.

In alternative embodiments of the first group of compounds of formula IA and IB, $R^4$ and $R^5$, together with the nitrogen to which they are bound, form a substituted or unsubstituted heterocyclyl or heteroaryl group. In another such embodiment, $R^4$ and $R^5$, together with the nitrogen to which they are bound, form a substituted or unsubstituted saturated heterocyclyl group comprising at least one heteroatom selected from O, S, or N in addition to the N atom to which $R^4$ and $R^5$ are bound. In another embodiment, $R^4$ and $R^5$, together with the nitrogen to which they are bound, form a substituted or unsubstituted heterocyclyl ring containing at least one additional nitrogen heteroatom. In still another embodiment, $R^4$ and $R^5$, together with the nitrogen to which they are bound, form a substituted or unsubstituted heterocyclyl ring containing at least one additional oxygen heteroatom. Representative examples of the above-described heterocyclyl embodiments include those for which $R^4$ and $R^5$ together with the nitrogen atom to which they are attached form a substituted or unsubstituted piperazino, morpholino, pyrrolidino, piperidino, homopiperazino, or azepino group. In another, more specific, embodiment, $R^4$ and $R^5$, together with the nitrogen to which they are bound, form a substituted piperazino; and, in still more specific embodiments, $R^4$ and $R^5$, together with the nitrogen to which they are bound, form a substituted piperazino group optionally substituted by one or two alkyl groups, for example, one or two methyl groups.

In another embodiment of the first group of compounds of formula IA and IB, $R^4$ is H and $R^5$ is selected from substituted or unsubstituted alkyl groups, substituted or unsubstituted arylalkyl groups, or substituted or unsubstituted heteroarylalkyl groups. In another embodiment, $R^4$ is H and $R^5$ is selected from substituted or unsubstituted dialkylaminoethyl groups, substituted or unsubstituted 4-ethylbenzyl groups, substituted or unsubstituted 3-chlorobenzyl groups, substituted or unsubstituted 2,4-dichlorobenzyl groups, substituted or unsubstituted 3-methylbenzyl groups, substituted or unsubstituted benzyl groups, substituted or unsubstituted 4-fluorobenzyl groups, substituted or unsubstituted 3-methoxybenzyl groups, substituted or unsubstituted 2-chlorobenzyl groups, or substituted or unsubstituted thiophene groups. In another embodiment, $R^4$ and $R^5$ may be the same or different and are each independently selected from substituted or unsubstituted alkyl groups, substituted or unsubstituted arylalkyl groups, or substituted or unsubstituted heteroarylalkyl groups. In another embodiment, $R^4$ and $R^5$ may be the same or different and are each independently selected from substituted or unsubstituted dialkylaminoethyl groups, substituted or unsubstituted 4-ethylbenzyl groups, substituted or unsubstituted 3-chlorobenzyl groups, substituted or unsubstituted 2,4-dichlorobenzyl groups, substituted or unsubstituted 3-methylbenzyl groups, substituted or unsubstituted benzyl groups, substituted or unsubstituted 4-fluorobenzyl groups, substituted or unsubstituted 3-methoxybenzyl groups, substituted or unsubstituted 2-chlorobenzyl groups, and substituted or unsubstituted thiophene groups.

In the first group of compounds of formula IA and IB, $R^6$, $R^7$, $R^8$, and $R^9$ may be the same or different, and are each independently selected from H, Cl, I, F, Br, OH, $NH_2$, CN, $NO_2$, substituted or unsubstituted alkoxy groups, substituted or unsubstituted amino groups, substituted or unsubstituted alkyl groups, substituted or unsubstituted alkenyl groups, substituted or unsubstituted alkynyl groups, substituted or unsubstituted alkylamino groups, substituted or unsubstituted dialkylamino groups, substituted or unsubstituted cycloalkyl groups, substituted or unsubstituted heterocyclylamino groups, substituted or unsubstituted heteroarylamino groups, substituted or unsubstituted aminocarbonyl groups, substituted or unsubstituted alkylaminocarbonyl groups, substituted or unsubstituted dialkylaminocarbonyl groups, substituted or unsubstituted cycloalkylaminocarbonyl groups, substituted or unsubstituted arylaminocarbonyl groups, substituted or unsubstituted heterocyclylaminocarbonyl groups, or substituted or unsubstituted heteroarylaminocarbonyl groups.

In the first group of compounds of formula IA and IB, $R^{10}$ is selected from H, substituted or unsubstituted alkyl groups, substituted or unsubstituted alkenyl groups, substituted or unsubstituted alkynyl groups, substituted or unsubstituted cycloalkylalkyl groups, substituted or unsubstituted aryl groups, or substituted or unsubstituted arylalkyl groups. In various embodiments, $R^{10}$ is H.

There has also been provided, in accordance with another aspect of the invention, a second group of compound of either formula IA or IB:

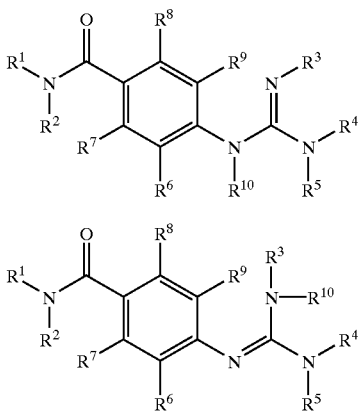

Compounds of the invention further include prodrugs of the second group of compounds of either formula IA or IB, pharmaceutically acceptable salts thereof, stereoisomers thereof, tautomers thereof, hydrates thereof, hydrides thereof, or solvates thereof.

In the second group of compound of formula IA and IB, $R^1$ is selected from H, substituted or unsubstituted arylalkyl groups, substituted or unsubstituted heteroarylalkyl groups, substituted or unsubstituted aryl groups, substituted or unsubstituted heterocyclyl groups, substituted or unsubstituted cycloalkyl groups, substituted or unsubstituted heterocyclylalkyl groups, substituted or unsubstituted cycloalkylalkyl groups, substituted or unsubstituted alkenyl groups, substituted or unsubstituted alkynyl groups, or substituted or unsubstituted alkyl groups. In various embodiments, $R^1$ is H.

In the second group of compound of formula IA and IB, $R^2$ is selected from substituted or unsubstituted arylalkyl groups, substituted or unsubstituted heteroarylalkyl groups, substituted or unsubstituted aryl groups, substituted or unsubstituted heterocyclyl groups, substituted or unsubstituted cycloalkyl groups, substituted or unsubstituted heterocyclylalkyl groups, substituted or unsubstituted cycloalkylalkyl groups, substituted or unsubstituted alkenyl groups, substituted or unsubstituted alkynyl groups, or substituted or unsubstituted alkyl groups. In another embodiment, $R^2$ is selected from substituted or unsubstituted arylalkyl, alkenyl, heteroarylalkyl, or heterocyclylalkyl groups. In another embodiment, $R^2$ is 2,4-disubstituted phenethyl. In still another embodiment, $R^2$ is selected from 2,4-dihalophenethyl, or 2,4-dialkylphenethyl. In another embodiment, $R^2$ is selected from phenethyl, 2,4-dichlorophenethyl, 4-methoxyphenethyl, 4-bromophenethyl, 4-methylphenethyl, 4-chlorophenethyl, 4-chlorobenzyl, 4-ethylphenethyl, cyclohexenylethyl, 2-methoxyphenethyl, 2-chlorophenethyl, 2-fluorophenethyl, 3-methoxyphenethyl, 3-fluorophenethyl, thienylethyl, indolylethyl, 4-hydroxyphenethyl, 3,4-dimethoxyphenethyl, 2-chloro-4-iodophenethyl, 2-fluoro-4-methylphenethyl, 2-fluoro-4-bromophenethyl, 2-fluoro-4-methoxyphenethyl, 2-trifluoromethyl-4-fluorophenethyl, 2,4-difluorophenethyl, 2,4-dimethylphenethyl, or 2,4-dimethoxyphenethyl groups.

In the second group of compound of formula IA and IB, $R^3$ is selected from H, substituted or unsubstituted alkyl groups, substituted or unsubstituted alkenyl, alkynyl groups, substituted or unsubstituted cycloalkyl groups, substituted or unsubstituted aryl groups, substituted or unsubstituted heteroaryl groups, substituted or unsubstituted heterocyclyl groups, substituted or unsubstituted arylalkyl groups, substituted or unsubstituted heteroarylalkyl groups, or substituted or unsubstituted cycloalkylalkyl groups. In various embodiments, $R^3$ is selected from substituted or unsubstituted cycloalkyl groups, substituted or unsubstituted polycyclic cycloalkyl groups, substituted or unsubstituted alkenyl groups, substituted or unsubstituted alkyl groups, or substituted or unsubstituted aryl groups. In various embodiments, $R^3$ is selected from substituted or unsubstituted cyclohexyl, 2-alkylcyclohexyl, 2,2-dialkylcyclohexyl, 2,3-dialkylcyclohexyl, 2,4-dialkylcyclohexyl, 2,5-dialkylcyclohexyl, 2,6-dialkylcyclohexyl, 3,4-dialkylcyclohexyl, 3-alkylcyclohexyl, 4-alkylcyclohexyl, 3,3,5-trialkylcyclohexyl, cyclohexylmethyl, 2-aminocyclohexyl, 3-aminocyclohexyl, 4-aminocyclohexyl, 2,3-diaminocyclohexyl, 2,4-diaminocyclohexyl, 3,4-diaminocyclohexyl, 2,5-diaminocyclohexyl, 2,6-diaminocyclohexyl, 2,2-diaminocyclohexyl, 2-alkoxycyclohexyl, 3-alkoxycyclohexyl, 4-alkoxycyclohexyl, 2,3-dialkoxycyclohexyl, 2,4-dialkoxycyclohexyl, 3,4-dialkoxycyclohexyl, 2,5-dialkoxycyclohexyl, 2,6-dialkoxycyclohexyl, 2,2-dialkoxycyclohexyl, 2-alkylthiocyclohexyl, 3-alkylthiocyclohexyl, 4-alkylthiocyclohexyl, 2,3-dialkylthiocyclohexyl, 2,4-dialkylthiocyclohexyl, 3,4-dialkylthiocyclohexyl, 2,5-dialkylthiocyclohexyl, 2,6-dialkylthiocyclohexyl, 2,2-dialkylthiocyclohexyl, cyclopentyl, cycloheptyl, cyclohexenyl, isopropyl, n-butyl, cyclooctyl, 2-arylcyclohexyl, 2-phenylcyclohexyl, 2-arylalkylcyclohexyl, 2-benzylcyclohexyl, 4-phenylcyclohexyl, adamantyl, isocamphenyl, carenyl, 7,7-dialkylnorbornyl, bornyl, norbornyl, or decalinyl groups. In another embodiment, $R^3$ is selected from substituted or unsubstituted cyclohexyl, 2-methylcyclohexyl, 2,2-dimethylcyclohexyl, 2,3-dimethylcyclohexyl, 2,4-dimethylcyclohexyl, 2,5-dimethylcyclohexyl, 2,6-dimethylcyclohexyl, 3,4-dimethylcyclohexyl, 3-methylcyclohexyl, 4-methylcyclohexyl, cyclohexenyl, 3,3,5-trimethylcyclohexyl, 4-t-butylcyclohexyl, 2-methylcycloheptyl, cyclohexylmethyl, isopinocampheyl, 7,7-dimethylnorbornyl, 4-isopropylcyclohexyl, or 3-methylcycloheptyl groups.

In the second group of compound of formula IA and IB, $R^4$ and $R^5$, together with the N atom to which they are bound, form a substituted or unsubstituted saturated heterocyclyl group comprising at least one heteroatom selected from the group consisting of O, S, and N in addition to the N atom to which $R^4$ and $R^5$ are bound. In another embodiment, $R^4$ and $R^5$, together with the nitrogen to which they are bound, form a substituted or unsubstituted heterocyclyl ring containing at least one additional nitrogen heteroatom. In still another embodiment, $R^4$ and $R^5$, together with the nitrogen to which they are bound, form a substituted or unsubstituted heterocyclyl ring containing at least one additional oxygen heteroatom. Representative examples of the above-described heterocyclyl embodiments include those for which $R^4$ and $R^5$ together with the nitrogen atom to which they are attached form a substituted or unsubstituted piperazino, morpholino, pyrrolidino, piperidino, homopiperazino, or azepino group. In another, more specific, embodiment, $R^4$ and $R^5$, together with the nitrogen to which they are bound, form a substituted piperazino; and, in still more specific embodiments, $R^4$ and $R^5$, together with the nitrogen to which they are bound, form a substituted piperazino group optionally substituted by one or two alkyl groups, for example, one or two methyl groups.

In the second group of compound of formula IA and IB, $R^6$, $R^7$, $R^8$, and $R^9$ may be the same or different, and are each independently selected from H, Cl, I, F, Br, OH, $NH_2$, CN, $NO_2$, substituted or unsubstituted alkoxy groups, substituted or unsubstituted amino groups, substituted or unsubstituted alkyl groups, substituted or unsubstituted alkenyl groups, substituted or unsubstituted alkynyl groups, substituted or unsubstituted alkylamino groups, substituted or unsubstituted dialkylamino groups, substituted or unsubstituted cycloalkyl groups, substituted or unsubstituted heterocyclylamino groups, substituted or unsubstituted heteroarylamino groups, substituted or unsubstituted aminocarbonyl groups, substituted or unsubstituted alkylaminocarbonyl groups, substituted or unsubstituted dialkylaminocarbonyl groups, substituted or unsubstituted cycloalkylaminocarbonyl groups, substituted or unsubstituted arylaminocarbonyl groups, substituted or unsubstituted heterocyclylaminocarbonyl groups, or substituted or unsubstituted heteroarylaminocarbonyl groups.

In the second group of compound of formula IA and IB, $R^{10}$ is selected from H, substituted or unsubstituted arylalkyl groups, substituted or unsubstituted heteroarylalkyl groups, substituted or unsubstituted aryl groups, substituted or unsubstituted heteroaryl groups, substituted or unsubstituted heterocyclyl groups, substituted or unsubstituted cycloalkyl groups, substituted or unsubstituted heterocyclylalkyl groups, substituted or unsubstituted cycloalkylalkyl groups, substituted or unsubstituted alkenyl groups, substituted or unsubstituted alkynyl groups, or substituted or unsubstituted alkyl groups. In one embodiment $R^{10}$ is H.

There has also been provided, in accordance with another aspect of the invention, a compound of either formula IIA or IIB:

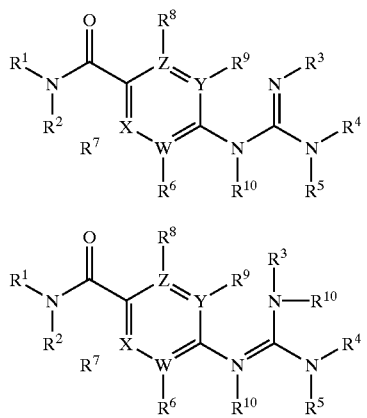

Compounds of the invention further include prodrugs of the compounds of either formula IIA or IIB, pharmaceutically acceptable salts thereof, stereoisomers thereof, tautomers thereof, hydrates thereof, hydrides thereof, or solvates thereof.

In the compounds of formula IIA and IIB, W, X, Y, and Z are carbon or nitrogen. In some embodiments, at least one of W, X, Y, or Z is a nitrogen atom. In more specific embodiments, three of W, X, Y, and Z are carbon, and one of W, X, Y, and Z is nitrogen, forming, thereby a pyridyl group. In more particular embodiments, each of X, Y, and Z is carbon, and W is nitrogen. Still other more particular embodiments are those for which each of W, X, and Z is carbon, and Y is nitrogen.

In the compounds of formula IIA and IIB, $R^1$ is selected from H, substituted or unsubstituted arylalkyl groups, substituted or unsubstituted heteroarylalkyl groups, substituted or unsubstituted aryl groups, substituted or unsubstituted heteroaryl groups, substituted or unsubstituted heterocyclyl groups, substituted or unsubstituted cycloalkyl groups, substituted or unsubstituted heterocyclylalkyl groups, substituted or unsubstituted cycloalkylalkyl groups, substituted or unsubstituted alkenyl groups, substituted or unsubstituted alkynyl groups, or substituted or unsubstituted alkyl groups. In various embodiments, $R^1$ is H.

In the compounds of formula IIA and IIB, $R^2$ is selected from substituted or unsubstituted arylalkyl groups, substituted or unsubstituted heteroarylalkyl groups, substituted or unsubstituted aryl groups, substituted or unsubstituted heteroaryl groups, substituted or unsubstituted heterocyclyl groups, substituted or unsubstituted cycloalkyl groups, substituted or unsubstituted heterocyclylalkyl groups, substituted or unsubstituted cycloalkylalkyl groups, substituted or unsubstituted alkenyl groups, substituted or unsubstituted alkynyl groups, or substituted or unsubstituted alkyl groups. In various embodiments, $R^2$ is selected from substituted or unsubstituted arylalkyl, alkenyl, heteroarylalkyl, or heterocyclylalkyl groups. In other embodiments, $R^2$ is 2,4-disubstituted phenethyl. In another embodiment, $R^2$ is selected from 2,4-dihalophenethyl or 2,4-dialkylphenethyl groups. In another embodiment, $R^2$ is selected from substituted or unsubstituted phenethyl, 2,4-dichlorophenethyl, 4-methoxyphenethyl, 4-bromophenethyl, 4-methylphenethyl, 4-chlorophenethyl, 4-chlorobenzyl, 4-ethylphenethyl, cyclohexenylethyl, 2-methoxyphenethyl, 2-chlorophenethyl, 2-fluorophenethyl, 3-methoxyphenethyl, 3-fluorophenethyl, thienylethyl, indolylethyl, 4-hydroxyphenethyl, 3,4-dimethoxyphenethyl, 2-chloro-4-iodophenethyl, 2-fluoro-4-methylphenethyl, 2-fluoro-4-bromophenethyl, 2-fluoro-4-methoxyphenethyl, 2-trifluoromethyl-4-fluorophenethyl, 2,4-difluorophenethyl, 2,4-dimethylphenethyl, or 2,4-dimethoxyphenethyl groups.

In the compounds of formula IIA and IIB, $R^3$ is selected from H, substituted or unsubstituted alkyl groups, substituted or unsubstituted alkenyl groups, substituted or unsubstituted alkynyl groups, substituted or unsubstituted cycloalkyl groups, substituted or unsubstituted heteroaryl groups, substituted or unsubstituted heterocyclyl groups, substituted or unsubstituted heterocyclylalkyl groups, substituted or unsubstituted arylalkyl groups, substituted or unsubstituted heteroarylalkyl groups, or substituted or unsubstituted cycloalkylalkyl groups. In various embodiments, $R^3$ is selected from substituted or unsubstituted cycloalkyl, polycyclic cycloalkyl, alkenyl, alkyl, or aryl groups. In other embodiments, $R^3$ is selected from substituted or unsubstituted cyclohexyl, 2-alkylcyclohexyl, 2,2-dialkylcyclohexyl, 2,3-dialkylcyclohexyl, 2,4-dialkylcyclohexyl, 2,5-dialkylcyclohexyl, 2,6-dialkylcyclohexyl, 3,4-dialkylcyclohexyl, 3-alkylcyclohexyl, 4-alkylcyclohexyl, 3,3,5-trialkylcyclohexyl, cyclohexylmethyl, 2-aminocyclohexyl, 3-aminocyclohexyl, 4-aminocyclohexyl, 2,3-diaminocyclohexyl, 2,4-diaminocyclohexyl, 3,4-diaminocyclohexyl, 2,5-diaminocyclohexyl, 2,6-diaminocyclohexyl, 2,2-diaminocyclohexyl, 2-alkoxycyclohexyl, 3-alkoxycyclohexyl, 4-alkoxycyclohexyl, 2,3-dialkoxycyclohexyl, 2,4-dialkoxycyclohexyl, 3,4-dialkoxycyclohexyl, 2,5-dialkoxycyclohexyl, 2,6-dialkoxycyclohexyl, 2,2-dialkoxycyclohexyl, 2-alkylthiocyclohexyl, 3-alkylthiocyclohexyl, 4-alkylthiocyclohexyl, 2,3-dialkylthiocyclohexyl, 2,4-dialkylthiocyclohexyl, 3,4-dialkylthiocyclohexyl, 2,5-dialkylthiocyclohexyl, 2,6- dialkylthiocyclohexyl, 2,2-dialkylthiocyclohexyl, cyclopentyl, cycloheptyl, cyclohexenyl, isopropyl, n-butyl, cyclooctyl, 2-arylcyclohexyl, 2-phenylcyclohexyl, 2-arylalkylcyclohexyl, 2-benzylcyclohexyl, 4-phenylcyclohexyl, adamantyl, isocamphenyl, carenyl, 7,7-dialkylnorbornyl, norbornyl, bornyl, or decalinyl groups. In other embodiment, $R^3$ is selected from substituted or unsubstituted cyclohexyl, 2-methylcyclohexyl, 2,2-dimethylcyclohexyl, 2,3-dimethylcyclohexyl, 2,4-dimethylcyclohexyl, 2,5-dimethylcyclohexyl, 2,6-dimethylcyclohexyl, 3,4-dimethylcyclohexyl, 3-methylcyclohexyl, 4-methylcyclohexyl, cyclohexenyl, 3,3,5-trimethylcyclohexyl, 4-t-butylcyclohexyl, cyclohexyl methyl, isopinocampheyl, 7,7-dimethyinorbornyl, 4-isopropylcyclohexyl, or 3-methylcycloheptyl groups.

In the compounds of formula IIA and IIB, $R^4$ is selected from the H, substituted or unsubstituted alkyl groups, substituted or unsubstituted alkenyl groups, substituted or unsubstituted alkynyl groups, substituted or unsubstituted cycloalkyl groups, substituted or unsubstituted aryl groups, substituted or unsubstituted heteroaryl groups, substituted or unsubstituted heterocyclyl groups, substituted or unsubstituted arylalkyl groups, substituted or unsubstituted heteroarylalkyl groups, or substituted or unsubstituted cycloalkylalkyl groups.

In the compounds of formula IIA and IIB, $R^5$ is selected from substituted or unsubstituted alkyl groups, substituted or unsubstituted alkenyl groups, substituted or unsubstituted alkynyl groups, substituted or unsubstituted cycloalkyl groups, substituted or unsubstituted aryl groups, substituted or unsubstituted heteroaryl groups, substituted or unsubstituted heterocyclyl groups, substituted or unsubstituted arylalkyl groups, substituted or unsubstituted heteroarylalkyl groups, or substituted or unsubstituted cycloalkylalkyl groups.

In some embodiments of compounds of formula IIA and IIB, $R^4$ is H and $R^5$ is selected from substituted or unsubstituted alkyl, arylalkyl, and heteroarylalkyl groups. In other embodiments, $R^4$ is H and $R^5$ is selected from substituted or unsubstituted dialkylaminoethyl, 4-ethylbenzyl, 3-chlorobenzyl, 2,4-dichlorobenzyl, 3-methylbenzyl, benzyl, 4-fluorobenzyl, 3-methoxybenzyl, 2-chlorobenzyl, and thiophene groups. In other embodiments, $R^4$ and $R^5$ may be the same or different and are each independently selected from substituted or unsubstituted alkyl, arylalkyl, or heteroarylalkyl groups. In various other embodiments, $R^4$ and $R^5$ may be the same or different and are each independently selected from substituted or unsubstituted dialkylaminoethyl, 4-ethylbenzyl, 3-chlorobenzyl, 2,4-dichlorobenzyl, 3-methylbenzyl, benzyl, 4-fluorobenzyl, 3-methoxybenzyl, 2-chlorobenzyl, or thiophene groups.

In the compounds of formula IIA and IIB, $R^4$ and $R^5$, together with the nitrogen to which they are bound, may form a substituted or unsubstituted heterocyclyl or heteroaryl group. In another such embodiment, $R^4$ and $R^5$, together with the nitrogen to which they are bound, form a substituted or unsubstituted saturated heterocyclyl group comprising at least one heteroatom selected from O, S, or N in addition to the N atom to which $R^4$ and $R^5$ are bound. In another embodiment, $R^4$ and $R^5$, together with the nitrogen to which they are bound, form a substituted or unsubstituted heterocyclyl ring containing at least one additional nitrogen heteroatom. In still another embodiment, $R^4$ and $R^5$, together with the nitrogen to which they are bound, form a substituted or unsubstituted heterocyclyl ring containing at least one additional oxygen heteroatom. Representative examples of the above-described heterocyclyl embodiments include those for which $R^4$ and $R^5$ together with the nitrogen atom to which they are attached form a substituted or unsubstituted piperazino, morpholino, pyrrolidino, piperidino, homopiperazino, or azepino group. In another, more specific, embodiment, $R^4$ and $R^5$, together with the nitrogen to which they are bound, form a substituted piperazino; and, in still more specific embodiments, $R^4$ and $R^5$, together with the nitrogen to which they are bound, form a substituted piperazino group optionally substituted by one or two alkyl groups, for example, one or two methyl groups.

In the compounds of formula IIA and IIB, $R^6$, $R^7$, $R^8$, and $R^9$ may be the same or different, and are each independently selected from H, Cl, I, F, Br, OH, $NH_2$, CN, $NO_2$, substituted or unsubstituted alkoxy groups, substituted or unsubstituted amino groups, substituted or unsubstituted alkyl groups, substituted or unsubstituted alkenyl groups, substituted or unsubstituted alkynyl groups, substituted or unsubstituted alkylamino groups, substituted or unsubstituted dialkylamino groups, substituted or unsubstituted cycloalkyl groups, substituted or unsubstituted heterocyclylamino groups, substituted or unsubstituted heteroarylamino groups, substituted or unsubstituted aminocarbonyl groups, substituted or unsubstituted alkylaminocarbonyl groups, substituted or unsubstituted dialkylaminocarbonyl groups, substituted or unsubstituted cycloalkylaminocarbonyl groups, substituted or unsubstituted arylaminocarbonyl groups, substituted or unsubstituted heterocyclylaminocarbonyl groups, or substituted or unsubstituted heteroarylaminocarbonyl groups. In compounds of formula IIA and IIB, $R^6$ may be absent if W is a nitrogen atom; $R^7$ may be absent if X is a nitrogen atom; $R^8$ may be absent if Z is a nitrogen atom; and $R^9$ may be absent if Y is a nitrogen atom.

In the compounds of formula IIA and IIB, $R^{10}$ is selected from H, and substituted or unsubstituted alkyl groups, substituted or unsubstituted alkenyl groups, substituted or unsubstituted alkynyl groups, substituted or unsubstituted cycloalkylalkyl groups, substituted or unsubstituted aryl groups, or arylalkyl groups. In some embodiments, $R^{10}$ is H.

There has also been provided, in accordance with another aspect of the invention, a composition comprising a compound according to the instant invention and a pharmaceutically acceptable carrier.

There has also been provided, in accordance with another aspect of the invention, a method of activating MC4-R in a subject, comprising administering to a subject in need thereof an effective amount of a compound or composition of the instant invention.

There has also been provided, in accordance with another aspect of the invention, a method of treating an MC4-R-mediated disease, comprising administering to a subject in need thereof, a compound or composition of the instant invention.

In one embodiment, a disease to be treated by those methods of the instant invention is obesity, or type I or type II diabetes.

In another embodiment, a condition to be treated by those methods of the instant invention is a condition associated with or a complication arising from obesity or type II diabetes.

In another embodiment, a condition to be treated by those methods of the instant invention is erectile dysfunction.

In another embodiment, a disease to be treated by those methods of the instant invention is polycystic ovary disease.

In another embodiment, a disease to be treated by those methods of the instant invention is Syndrome X.

The invention also includes tautomers of the instant compounds. For example, the instant invention also includes those tautomers of formula IA such as the following where $R^{10}$ is H in formula IA above and the following structure shows the tautomer:

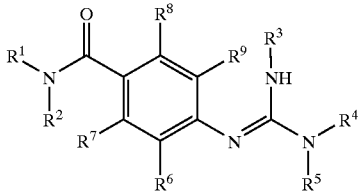

Similarly, the instant invention also contemplates those tautomers of compounds of formula IIA, such as the following where $R^{10}$ is H in formula IIA above and the following structure shows the structure of the tautomer:

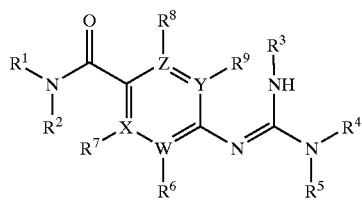

wherein $R^1$, $R^2$, $R^3$, $R^4$, $R^5$, $R^6$, $R^7$, $R^8$, $R^9$, $R^{10}$ W, X, Y and Z are as defined herein. The instant invention also, therefore, includes prodrugs, pharmaceutically acceptable salts, stereoisomers, hydrates, hydrides, or solvates of these tautomers.

The instant compounds may exist as one or more stereoisomers. The various stereoisomers include enantiomers, diastereomers, atropisomers and geometric isomers. In some cases, one stereoisomer may be more active and/or may exhibit beneficial effects in comparison to other stereoisomer(s) or when separated from the other stereoisomer(s). However, it is well within the skill of the ordinary artisan to separate, and/or to selectively prepare said stereoisomers. Accordingly, "stereoisomers" of the instant invention necessarily includes mixtures of stereoisomers, individual stereoisomers, or optically active forms.

Generally, compounds of formula IA may be prepared, for example, by a method comprising coupling of a compound of formula $R^1R^2NH$ with 4-azidobenzoic acid to give W:

W

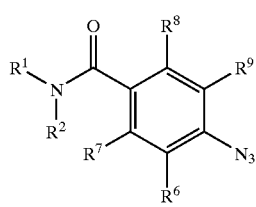

Compound W is then reacted with a leaving group, such as, for example, triphenylphosphine ($PPh_3$), to give X:

X

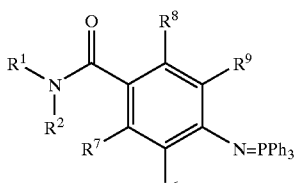

The intermediate of formula X is then contacted with an isocyanate of formula $OCNR^3$ and a compound of formula $R^4R^5HN$ to obtain a compound of formula IA above, prodrugs thereof, pharmaceutically acceptable salts thereof, stereoisomers thereof, tautomers thereof, hydrates thereof, hydrides thereof, or solvates thereof, wherein $R^1$, $R^2$, $R^3$, $R^4$, $R^5$, and $R^6$ are as defined above. It will also be appreciated that other groups may replace $PPh_3$, such as, for example, any phosphines ($PR_3$), phosphites $\{P(OR)_3\}$, or arsine ($AsPh_3$).

Preparation of compounds of formula IA wherein $R^{10}$ is hydrogen can be summarized, for example, by the following synthesis scheme:

Synthesis Scheme

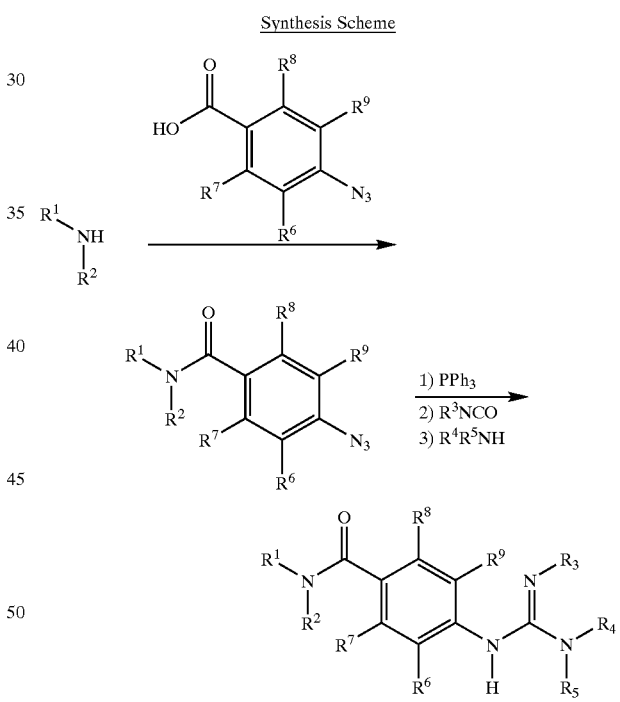

Compound of formula IA in which $R^{10}$ is a substituent other than hydrogen (e.g. alkyl or aralkyl) can be prepared as follows.

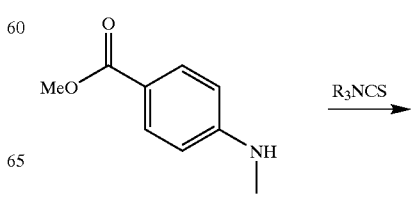

-continued

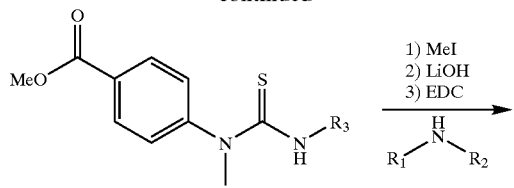

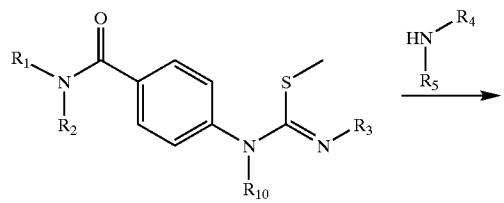

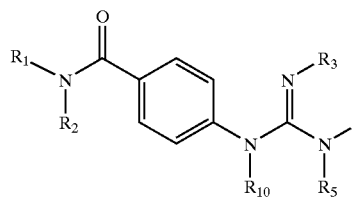

Compounds having the general structure shown in formula IB can be prepared using the generic synthetic scheme shown below.

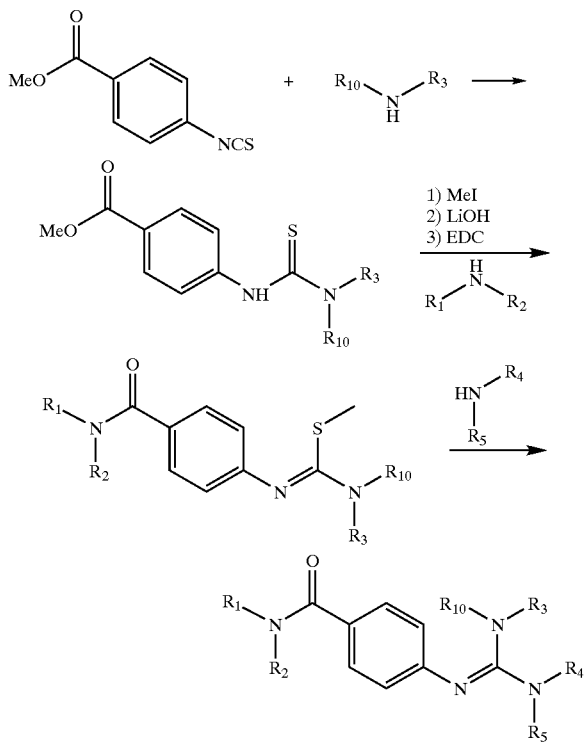

Alternatively, compounds of formula IIA may be prepared, for example, by a method comprising contacting a compound of formula $R^1R^2HN$ with a compound of formula Y:

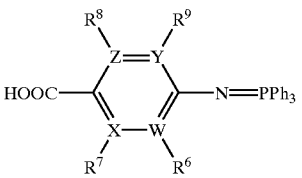

to obtain an intermediate of formula Z:

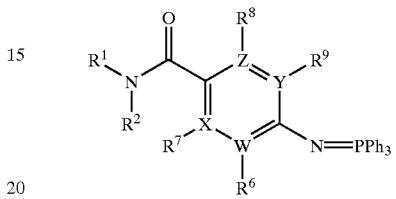

The intermediate of formula Z is then contacted with an isocyanate of formula $OCNR^3$ and a compound of formula $R^4R^5HN$ to obtain a compound of formula IIA above, prodrugs thereof, pharmaceutically acceptable salts thereof, stereoisomers thereof, tautomers thereof, hydrates thereof, hydrides thereof, or solvates thereof, wherein $R^1, R^2, R^3, R^4, R^5$, and $R^6$ are as defined above.

Specifically, compounds of the instant invention may be prepared, for example, by reacting a suitable azidobenzoic acid, or a suitable acid halide thereof, with a suitable amino compound represented of formula $R^1R^2HN$. The reaction may be carried out in solid phase in the presence of an inert solvent, for example, an aprotic solvent such as pyridine, methylene chloride, tetrahydrofuran, N,N-dimethylformamide or dimethylsulfoxide, or a mixture thereof. The condensation product may be optionally purified, and is reacted with phosphine, a suitable isocyanate of formula $OCNR^3$ and a compound of formula $R^4R^5HN$. The addition product may then be deprotected from the resin, if needed, by elution with a suitable acid such as a 4:1 mixture of trifluoroacetic acid and methylene chloride. Further purification can be accomplished through conventional means such as filtration, extraction and re-crystallization.

The instant invention also provides for compositions which may be prepared by mixing one or more compounds of the instant invention, or pharmaceutically acceptable salts or tautomers thereof, with pharmaceutically acceptable carriers, excipients, binders, diluents or the like, to treat or ameliorate a variety of disorders. Examples of such disorders include, but are not limited to obesity, erectile disorders, cardiovascular disorders, neuronal injuries or disorders, inflammation, fever, cognitive disorders, sexual behavior disorders. A therapeutically effective dose further refers to that amount of one or more compounds of the instant invention sufficient to result in amelioration of symptoms of the disorder. The pharmaceutical compositions of the instant invention can be manufactured by methods well known in the art such as conventional granulating, mixing, dissolving, encapsulating, lyophilizing, emulsifying or levigating processes, among others. The compositions can be in the form of, for example, granules, powders, tablets, capsules, syrup, suppositories, injections, emulsions, elixirs, suspensions or solutions. The instant compositions can be formulated for various routes of administration, for example, by oral administration, by intranasal administration, by transmucosal administration, by rectal administration, or subcutaneous administration as well as intrathecal, intravenous, intramuscular, intraperitoneal, intranasal, intraocular or intraventricular injection. The compound or compounds of the instant invention can also be administered in a local rather than a systemic fashion, such as injection as a sustained release formulation. The following dosage forms are given by way of example and should not be construed as limiting the instant invention.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or pharmaceutically acceptable salts or tautomers thereof, with at least one additive or excipient such as a starch or other additive. Suitable additives or excipients are sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethylcellulose, and/or polyvinylpyrrolidone. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, a thickeners, buffers, a sweeteners, flavoring agents or perfuming agents. Additionally, dyestuffs or pigments may be added for identification. Tablets and pills may be further treated with suitable coating materials known in the art.

Liquid dosage forms for oral administration may be in the form of pharmaceutically acceptable emulsions, syrups, elixirs, suspensions, slurries and solutions, which may contain an inactive diluent, such as water. Pharmaceutical formulations may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

For intranasal administration (e.g., to deliver compounds to the brain), or administration by inhalation (e.g., to deliver compounds through the lungs), the pharmaceutical formulations may be a solution, a spray, a dry powder, or aerosol containing any appropriate solvents and optionally other compounds such as, but not limited to, stabilizers, antimicrobial agents, antioxidants, pH modifiers, surfactants, bioavailability modifiers and combinations of these. Examples of intranasal formulations and methods of administration can be found in WO 01/41782, WO 00133813, WO 91/97947, U.S. Pat. Nos. 6,180,603, and 5,624,898. A propellant for an aerosol formulation may include compressed air, nitrogen, carbon dioxide, or a hydrocarbon based low boiling solvent. The compound or compounds of the instant invention are conveniently delivered in the form of an aerosol spray presentation from a nebulizer or the like.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Preferably, the oil or fatty acid is nonvolatile, including natural or synthetic oils, fatty acids, mono-, di- or tri-glycerides.

For injection, the pharmaceutical formulation may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these. The compounds may be formulated for parenteral administration by injection such as by bolus injection or continuous infusion. A unit dosage form for injection may be in ampoules or in multi-dose containers.

For rectal administration, the pharmaceutical formulations may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils may also be employed in the preparation of formulations of the soft gelatin type and suppositories. Water, saline, aqueous dextrose and related sugar solutions, and glycerols may be employed in the preparation of suspension formulations which may also contain suspending agents such as pectins, carbomers, methyl cellulose, hydroxypropyl cellulose or carboxymethyl cellulose, as well as buffers and preservatives.

Besides those representative dosage forms described above, pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

The formulations of the invention may be designed for to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations may be compressed into pellets or cylinders and implanted intramuscularly or subcutaneously as depot injections or as implants such as stents. Such implants may employ known inert materials such as silicones and biodegradable polymers.

A therapeutically effective dose refers to that amount of the compound that results in amelioration of symptoms. Specific dosages may be adjusted depending on conditions of disease, the age, body weight, general health conditions, sex, diet of the subject, dose intervals, administration routes, excretion rate, and combinations of drugs. Any of the above dosage forms containing effective amounts are well within the bounds of routine experimentation and therefore, well within the scope of the instant invention. A therapeutically effective dose may vary depending upon the route of administration and dosage form. The preferred compound or compounds of the instant invention is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

The present invention also provides methods of enhancing MC4-R activity in a human or non-human animal. The method comprises administering an effective amount of a compound, or composition, of the instant invention to said mammal or non-human animal. Effective amounts of the compounds of the instant invention include those amounts that activate MC4-R which are detectable, for example, by an assay described below in the illustrative Examples, or any other assay known by those skilled in the art that a detect signal transduction, in a biochemical pathway, through activation of G-protein coupled receptors, for example, by measuring an elevated cAMP level as compared to a control model. Accordingly, "activating" means the ability of a compound to initiate a detectable signal. Effective amounts may also include those amounts which alleviate symptoms of a MC4-R disorder treatable by activating MC4-R.

An MC4-R disorder, or MC4-R-mediated disease, which may be treated by those methods provided, include any biological disorder or disease in which MC4-R is implicated, or which inhibition of MC4-R potentiates a biochemical pathway that is defective in the disorder or disease state. Examples of such diseases are obesity, erectile disorders, cardiovascular disorders, neuronal injuries or disorders, inflammation, fever, cognitive disorders, type II diabetes, polycystic ovary disease, Syndrome X, complications from obesity and diabetes, and sexual behavior disorders. In a preferred embodiment, the instant invention provides compounds, compositions, and methods effective for reducing energy intake and body weight; reducing serum insulin and glucose levels; alleviating insulin resistance; and reducing serum levels of free fatty acids. Accordingly, the instant invention is particularly effective in treating those disorders or diseases associated with obesity or type II diabetes.

"Treating" within the context of the instant invention, therefore, means an alleviation of symptoms associated with a disorder or disease, or halt of further progression or worsening of those symptoms, or prevention or prophylaxis of the disease or disorder. For example, within the context of obesity, successful treatment may include an alleviation of symptoms or halting the progression of the disease, as measured by reduction in body weight, or a reduction in amount of food or energy intake. In this same vein, successful treatment of type I or type II diabetes may include an alleviation of symptoms or halting the progression of the disease, as measured by a decrease in serum glucose or insulin levels in, for example, hyperinsulinemic or hyperglycemic patients.

The present invention, thus generally described, will be understood more readily by reference to the following examples, which are provided by way of illustration and are not intended to be limiting of the present invention.

EXAMPLES

The following abbreviations are used throughout the Examples:
ACN:Acetonitrile
DCM:Dichloromethane
DIEA:Diisopropylethylamine
DM F: Dimethylformamide
DMSO:Dimethylsulfoxide
EDCl:1-Ethyl-3-(3'-dimethylaminopropyl)carbodiimide hydrochloride
HCl:Hydrochloric acid
HPLC:High Pressure Liquid Chromatography
KOH:Potassium hydroxide
MeOH:Methanol
PyBOP: Benzotriazole-1-yl-oxy-tris-pyrrolidino-phosphonium hexafluorophosphate
TFA:Trifluoroacetic acid
THF:Tetrahydrofuran
TMOF:Trimethylorthoformate Example 1

Preparation of (4-{[1-((3R)-3-methylpiperazinyl)(1Z)-2-aza-2-cyclohexylvinyl]amino}phenyl)-N-[2-(2,4-dichlorophenyl)ethyl]carboxamide Step 1. Preparation of [4-(azadiazomvinyl)phenyl]-N-[2-(2,4-dichlorophenyl)ethyl]carboxamide.

To a mixture of 2-(2,4-dichlorophenyl)ethylamine (20.2 mmol), 4-azidobenzoic acid (22.2 mmol) and EDCl (22.2 mmol) in THF was added DIEA (40.2 mmol) at room temperature. The mixture was stirred overnight and the THF was removed. The residue was diluted with ethyl acetate, washed with 1N HCl, brine, $NaHCO_3$ (sat.), and dried over $Na_2SO_4$ and concentrated to give a solid, which was purified on silica gel eluting with ethyl acetate/hexane (1:4) to give [4-(azadiazomvinyl)phenyl]-N-[2-(2,4-dichlorophenyl) ethyl]carboxamide (93%).

Step 2. Preparation of (4-{[1-((3R)-3-methylpiperazinyl)(1Z)-2-aza-2-cyclohexylvinyl]-amino}phenyl)-N-[2-(2,4-dichlorophenyl)ethyl]-carboxamide.

To a solution of [4-(azadiazomvinyl)phenyl]-N-[2-(2,4-dichlorophenyl)-ethyl]carboxamide (2.56 mmol) in THF was added triphenylphosphine (3.07 mmol) at room temperature. After 10 minutes, cyclohexyl isocyanate (3.07 mmol) was added. The solution was heated at 70° C. overnight. To the mixture was added (S)-2-methylpiperazine (5.12 mmol). After being heated at 70° C. for 2 hours, THF was removed. The residue was dissolved in 1N HCl and water, extracted with ether. The aqueous layer was treated with solid $NaHCO_3$, extracted with ethyl acetate. The combined ethyl acetate layers were dried over $Na_2SO_4$, and concentrated to give a residue, which was purified via RP-prep-HPLC to give (4-{[1-((3R)-3-methylpiperazinyl)(1Z)-2-aza-2-cyclohexylvinyl]amino}phenyl)-N-[2-(2,4-dichlorophenyl)ethyl]carboxamide as a free base. The base was treated with 1.1 equivalent of HCl (0.5N), dissolved in ACN/water, and lyophilized to give its mono HCl salt.

HPLC: 23.05 minutes
MS: MH+=516

Example 2

Preparation of (4-{[1-((3R)-3-methylpiperazinyl)(1Z)-2-aza-2-cyclohexylvinyl]amino}phenyl)-N-[2-(2,4-dichlorophenyl)ethyl]carboxamide on Solid Phase An aldehyde Sasrin resin (0.7 mmol/g, 3.5 mmol) was washed with TMOF. To the resin were added TMOF, 2-(2,4-dichlorophenyl)ethylamine (14.0 mmol) and NaH$_3$B(CN) (20 mmol) in THF. The mixture was shaken overnight, and washed with MeOH and DCM, dried in vacuo to give an amine resin. To the amine resin (2.1 mmol) in DMF was added 4-azidobenzoic acid (10.5 mmol), PyBOP (10.5 mmol) and DIEA (40 mmol). After being shaken overnight, the resin was washed with MeOH and DCM, dried in vacuo to an amide resin.

To the amide resin (1.0 g, 0.7 mmol) in THF was added triphenylphosphine (7 mmol) followed with cyclohexyl isocyanate. The mixture was heated at 70° C. for 5 hours, and washed with DCM and THF. (S)-2-methylpiperazine (20 mmol) and THF were added. The mixture was shaken at room temperature overnight, washed with DCM, MeOH and DCM, and dried in vacuo. The resin was treated with TFA for 2 hours. After being washed with DCM, the combined solution was concentrated, and purified via HPLC to give (4-{[1-((3R)-3-methylpiperazinyl)(1Z)-2-aza-2-cyclohexylvinyl]amino}phenyl)-N-[2-(2,4-dichlorophenyl)ethyl]carboxamide as its bis-trifluoroacetate salt.

HPLC: 23.05 minutes
MS: MH+=516

Example 3

Preparation of [4-({[(1E)-1-((3S)-3-methylpiperazinyl)-2-aza-2-cyclohexylvinyl]amino}methyl)phenyl]-N-[2-(2,4-dichlorophenyl)ethyl]carboxamide on Solid Phase An aldehyde Sasrin resin (0.7 mmol/g, 3.5 mmol) was washed with TMOF. To the resin were added TMOF, 2-(2,4-dichlorophenyl)ethylamine (14 mmol) and NaH$_3$B(CN) (1M in THF, 20 mmol). The mixture was shaken overnight, and washed with MeOH and DCM, dried in vacuo to give an amine resin.

To the amine resin (1.4 mmol) in DMF was added 4-bromomethylbenzoic acid (7.0 mmol), PyBOP (7 mmol) and DIEA (28 mmol). After being shaken for 3 hours, the resin was washed with MeOH and DCM, and DMSO. To the resin in DMSO was added sodium azide (14 mmol), and the mixture was shaken for 4 days, and washed with water, MeOH, DCM, water, MeOH, DCM and dried.

To the amide resin (0.14 mmol) in THF was added triphenylphosphine (0.382 mmol) followed with cyclohexyl isocyanate. The mixture was heated at 70° C. for 5 hours, and washed with DCM and THF. (S)-2-methylpiperazine (1 mmol) and THF were added. The mixture was heated at 70° C. overnight, washed with DCM, MeOH and DCM, treated with TFA for 2 hours. After being washed with DCM, the combined solution was concentrated, and purified via HPLC to give [4-({[(1 E)-1-((3S)-3-methylpiperazinyl)-2-aza-2-cyclohexylvinyl]amino}-methyl)phenyl]-N-[2-(2,4-dichlorophenyl)ethyl]carboxamide as its bis-trifluoroacetate salt.

HPLC: 24.07 minutes
MS: MH+=530

Example 4

Preparation of (4-{[(1Z)-2-aza-1-(cis-3,5-dimethylpiperazinyl)-2-cyclohexylvinyl]amino}phenyl)-N-[2-(2,4-dichlorophenyl)ethyl]carboxamide on Immobilized Triphenylphosphine Resin Step 1. Preparation of Immobilized {4-[aza(triphenylylidene)methyl]phenyl}-N-[2-(2,4-dichlorophenyl)ethyl]carboxamide.

To a suspension of triphenylphosphine resin (3 mmol/g, 30 mmol) in THF at 0° C. was added solid [4-(azadiazomvinyl)phenyl]-N-[2-(2,4-dichlorophenyl)-ethyl]carboxamide (30.0 mmol) in several portions. After 30 minutes, the ice-bath was removed. The mixture was stirred at room temperature for 3 hours, filtered and washed with DCM, and dried in vacuo to give immobilized {4-[aza(triphenylylidene)methyl]phenyl}-N-[2-(2,4-dichlorophenyl)ethyl]carboxamide.

Step 2. Preparation of (4-{[(1Z)-2-aza-1-(cis-3,5-dimethylpiperazinyl)-2-cyclohexyl-vinyl]amino}phenyl)-N-[2-(2,4-dichlorophenyl)ethyl]-carboxamide.

To polymer-bound phosphine-imine (1.5 mmol/g, 0.15 mmol) in THF in a vial was added cyclohexylisocyanate (0.15 mmol). The vial was capped and heated at 70° C. overnight. After being cooled to room temperature, cis-2,6-dimethylpiperazine (0.18 mmol, 1.2 equivalents) was added. The vial was capped and heated at 70° C. for 2 hours, filtered and washed with DCM. The combined filtrates were concentrated, and purified on HPLC to give (4-{[(1Z)-2-aza-1-(cis-3,5-dimethylpiperazinyl)-2-cyclohexylvinyl]amino}phenyl)-N-[2-(2,4-dichlorophenyl)ethyl]-carboxamide as its bis-trifluoroacetate salt.

HPLC: 23.79 minutes
MS: MH+=530

Example 5

Preparation of (4-{[1-((3S)-3-methylpiperazinyl)(1Z)-2-aza-2-cycloheptylvinyl]amino}phenyl)-N-[2-(2,4-dichlorophenyl)ethyl]carboxamide Step 1. Preparation of Cycloheptanisocyanate.

To a cold solution of cycloheptylamine (221 mmol) and charcoal (catalytic) in ethyl acetate at −10° C. was added a pre-cooled solution of diphosgene (265.0 mmol) in ethyl acetate dropwise via addition funnel. After the addition, the reaction was heated to reflux overnight, and filtered through a Celite plug. The solution was concentrated to give a thick oil, which was distilled to yield cycloheptanisocyanate as a clear liquid (67%).

Step 2. Preparation of (4-{[1-((3S)-3-methylpiperazinyl)(1Z)-2-aza-2-cycloheptyl vinyl]amino}phenyl)-N-[2-(2,4-dichlorophenyl)ethyl]-carboxamide.

To the polymer bound phosphine imine resin (0.194 mmol) in THF was added cycloheptanisocyanate (194 mmol) and the reaction was heated at 70° C. overnight. To the reaction was added (S)-2-methylpiperazine (0.23 mmol), and the reaction was heated for 2 hours at 70° C. The resin was filtered and washed with dichloromethane twice. The filtrate solution was concentrated, and purified via HPLC to give (4-{[1-((3S)-3-methylpiperazinyl)(1Z)-2-aza-2-cycloheptylvinyl]-amino}phenyl)-N-[2-(2,4-dichlorophenyl)ethyl]carboxamide as a white powder.

HPLC: 23.18 minutes
MS: MH+=530

Example 6

Preparation of (4-{[(1Z)-2-aza-1-(3,5-dimethylpiperazinyl)-2-cycloheptyl vinyl]amino}phenyl)-N-[2-(2,4-dichlorophenyl)ethyl]carboxamide To the solution of polymer bound phosphine imine resin (0.21 mmol) in THF (2 mL) was added cycloheptylisocyanate (0.21 mmol). The reaction was heated at 70° C. overnight. To the reaction was added 2,6-dimethylpiperazine (0.25 mmol) and the reaction was heated for 2 hours at 70° C. The resin was filtered and washed with dichloromethane twice. The filtrate solution was concentrated, and purified via HPLC to give (4-{[(1Z)-2-aza-1-(3,5-dimethylpiperazinyl)-2-cycloheptylvinyl]amino}phenyl)-N-[2-(2,4-dichloro-phenyl)ethyl]carboxamide as a white powder.

HPLC: 23.70 minutes

MS: MH+=544.3

Example 7

Preparation of (4-{[1-((3R)-3-methylpiperazinyl)(1Z)-2-aza-2-(2-methylcyclohexyl)vinyl]amino}phenyl)-N-[2-(2,4-dichlorophenyl)ethyl]carboxamide Step 1. Preparation of {4-[aza(triphenylylidene)methyl]phenyl}-N-[2-(2,4-dichloro-phenyl)ethyl]carboxamide.

To a solution of [4-(azadiazomvinyl)phenyl]-N-[2-(2,4-dichlorophenyl)ethyl]carboxamide (0.18 mmol) in THF (2 mL) was added triphenylphosphine (0.21 mmol), and the mixture was stirred at room temperature for 10 minutes.

Step 2. Preparation of (4-{[1-((3R)-3-methylpiperazinyl)(1Z)-2-aza-2-(2-ethyl-cyclo-hexyl)vinyl]amino}phenyl)-N-[2-(2,4-dichlorophenyl)ethyl]-carboxamide.

To the {4-[aza(triphenylylidene)methyl]phenyl}-N-[2-(2,4-dichlorophenyl)ethyl]carboxamide solution was added 2-methylcyclohexyl isocyanate (0.25 mmol). The solution was heated at 70° C. overnight. To half of the carboimide solution was added a THF solution of (S)-2-methylpiperazine (0.3 mmol). After being heated at 70° C. for 2 hours, the residue was subjected to HPLC purification to give (4-{[1-((3R)-3-methyl piperazinyl)(1Z)-2-aza-2-(2-methylcyclohexyl)-vinyl]amino}phenyl)-N-[2-(2,4-dichlorophenyl)ethyl]carboxamide as its TFA salt.

HPLC: 24.43 minutes

MS: MH+=530

Example 8

Preparation of (4-{[(1Z)-2-aza-1-(3,5-dimethylpiperazinyl)-2-(2-methylcyclohexyl)vinyl]amino}phenyl)-N-[2-(2,4-dichlorophenyl)ethyl]carboxamide To a solution of [4-(azadiazomvinyl)phenyl]-N-[2-(2,4-dichlorophenyl)-ethyl]carboxamide (2.0 mmol) in THF was added triphenylphosphine (2.2 mmol), and the resulting mixture was stirred at room temperature for 10 minutes. To the {4-[aza(triphenylylidene)methyl]phenyl}-N-[2-(2,4-dichlorophenyl)-ethyl]carboxamide solution was added 2-methylcyclohexyl isocyanate (2.4 mmol). The solution was heated at 70° C. overnight. To the carboimide solution was added 2,6-dimethylpiperazine (2.4 mmol). After being heated at 70° C. for 2 hours, the residue was subjected to HPLC purification to give (4-{[(1Z)-2-aza-1-(3,5-dimethylpiperazinyl)-2-(2-methylcyclohexyl)-vinyl]amino}phenyl)-N-[2-(2,4-dichlorophenyl)ethyl]carboxamide as its TFA salt.

HPLC: 24.00 minutes

MS: MH+=544

Example 9

Preparation of [4-({1-((3S)-3-methylpiperazinyl)(1Z)-2-aza-2-[4-(tert-butyl)cyclohexyl]vinyl}amino)phenyl]-N-[2-(2,4-dichlorophenyl)ethyl]carboxamide Step 1. Preparation of 4-(tert-butyl)cyclohexanisocyanate.

A pre-cooled solution of diphosgene (168.0 mmol) in ethyl acetate was added dropwise via addition funnel into the cold solution of 4-(t-butyl)cyclohexylamine (140.0 mmol) and charcoal (catalytic) in ethyl acetate at −10C. After the addition, the reaction was heated to reflux overnight, and filtered through a Celite plug. The solution was concentrated to give a thick oil, which was distilled in vacuo to yield 4-(tert-butyl)cyclohexanisocyanate as a clear liquid (48%).

Step 2. Preparation of [4-({1-((3S)-3-methylpiperazinyl)(1Z)-2-aza-2-[4-(tert-butyl)cyclohexyl]vinyl}amino)phenyl]-N-[2-(2,4-dichlorophenyl)-ethyl]carboxamide.

To the polymer bound phosphineimine resin (0.150 mmol) in THF was added 4-(tert-butyl)cyclohexanisocyanate (0.15 mmol) and the reaction was heated at 70° C. overnight. To the reaction was added (S)-2-methylpiperazine (0.18 mmol), and reaction was heated for 2 hours at 70° C. The resin was filtered and washed with dichloromethane twice. The filtrate solution was concentrated, and purified via HPLC to give [4-({1-((3S)-3-methylpiperazinyl)(1Z)-2-aza-2-[4-(tert-butyl)cyclohexyl]-vinyl}amino)-phenyl]-N-[2-(2,4-dichlorophenyl)ethyl]-carboxamide as a white powder.

HPLC: 26.82 minutes

MS: MH+=572

Example 10

Preparation of [4-({(1Z)-2-aza-2-[4-(tert-butyl)cyclohexyl]-1-(3,5-dimethylpiperazinyl)vinyl}amino)phenyl]-N-[2-(2,4-dichlorophenyl)ethyl]carboxamide To the polymer bound phosphineimine resin (0.150 mmol) in THF was added 4-(tert-butyl)cyclohexanisocyanate (0.15 mmol). The reaction was then heated at 70° C. overnight. To the reaction was added 2,6-dimethylpiperazine (0.18 mmol), and the reaction was heated for 2 hours at 70° C. The resin was filtered and washed with dichloromethane twice. The filtrate solution was concentrated, and purified via HPLC to give [4-({(1Z)-2-aza-2-[4-(tert-butyl)cyclohexyl]-1-(3,5-dimethylpiperazinyl)vinyl}amino)phenyl]-N-[2-(2,4-dichlorophenyl)-ethyl]carboxamide as a white powder.

HPLC: 27.05 minutes

MS: MH+=586.5

Example 11

Preparation of (4-{[1-((3S)-3-methylpiperazinyl)(1Z)-2-aza-2-(3,3,5-trimethylcyclohexyl)vinyl]amino}phenyl)-N-[2-(2,4-dichlorophenyl)ethyl]carboxamide Step 1. Preparation of 3,3,5-trimethylcyclohexanisocyanate.

A pre-cooled solution of diphosgene (178.3 mmol) in ethyl acetate was added dropwise via addition funnel into the cold solution of 3,3,5-trimethylcyclohexylamine (148.6 mmol) and charcoal (catalytic) in ethyl acetate at −10° C. After the addition, the reaction was heated to reflux overnight, and filtered through a Celite plug. The solution was concentrated to give a thick oil, which was distilled in vacuo to yield 3,3,5-trimethylcyclohexanisocyanate as a clear liquid (56%).

Step 2. Preparation of (4-{[1-((3S)-3-methylpiperazinyl)(1Z)-2-aza-2-(3,3,5-trimethyl-cyclohexyl)vinyl]amino}phenyl)-N-[2-(2,4-dichlorophenyl)-ethyl]carboxamide.

To the polymer bound phosphineimine resin (0.15 mmol) in THF was added 3,3,5-trimethylcyclohexanisocyanate (0.15 mmol). The reaction was heated at 70° C. overnight. To the reaction was added (S)-2-methylpiperazine (0.18 mmol), and reaction was heated for 2 hours at 70° C. The resin was filtered and washed with dichloromethane twice. The filtrate solution was concentrated, and purified via HPLC to give (4-{[1-((3S)-3-methylpiperazinyl)(1Z)-2-aza-2-(3,3,5-trimethylcyclohexyl)vinyl]amino}phenyl)-N-[2-(2,4-dichlorophenyl)-ethyl]carboxamide as a white powder.

HPLC: 25.62 minutes
MS: MH+=558.5

Example 12

Preparation of (4{[(1Z)-2-aza-1-(3,5-dimethylpiperazinyl)-2-(3,3,5-trimethylcyclohexyl)vinyl]amino}phenyl)-N-[2-(2,4-dichlorophenyl)ethyl]carboxamide To the polymer bound phosphineimine resin (0.150 mmol) in THF was added 3,3,5-trimethylcyclohexanisocyanate (0.15 mmol) and the reaction was heated at 70° C. overnight. To the reaction was added 2,6-dimethylpiperazine (0.18 mmol), and the reaction was heated for 2 hours at 70° C. The resin was filtered and washed with dichloromethane twice. The filtrate solution was concentrated, and purified via HPLC to give (4-{[(1Z)-2-aza-1-(cis-3,5-dimethylpiperazinyl)-2-(3,3,5-trimethylcyclohexyl)vinyl]-amino}phenyl)-N-[2-(2,4-dichlorophenyl)ethyl]carboxamide as a white powder.

HPLC: 25.74 minutes
MS: MH+=572.5

Example 13

Preparation of (4-{[1-((3S)-3-methylpiperazinyl)(1Z)-2-aza-2-cyclohex-3-enylvinyl]amino}phenyl)-N-[2-(2,4-dichlorophenyl)ethyl]carboxamide Step 1. Preparation of cyclohex-3-en-isocyanate.

A solution of 3-cyclohexenylcarboxylic acid (1 mmol), diphenylphosphoryl azide (1.2 mmol) and triethylamine (2.5 mmol) in toluene was heated at 100° C. for 9 hours.

Step 2. Preparation of [4-(1,3-diaza-3-cyclohex-3-enylpropa-1,2-dienyl) phenyl]-N-[2-(2,4-dichlorophenyl)ethyl]carboxamide.

To the isocyanate solution prepared above was added immobilized [4-(azadiazomvinyl)phenyl]-N-[2-(2,4-dichlorophenyl)ethyl]carboxamide on Sasrin resin (0.24 mmol). The mixture was heated at 70° C. for 6 hours, and then washed with DCM.

Step 3. Preparation of (4-{[1-((3S)-3-methylpiperazinyl)(1Z)-2-aza-2-cyclohex-3-enylvinyl]amino}phenyl)-N-[2-(2,4-dichlorophenyl)ethyl]carboxamide.

To the imine resin in THF was added a THF solution of (S)-2-methylpiperazine (0.5 mmol). After being heated at 70° C. for 2 hours, the resin was washed with MeOH/DCM, DCM, and treated with TFA for 2 hours. The filtrate was concentrated and subjected to HPLC purification to give (4-{[1-((3S)-3-methylpiperazinyl)(1Z)-2-aza-2-cyclohex-3-enylvinyl]amino}phenyl)-N-[2-(2,4-dichlorophenyl)ethyl]carboxamide as its TFA salt.

HPLC: 22.70 minutes
MS: MH+=514

Example 14

Preparation of (4-{[(1Z)-2-aza-1-(3,5-dimethylpiperazinyl)-2-cyclohex-3-enylvinyl]amino}phenyl)-N-[2-(2,4-dichlorophenyl)ethyl]carboxamide To the [4-(1,3-diaza-3-cyclohex-3-enylpropa-1,2-dienyl)phenyl]-N-[2-(2,4-dichlorophenyl)ethyl]carboxamide resin in THF (2 mL) was added a THF solution of 2,6-dimethylpiperazine (0.5 mmol). After being heated at 70° C. for 2 hours, the resin was washed with MeOH/DCM (5×), DCM (2×), and treated with TFA for 2 hours. The filtrate was concentrated and subjected to HPLC purification to give (4-{[(1Z)-2-aza-1-(cis-3,5-dimethylpiperazinyl)-2-cyclohex-3-enylvinyl]amino}phenyl)-N-[2-(2,4-dichlorophenyl)ethyl]carboxamide as its TFA salt.

HPLC: 23.18 minutes
MS: MH+=528

Example 15

Preparation of (4-{[(1Z)-2-aza-1-(cis-3,5-dimethylpiperazinyl)-3,3-dimethyl but-1-enyl]amino}phenyl)-N-[2-(2,4-dichlorophenyl)ethyl]carboxamide To a solution of {4-[aza(triphenylylidene)methyl]phenyl}-N-[2-(2,4-dichlorophenyl)-ethyl]carboxamide (0.05 mmol), was added t-butylisocyanate (14 μL, 0.12 mmol). The solution was heated at 70° C. overnight. To the solution was added a THF solution of 2,6-dimethylpiperazine (1 M, 0.1 mL, 0.1 mmol). After being heated at 70° C. for 2 hours, the solution was subjected to HPLC purification to give (4-{[(1 Z)-2-aza-1-(cis-3,5-dimethylpiperazinyl)3,3-dimethyl but-1-enyl]amino}phenyl)-N-[2-(2,4-dichlorophenyl)ethyl]carboxamide as its TFA salt.

HPLC: 27.05 minutes
MS: MH+=504

Example 16

Preparation of (4-{[1-((3S)-3-methylpiperazinyl)(1Z)-2-aza-3-cyclohexylprop-1-enyl]amino}phenyl)-N-[2-(2,4-dichlorophenyl)ethyl]carboxamide Step 1. Preparation of [4-(1,3-diaza-4-cyclohexylbuta-1,2-dienyl)phenyl]-N-[2-(2,4-dichlorophenyl)ethyl]carboxamide.

To a {4-[aza(triphenylylidene)methyl]phenyl}-N-[2-(2,4-dichlorophenyl)ethyl]carboxamide solution (0.15 mmol) was added cyclohexylmethylthioisocyanate (0.18 mmol). The solution was heated at 80° C. overnight, and used without further purification.

Step 2. Preparation of (4-{[1-((3S)-3-methylpiperazinyl)(1Z)-2-aza-3-cyclohexylprop-1-enyl]amino}phenyl)-N-[2-(2,4-dichloro phenyl)ethyl]carboxamide.

To the [4-(1,3-diaza-4-cyclohexylbuta-1,2-dienyl)phenyl]-N-[2-(2,4-dichlorophenyl)ethyl]carboxamide solution (0.075 mmol) was added a THF solution of (S)-2-methylpiperazine (0.15 mmol). After being heated at 70° C. for 2 hours, the solution was subjected to HPLC purification to give (4-{[1-((3S)-3-methylpiperazinyl)(1Z)-2-aza-3-cyclohexylprop-1-enyl]amino}phenyl)-N-[2-(2,4-dichlorophenyl)ethyl]carboxamide as its TFA salt.

HPLC: 24.26 minutes
MS: MH+=530

Example 17

Preparation of (4-{[(1Z)-2-aza-1-(3,5-dimethylpiperazinyl)-3-cyclohexylprop-1-enyl]amino}phenyl)-N-[2-(2,4-dichlorophenyl)ethyl]carboxamide To the [4-(1,3-diaza-4-cyclohexylbuta-1,2-dienyl)phenyl]-N-[2-(2,4-dichloro-phenyl)ethyl]carboxamide solution (0.075 mmol) was added a THF solution of 2,6-dimethylpiperazine (0.15 mmol). After being heated at 70° C. for 2 hours, the solution was subjected to HPLC purification to give (4-{[(1Z)-2-aza-1-(3,5-dimethylpiperazinyl)-3-cyclohexylprop-1-enyl]amino}phenyl)-N-[2-(2,4-dichlorophenyl)ethyl]carboxamide as its TFA salt.

HPLC: 24.68 minutes
MS: MH+=544

Example 18

Preparation of (4-{[1-((3S)-3-methylpiperazinyl)(1Z)-2-aza-2-cyclooctylvinyl]amino}phenyl)-N-[2-(2,4-dichlorophenyl)ethyl]carboxamide Step 1. Preparation of Cyclooctanisocyanate.

A pre-cooled solution of diphosgene (236 mmol) in ethyl acetate was added dropwise via an addition funnel into the cold solution of cyclooctylamine (196 mmol) and charcoal (catalytic) in ethyl acetate at −10° C. After the addition, the reaction was heated to reflux overnight, and filtered through a Celite plug. The solution was concentrated to give a thick oil, which was distilled in vacuo to yield cyclooctanisocyanate (46%) as a clear liquid.

Step 2. Preparation of (4-{[1-((3S)-3-methylpiperazinyl)(1Z)-2-aza-2-cyclooctylvinyl]-amino}phenyl)-N-[2-(2,4-dichlorophenyl)ethyl]carboxamide.

To the polymer bound phosphineimine resin (0.15 mmol) in THF was added cyclooctanisocyanate (0.15 mmol) and the reaction was heated at 70° C. overnight. To the reaction was added (S)-2-methylpiperazine (0.18 mmol), and reaction was heated for 2 hours at 70° C. The resin was filtered and washed with dichloromethane twice. The filtrate solution was concentrated, and purified via HPLC to give (4-{[1-((3S)-3-methylpiperazinyl)(1Z)-2-aza-2-cyclooctylvinyl]amino}phenyl)-N-[2-(2,4-dichlorophenyl)ethyl]carboxamide as a white powder.

HPLC: 24.59 minutes
MS: MH+=544

Example 19

Preparation of (4-{[(1Z)-2-aza-1-(3,5-dimethylpiperazinyl)-2-cyclooctylvinyl]amino}phenyl)-N-[2-(2,4-dichlorophenyl)ethyl]carboxamide To the polymer bound phosphineimine resin (0.150 mmol) in THF was added cyclooctanisocyanate (0.15 mmol) and the reaction was heated at 70° C. overnight. To the reaction was added 2,6-dimethylpiperazine (0.18 mmol), and the reaction was heated for 2 hours at 70° C. The resin was filtered and washed with dichloromethane twice. The filtrate solution was concentrated, and purified via HPLC to give (4-{[(1Z)-2-aza-1-(3,5-dimethylpiperazinyl)-2-cyclooctylvinyl]amino}phenyl)-N-[2-(2,4-dichlorophenyl)ethyl]carboxamide as a white powder.

HPLC: 24.80 minutes
MS: MH+=558.5

Example 20

Preparation of (4-{[1-((3S)-3-methylpiperazinyl)(1Z)-2-aza-2-(4-methylcyclohexyl)vinyl]amino}phenyl)-N-[2-(2,4-dichlorophenyl)ethyl]carboxamide Step 1. Preparation 4-methylcyclohexanisocyanate.

A pre-cooled solution of diphosgene (530 mmol) in ethyl acetate was added dropwise via addition funnel into the cold solution of 4-methylcyclohexylamine (442 mmol) and charcoal (catalytic) in ethyl acetate at −10° C. After the addition, the reaction was heated to reflux overnight, and filtered through a Celite plug. The solution was concentrated to give a thick oil, which was distilled in vacuo to yield (48%) as a clear liquid.

Step 2. Preparation of (4-{[1-((3S)-3-methylpiperazinyl)(1Z)-2-aza-2-(4-methylcyclo-hexyl)vinyl]amino}phenyl)-N-[2-(2,4-dichlorophenyl)-ethyl]carboxamide.

To the polymer bound phosphineimine resin (0.15 mmol) in THF was added 4-methylcyclohexanisocyanate (0.15 mmol) and the reaction was heated at 70° C. overnight. To the reaction was added (S)-2-methylpiperazine (0.18 mmol), and reaction was heated for 2 hours at 70° C. The resin was filtered and washed with dichloromethane twice. The filtrate solution was concentrated, and purified via HPLC to give (4-{[1-((3S)-3-methylpiperazinyl)(1Z)-2-aza-2-(4-methylcyclohexyl) vinyl]amino}phenyl)-N-[2-(2,4-dichlorophenyl)ethyl]carboxamide as a white powder.

HPLC: 23.97 minutes
MS: MH+=530.5

Example 21

Preparation of (4-{[(1Z)-2-aza-1-(3,5-dimethylpiperazinyl)-2-(4-methylcyclohexyl)vinyl]amino}phenyl)-N-[2-(2,4-dichlorophenyl)ethyl]carboxamide To the polymer bound phosphineimine resin (0.150 mmol) in THF was added 4-methylcyclohexanisocyanate (0.15 mmol), and the reaction was heated at 70° C. overnight. To the reaction was added 2,6-dimethylpiperazine (0.18 mmol), and reaction was heated for 2 hours at 70° C. The resin was filtered and washed with dichloromethane twice. The filtrate solution was concentrated, and purified via HPLC to give (4-{[(1Z)-2-aza-1-(3,5-dimethylpiperazinyl)-2-(4-methylcyclohexyl) vinyl]amino}phenyl)-N-[2-(2,4-dichlorophenyl)ethyl]-carboxamide (a mixture of cis and trans isomers) as a white powder.

HPLC: 24.28 minutes (32.6%) and 24.46 minutes (67.3%)
MS: MH+=544.5

Example 22

Preparation of [4-(1,3-diaza-3-bicyclo[2.2.1]hept-2-ylpropa-1,2-dienyl)phenyl]-N-[2-(2,4-dichlorophenyl)ethyl]carboxamide To a solution of {4-[aza(triphenylylidene)methyl]phenyl}-N-[2-(2,4-dichlorophenyl)ethyl]carboxamide (0.1 mmol) was added bicyclo[2.2.1]heptan-2-isothiocyanate (0.12 mmol). The mixture was heated at 90° C. for 24 hours to give a phosphorane imine solution.

Example 23

Preparation of (4-{[1-((3S)-3-methylpiperazinyl)(1Z)-2-aza-2-bicyclo[2.2.1]hept-2-ylvinyl]amino}phenyl)-N-[2-(2,4-dichlorophenyl)ethyl]carboxamide To half of the phosphorane imine solution prepared from Example 22 was added (S)-2-methylpiperazine (0.2 mmol). The reaction was heated at 70° C. for 2 hours. The mixture was concentrated and subjected to HPLC purification to give (4-{[1-((3S)-3-methyl piperazinyl)(1Z)-2-aza-2-bicyclo[2.2.1]hept-2-ylvinyl]-amino}phenyl)-N-[2-(2,4-dichlorophenyl)ethyl]carboxamide as its TFA salt.

HPLC: 23.26 minutes

MS: MH+=528

Example 24

Preparation of (4-{[(1Z)-2-aza-2-bicyclo[2.2.1]hept-2-yl-1-(3,5-dimethylpiperazinyl)vinyl]amino}phenyl)-N-[2-(2,4-dichlorophenyl)ethyl]carboxamide To half of the phosphorane imine solution prepared above (Example 22) was added 2,6-dimethylpiperazine (1 M in THF, 0.2 mL, 0.2 mmol). The reaction was heated at 70° C. for 2 hours. The mixture was concentrated and subjected to HPLC purification to give (4-{[(1Z)-2-aza-2-bicyclo[2.2.1]hept-2-yl-1-(3,5-dimethylpiperazinyl)vinyl]amino}phenyl)-N-[2-(2,4-dichlorophenyl)ethyl]carboxamide as its TFA salt.

HPLC: 23.71 minutes

MS: MH+=542

Example 25

Preparation of (4-{[2-(trans-2-ethylcyclohexyl)(1Z)-2-aza-1-(3,5-dimethylpiperazinyl)vinyl]amino}phenyl)-N-[2-(2,4-dichlorophenyl)ethyl]carboxamide Step 1. Preparation of 2-ethyl-1-(hydroxyimino)cyclohexane.

To a solution of 2-ethylcyclohexanone (104.3 mmol) in water and ethanol, and sodium acetate (125.1 mmol) were added hydroxylamine hydrochloride (156.4 mmol), the reaction was heated at 70° C. overnight. The ethanol was removed under reduced pressure, and the reaction mixture was dissolved in water. The aqueous layer was extracted with ether, and the combined organic extracts were washed with brine, dried over sodium sulfate, and concentrated to give 2-ethyl-1-(hydroxyimino)cyclohexane (52%) as a thick oil.

Step 2. Preparation of 2-ethylcyclohexylamine.

To the solution of 2-ethyl-1-(hydroxyimino)cyclohexane (6.8 g, 48.5 mmol) in ethanol (75 mL) were added sodium pieces (about 8.0 g) in portions, and the reaction was heated to reflux at 110° C. overnight. More sodium pieces were added, and the reaction was stirred for another 6 hours. The reaction was treated with concentrated HCl (12 M, 4.0 mL) in water (25 mL). Ethanol was removed in vacuo. The aqueous layer was washed with ether (10 mL), and treated with aqueous KOH (25 mL) and extracted with ether (3×20 mL). The combined organic extracts were washed with brine (20 mL), dried over sodium sulfate, and concentrated in vacuo to give 2-ethylcyclohexylamine as an off-white oil.

Step 3. Preparation of 2-ethylcyclohexylisocyanate.

To a solution of 2-ethylcyclohexylamine (0.61 mmol) in methanol was added HCl (4.0 M in dioxane, 0.152 mL), and concentrated to give a residue. Phosgene solution (20% in toluene, 6.0 mL) was added, and the reaction was heated at 110° C. overnight. Toluene and excess of phosgene were removed in vacuo to give a residue.

Step 4. Preparation of (4-{[2-(trans-2-ethylcyclohexyl)(1Z)-2-aza-1-(3,5-dimethylpiperazinyl)vinyl]amino}phenyl)-N-[2-(2,4-dichlorophenyl) ethyl]carboxamide To a solution of [4-(azadiazomvinyl)phenyl]-N-[2-(2,4-dichlorophenyl)ethyl]carboxamide (0.785 mmol) in THF was added triphenylphosphine (0.785 mmol). The solution was stirred for 10 minutes and added to trans-2-ethylcyclohexylisocyanate as prepared above. The solution was heated at 70° C. overnight. 2,6-dimethylpiperazine (0.785 mmol) was added, and the reaction was heated for 3 hours at 70° C. The solution was concentrated, and purified via HPLC to give (4-{[2-(trans-2-ethylcyclohexyl)(1Z)-2-aza-1-(3,5-dimethylpiperazinyl)vinyl]amino}phenyl)-N-[2-(2,4-dichlorophenyl)ethyl]-carboxamide as a white powder.

HPLC: 24.60 minutes

MS: MH+=558.3

Example 26

Preparation of (4-{[1-((3S)-3-methylpiperazinyl)(1Z)-2-aza-2-(2-cyclohexylcyclohexyl)vinyl]amino}phenyl)-N-[2-(2,4-dichlorophenyl)ethyl]carboxamide Step 1. Preparation of 2-cyclohexylcyclohexanisocyanate.

A solution of 2-cyclohexylcyclohexylamine (1.0 mmol) in methanol was treated with HCl (4 N in dioxane, 0.5 mL, 2 mmol), and concentrated to give a residue, which was treated with phosgene, and heated at 110° C. overnight. Toluene and excess of phosgene were removed in vacuo to give a residue.

Step 2. Preparation of (4-{[1-((3S)-3-methylpiperazinyl)(1Z)-2-aza-2-(2-cyclohexylcyclohexyl)-vinyl]amino}phenyl)-N-[2-(2,4-dichlorophenyl)ethyl]carboxamide.

To the isocyanate residue was added a solution of {4-[aza(triphenylylidene)methyl]phenyl}-N-[2-(2,4-dichlorophenyl)-ethyl]carboxamide prepared in situ from [4-(azadiazomvinyl)phenyl]-N-[2-(2,4-dichlorophenyl)-ethyl]carboxamide (0.6 mmol) and triphenylphosphine (0.6 mmol) in THF (10 mL). The solution was heated for 70° C. overnight. To half of the solution was added (S)-2-methylpiperazine (0.5 mmol) and the reaction was heated at 70° C. for 2 hours. The mixture was concentrated and subjected to HPLC purification to give (4-{[1-((3S)-3-methylpiperazinyl)(1Z)-2-aza-2-(2-cyclohexylcyclohexyl)-vinyl]amino}phenyl)-N-[2-(2,4-dichlorophenyl)ethyl]carboxamide as its TFA salt.

HPLC: 27.79 minutes

MS: MH+=598

Example 27

Preparation of (4-{[(1Z)-2-aza-1-(3,5-dimethylpiperazinyl)-2-(2-cyclohexylcyclohexyl)vinyl]amino}phenyl)-N-[2-(2,4-dichlorophenyl)ethyl]carboxamide To half of the {4-[1,3-diaza-3-(2-cyclohexylcyclohexyl)propa-1,2-dienyl]phenyl}-N-[2-(2,4-dichlorophenyl)ethyl]carboxamide solution prepared above was added 2,6-dimethylpiperazine (0.5 mmol), and the mixture was heated at 70° C. for 2 hours. The mixture was concentrated and subjected to HPLC purification to give (4-{[(1Z)-2-aza-1-(3,5-dimethylpiperazinyl)-2-(2-cyclohexylcyclohexyl)

vinyl]-amino}phenyl)-N-[2-(2,4-dichlorophenyl)ethyl]carboxamide as its TFA salt.

HPLC: 28.52 minutes
MS: MH+=612

Example 28

Preparation of (4-{[1-((3S)-3-methylpiperazinyl)(1Z)-2-aza-2-(2-methoxycyclohexyl)vinyl]amino}phenyl)-N-[2-(2,4-dichlorophenyl)ethyl]carboxamide Step 1. Preparation of 1-(hydroxyimino)-2-methoxycyclohexane.

A mixture of 2-methoxycyclohexanone (39.0 mmol), hydroxylamine hydrochloride (72 mmol), and sodium acetate (48.8 mmol) in ethanol and water was heated at 70° C. overnight. Ethanol was removed, and the residue was dissolved in water and ethyl acetate. The aqueous layer was extracted with ethyl acetate. The combined organic layers were washed with brine, dried, and concentrated to give 1-(hydroxyimino)-2-methoxycyclohexane.

Step 2. Preparation of 2-methoxycyclohexylamine.

A mixture of 1-(hydroxyimino)-2-methoxycyclohexane (1.05 mmol) and Raney Nickel (0.5 g) in ethanol (30 mL) was hydrogenated (90 psi) at room temperature for 2 days. The mixture was filtered through a pad of Celite, washed with MeOH, and concentrated. The residue was dissolved in MeOH, treated with HCl (4 N in dioxane, 4 mmol), and concentrated to give 2-methoxycyclohexylamine hydrochloride.

Step 3. Preparation of 2-methoxycyclohexanisocyanate.

A mixture of methoxycyclohexylamine hydrochloride (0.84 mmol) and a phosgene solution (20% in toluene) was heated at 110° C. overnight. Toluene and excess phosgene were removed in vacuo to give a residue.

Step 4. Preparation of (4-{[1-((3S)-3-methylpiperazinyl)(1Z)-2-aza-2-(2-methoxycyclohexyl)vinyl]amino}phenyl)-N-[2-(2,4-dichlorophenyl)ethyl]carboxamide.

To the isocyanate residue was added a solution of {4-[aza(triphenylylidene)methyl]phenyl}-N-[2-(2,4-dichlorophenyl)-ethyl]carboxamide prepared in situ from [4-(azadiazomvinyl)phenyl]-N-[2-(2,4-dichlorophenyl)-ethyl]carboxamide (0.3 mmol) and triphenylphosphine (0.3 mmol) in THF. The solution was heated for 70° C. overnight. To half of the solution was added (S)-2-methylpiperazine (26 mg, 0.25 mmol), and the mixture was heated at 70° C. for 2 hours. The mixture was concentrated and subjected to HPLC purification to give (4-{[1-((3S)-3-methylpiperazinyl)(1Z)-2-aza-2-(2-methoxycyclohexyl)vinyl]amino}-phenyl)-N-[2-(2,4-dichlorophenyl)ethyl]carboxamide (a mixture of cis and trans isomers) as its TFA salt.

HPLC: 23.10 and 23.25 minutes
MS: MH+=546

Example 29

Preparation of (4-{[(1Z)-2-aza-1-(3,5-dimethylpiperazinyl)-2-(2-methoxycyclohexyl)vinyl]amino}phenyl)-N-[2-(2,4-dichlorophenyl)ethyl]carboxamide To half the {4-[1,3-diaza-3-(2-methoxycyclohexyl)propa-1,2-dienyl]phenyl}-N-[2-(2,4-dichlorophenyl)ethyl]carboxamide solution prepared above was added 2,6-dimethylpiperazine (28 mg, 0.25 mmol), and the mixture was heated at 70° C. for 2 hours. The mixture was concentrated and subjected to HPLC purification to give (4-{[(1Z)-2-aza-1-(3,5-dimethylpiperazinyl)-2-(2-methoxycyclohexyl)vinyl]amino}phenyl)-N-[2-(2,4-dichlorophenyl)ethyl]carboxamide (a mixture of cis and trans isomers) as its TFA salt.

HPLC: 23.44 and 23.66 minutes
MS: MH+=560

Example 30

Preparation of (4-{[(1Z)-2-aza-1-(cis-3,5-dimethylpiperazinyl)-2-perhydro-2H-pyran-4-ylvinyl]amino}phenyl)-N-[2-(2,4-dichlorophenyl)ethyl]carboxamide Step 1. Preparation of 4-(hydroxyimino)-3,5,6-trihydro-2H-pyran.

A mixture of 3,5,6-trihydro-2H-pyran-4-one (50 mmol), hydroxylamine hydrochloride (72 mmol), and sodium acetate (61 mmol) in ethanol was heated at 70° C. overnight. Ethanol was removed in vacuo. The residue was dissolved in water and ethyl acetate. The aqueous layer was extracted with ethyl acetate. The combined organic layers were washed with brine, dried over $Na_2SO_4$, and concentrated to give 4-(hydroxyimino)-3,5,6-trihydro-2H-pyran (88%).

Step 2. Preparation of perhydro-2H-pyran-4-ylamine Hydrochloride.

A mixture of 4-(hydroxyimino)-3,5,6-trihydro-2H-pyran (43.4 mmol) and Raney Nickel (200 mg) in ethanol was hydrogenated (90 psi) at room temperature for 3 days. The mixture was filtered through a pad of Celite, washed with MeOH, and concentrated. The residue was dissolved in MeOH, and treated with HCl (4 N in dioxane, 60 mmol), and concentrated to give perhydro-2H-pyran-4-ylamine hydrochloride (89%).

Step 3. Preparation of (4-{[(1Z)-2-aza-1-(cis-3,5-dimethylpiperazinyl)-2-perhydro-2H-pyran-4-ylvinyl]amino}phenyl)-N-[2-(2,4-dichlorophenyl)ethyl]carboxamide.

A mixture of perhydro-2H-pyran-4-ylamine hydrochloride (0.5 mmol) and a phosgene solution (20% in toluene, 4 mL) was heated at 110° C. overnight. Toluene and excess phosgene were removed in vacuo. To the residue was added a solution of {4-[aza(triphenylylidene)methyl]phenyl}-N-[2-(2,4-dichlorophenyl)-ethyl]carboxamide prepared in situ from [4-(azadiazomvinyl)phenyl]-N-[2-(2,4-dichlorophenyl)-ethyl]carboxamide (0.3 mmol) and triphenylphosphine (0.3 mmol) in THF. The solution was heated for 70° C. for 4 hours. To the solution was added cis-2,6-dimethylpiperazine (0.5 mmol) and heated at 70° C. for 2 hours. The mixture was concentrated and subjected to HPLC purification to give (4-{[(1Z)-2-aza-1-(cis-3,5-dimethylpiperazinyl)-2-perhydro-2H-pyran-4-ylvinyl]amino}phenyl)-N-[2-(2,4-dichlorophenyl)ethyl]carboxamide as its TFA salt.

HPLC: 20.50 minutes
MS: MH+=532.2

Example 31

Preparation of (4-{[2-(trans-2-phenylcyclohexyl)(1Z)-2-aza-1-(3,5-dimethylpiperazinyl)vinyl]amino}phenyl)-N-[2-(2,4-dichlorophenyl)ethyl]carboxamide Step 1. Preparation of 2-phenylcyclohexyloxime.

To a solution of 2-phenylcyclohexanone (28.6 mmol) in water and ethanol, and sodium acetate (34.4 mmol) was added hydroxylamine hydrochloride (43.0 mmol). The reaction was heated at 70° C. overnight, and ethanol was removed under reduced pressure. The reaction mixture was dissolved in water and extracted with ether. The combined organic extracts were washed with brine, dried over sodium sulfate, and concentrated to give 2-phenylcyclohexyloxime (92%) as a fluffy white powder.

Step 2. Preparation of trans-2-phenylcyclohexylamine.

To a solution of trans-2-phenylcyclohexyloxime (7.92 mmol) in ethanol were added sodium pieces (about 3.0 g in portions). The reaction was heated to reflux at 110° C. overnight. More sodium pieces were added and the reaction was further stirred for another 6 hours. The reaction mixture was treated with concentrated HCl in water, and ethanol was removed in vacuo. The aqueous layer was extracted with ether and neutralized with aqueous KOH. The aqueous layer was treated with ether. The ether layers were washed with brine, dried over sodium sulfate, and concentrated in vacuo to give 2-phenylcyclohexylamine as a brown oil.

Step 3. Preparation of trans-2-phenylcyclohexylisocyanate.

To a solution of 2-phenylcyclohexylamine (2.28 mmol) in methanol was added HCl (4.0 M in dioxane, 0.57 mL). The solution was concentrated and treated with phosgene solution (20% in toluene, 16.0 mL). The reaction was heated at 110° C. overnight and concentrated in vacuo.

Step 4. Preparation of (4-{[2-(trans-2-phenylcyclohexyl)(1Z)-2-aza-1-(3,5-dimethyl-piperazinyl)vinyl]amino}phenyl)-N-[2-(2,4-dichlorophenyl)ethy]carboxamide.

To a solution of [4-(azadiazomvinyl)phenyl]-N-[2-(2,4-dichlorophenyl)-ethyl]carboxamide (0.149 mmol) in THF was added triphenylphosphine (0.149 mmol). The mixture was stirred for 10 minutes and transferred to 2-phenylcyclohexyl isocyanate (about 100 mg) as prepared above. The reaction was heated at 70° C. overnight. 2,6-dimethylpiperazine (0.149 mmol) was added, and the reaction was heated 3 hours at 70° C. The solution was concentrated, and purified via HPLC to give (4-{[2-(trans-2-phenylcyclohexyl)(1Z)-2-aza-1-(3,5-dimethylpiperazinyl)vinyl]amino}phenyl)-N-[2-(2,4-dichlorophenyl)ethyl]carboxamide as an off-white powder.

HPLC: 24.86 minutes
MS: MH+=606.63

Example 32

Preparation of (4-{[1-((3S)-3-methylpiperazinyl)(1Z)-2-aza-2-(4-methoxycyclohexyl)vinyl]amino}phenyl)-N-[2-(2,4-dichlorophenyl)ethyl]carboxamide Step 1. Preparation of 4-methoxycyclohexanisocyanate.

To a solution of 4-methoxycyclohexanecarboxylic acid (2.0 mmol), in DCM was added oxalyl chloride and two drops of DMF. After 1 hour, DCM and excess oxalyl chloride were removed, and the produce was pumped on for 10 minutes. The residue was dissolved in acetone and added to a solution of sodium azide (0.3 g) in water at 0° C. The mixture was stirred at room temperature for 30 minutes and then diluted with chloroform. The organic layer was washed with brine, dried over $Na_2SO_4$, and concentrated to 10 mL. The solution was heated at 90° C. for 30 minutes, concentrated, and dissolved in THF (4 mL).

Step 2. Preparation of {4-[1,3-diaza-3-(4-methoxycyclohexyl)propa-1,2-dienyl]phenyl}-N-[2-(2,4-dichlorophenyl)ethyl]carboxamide.

To a solution of {4-[aza(triphenylylidene)methyl]phenyl}-N-[2-(2,4-dichlorophenyl)ethyl]carboxamide, prepared in situ from [4-(azadiazomvinyl)-phenyl]-N-[2-(2,4-dichlorophenyl)-ethyl]carboxamide (0.3 mmol) and triphenylphosphine (0.3 mmol) in THF, was added the 4-methoxycyclohexanisocyanate THF solution prepared above. The solution was heated at 70° C. overnight.

Step 3. Preparation of (4-{[1-((3S)-3-methylpiperazinyl)(1Z)-2-aza-2-(4-methoxycyclohexyl)vinyl]amino}phenyl)-N-[2-(2,4-dichlorophenyl)ethyl]carboxamide.

To the carbodiimide solution (0.15 mmol) from Step 2, was added (S)-2-methylpiperazine (0.25 mmol). The solution was heated at 70° C. for 2 hours, and subjected to HPLC purification to give (4-{[1-((3S)-3-methylpiperazinyl)(1Z)-2aza-2-(4-methoxycyclohexyl)vinyl]amino}phenyl)-N-[2-(2,4-dichlorophenyl)ethyl]carboxamide (a mixture of cis and trans isomers) as its TFA salt.

HPLC: 21.34 and 21.95 minutes
MS: MH+=546

Example 33

Preparation of (4-{[(1Z)-2-aza-1-(cis-3,5-dimethylpiperazinyl)-2-(4-methoxycyclohexyl)vinyl]amino}phenyl)-N-[2-(2,4-dichlorophenyl)ethyl]carboxamide To a {4-[1,3-diaza-3-(4-methoxycyclohexyl)propa-1,2-dienyl]phenyl}-N-[2-(2,4-dichlorophenyl)ethyl]carboxamide solution (0.15 mmol) was added 2,6-dimethylpiperazine (0.25 mmol). The solution was heated at 70° C. for 2 hours, and subjected to HPLC purification to give (4-{[(1Z)-2-aza-1-(cis-3,5-dimethylpiperazinyl)-2-(4-methoxycyclohexyl)vinyl]amino}phenyl)-N-{[2-(2,4-dichlorophenyl)-ethyl]carboxamide (a mixture of cis and trans isomers) as its TFA salt.

HPLC: 21.64 and 22.24 minutes
MS: MH+=560

Example 34

Preparation of (4-{[1-((3S)-3-methylpiperazinyl)(1Z)-2-aza-2-(4-phenylcyclohexyl)vinyl]amino}phenyl)-N-[2-(2,4-dichlorophenyl)ethyl]carboxamide Step 1. Preparation of 1-(hydroxyimino)-4-phenylcyclohexane.

A mixture of 4-phenylcyclohexanone (28.7 mmol), hydroxylamine hydrochloride (36.0 mmol), and sodium acetate (60.95 mmol) in ethanol and water was heated at 70° C. overnight. Ethanol was removed, and the residue was dissolved in water and ethyl acetate. The aqueous layer was extracted with ethyl acetate. The combined organic layers were washed with brine, dried, and concentrated to give 1-(hydroxyimino)-4-phenylcyclohexane (97%).

Step 2. Preparation of 4-phenylcyclohexylamine.

A mixture of 1-(hydroxyimino)-4-phenylcyclohexane (17.4 mmol) and Raney Nickel (300 mg) in ethanol was hydrogenated (90 psi) at 50° C. for 40 hours. The mixture was filtered through a pad of Celite, washed with MeOH, and concentrated. The residue was dissolved in MeOH, treated with HCl (4 N in dioxane, 20 mmol), and concentrated to give 4-phenylcyclohexylamine hydrochloride (100%).

Step 3. Preparation of 4-phenylcyclohexanisocyanate.

A mixture of 4-phenylcyclohexylamine hydrochloride (0.5 mmol) and a phosgene solution (20% in toluene, 4 mL) was heated at 110° C. overnight. Toluene and excess phosgene were removed in vacuo to give a residue.

Step 4. Preparation of (4-{[1-((3S)-3-methylpiperazinyl)(1Z)-2-aza-2-(4-phenylcyclohexyl)vinyl]amino}phenyl)-N-[2-(2,4-dichlorophenyl)ethyl]carboxamide.

To the isocyanate residue was added a solution of {4-[aza(triphenylylidene)methyl]phenyl}-N-[2-(2,4- dichlorophenyl)-ethyl]carboxamide prepared in situ from [4-(azadiazomvinyl)phenyl]-N-[2-(2,4-dichlorophenyl)-ethyl]carboxamide (0.3 mmol) and triphenylphosphine (0.3 mmol) in THF. The solution was heated for 70° C. overnight. To half of the solution was added (S)-2-methylpiperazine (0.25 mmol), and the mixture was heated at 70° C. for 2 hours. The mixture was concentrated and subjected to HPLC purification to give (4-{[1-((3S)-3-methylpiperazinyl)(1Z)-2-aza-2-(4-phenylcyclohexyl)vinyl]amino}phenyl)-N-[2-(2,4-dichlorophenyl)ethyl]carboxamide as its TFA salt.

HPLC: 26.37 minutes
MS: MH+=592

Example 35

Preparation of (4-{[(1Z)-2-aza-1-(cis-3,5-dimethylpiperazinyl)-2-(4-phenylcyclohexyl)vinyl]amino}phenyl)-N-[2-(2,4-dichlorophenyl)ethyl]carboxamide To half of the solution prepared above (Example 34) was added cis-2,6-dimethylpiperazine (0.25 mmol), and the mixture was heated at 70° C. for 2 hours. The mixture was concentrated and subjected to HPLC purification to give (4-{[(1Z)-2-aza-1-(cis-3,5-dimethylpiperazinyl)-2-(4-phenylcyclohexyl)vinyl]amino}phenyl)-N-[2-(2,4-dichlorophenyl)ethyl]carboxamide as its TFA salt.

HPLC: 26.52 minutes
MS: MH+=606

Example 36

General Procedure for the Preparation of Polystyrene-Bound 4-hydroxy-2-methoxybenzaldehyde.

Merrifield resin (1 equivalent) was soaked in N-methylpyrrolidinone (NMP) for 5 minutes, after which time, 2 equivalents of 4-hydroxy-2-methoxybenzaldehyde and $K_2CO_3$ (2 equivalents) were added. The resulting mixture was degassed with argon and heated at 120° C. for 18 hours with shaking. The resin was filtered and washed with DMF, $H_2O$, MeOH and $CH_2Cl_2$. The beads were then dried overnight under vacuum to yield resin-bound 4-hydroxy-2-methoxybenzaldehyde.

Example 37

General Procedure for the Preparation of Polystyrene-Bound Amines.

Resin-bound 4-hydroxy-2-methoxybenzaldehyde (1 equivalent) was treated with 10 equivalents of a primary amine in $(MeO)_3CH$ for 18 hours at 23° C. with shaking. The resin-bound imine was rinsed quickly (3 ×) with anhydrous $CH_2Cl_2$. The resin-bound imine was immediately reduced using pyridine-borane complex (5 equivalents) in a solution of $CH_2Cl_2$:MeOH:AcOH (2:2:1) with shaking at 23° C. for 18 hours. The resulting resin-bound amine was washed with $CH_2Cl_2$, MeOH, $Et_3N$ and $CH_2Cl_2$ and dried overnight under vacuum.

Example 38

General Procedure for the Preparation of Polystyrene-Bound P-Azidobenzamides.

A mixture of resin-bound amine (1 equivalent), p-azidobenzoic acid (10 equivalents) and anhydrous $CH_2Cl_2$ was shaken until most of the acid had dissolved. To this mixture was added DIC (3.3 equivalents), and the resulting mixture was shaken for 3 hours at 23° C. After this time, the resin was washed with $CH_2Cl_2$ and anhydrous THF (each wash was repeated 3×) and the resin-bound benzamide was dried overnight under vacuum. Example 39

General Procedure for the Preparation of Polystyrene-Bound P-Benzamido Iminophosphoranes.

To a mixture of resin-bound p-azidobenzamide (1 equivalent) and anhydrous THF was added $Ph_3P$ (10 equivalents) at 23° C. Vigorous bubbling ensued which subsided after about 30 minutes. The resulting mixture was shaken at room temperature for 18 hours, filtered, washed with anhydrous THF and $CH_2Cl_2$, and dried under vacuum overnight to yield resin-bound p-benzamido iminophosphorane.

Example 40

General Procedure for the Preparation of Polystyrene-Bound P-Benzamido Carbodiimides.

A mixture of resin-bound p-benzamido iminophosphorane (1 equivalent) and anhydrous THF was treated with an isocyanate (10 equivalents) at 23° C. for 16 hours with shaking. The resin was then filtered, washed with anhydrous THF and $CH_2Cl_2$ and dried under vacuum overnight to yield resin-bound p-benzamido carbodiimide.

Example 41

General Procedure for the Preparation of Polystyrene-Bound P-Benzamido Guanidines.

A mixture of resin-bound p-benzamdio carbodiimide (1 equivalent) and anhydrous THF was treated with an amine (20 equivalents) for 36 hours at 23° C. with shaking. The resin was then filtered, washed with DMF, MeOH and $CH_2Cl_2$ and dried under vacuum to yield resin-bound p-benzamido guanidine. The desired product was liberated from the polystyrene support using TFA: $CH_2Cl_2$ (4:1) at 23° C. for 3 hours with shaking. The resin was filtered, washed with $CH_2Cl_2$, and the resulting filtrate was concentrated under reduced pressure to yield p-benzamido guanidine as the TFA salt.

The following compounds were synthesized using the general procedures described above:

{4-[((1Z)-2-aza-1-{[2-(dimethylamino)ethyl]benzylamino}-2-cyclohexylvinyl)amino]phenyl}-N-(2-phenylethyl)carboxamide. LC/MS m/z 526.7 (MH+), Rt 3.15 minutes.

{4-[((1Z)-2-aza-1-{[2-(dimethylamino)ethyl]benzylamino}-2-cyclohexylvinyl)amino]phenyl}-N-[2-(4-methoxyphenyl)ethyl]carboxamide. LC/MS m/z 556.8 (MH+), Rt 3.28 minutes.

{4-[((1Z)-2-aza-1-{[2-(dimethylamino)ethyl]benzylamino}-2-cyclohexylvinyl)amino]phenyl}-N-[2-(3-chlorophenyl)ethyl]carboxamide. LC/MS m/z 561.2 (MH+), Rt 3.29 minutes.

{4-[((1Z)-2-aza-2-cyclohexyl-1-{[(4-fluorophenyl)methyl](2-pyridylmethyl)amino}vinyl)amino]phenyl}-N-(2-phenylethyl)carboxamide. LC/MS m/z 564.7 (MH+), Rt 3.98 minutes.

{4-[((1Z)-2-aza-1-{[2-(dimethylamino)ethyl]benzylamino}-2-cyclohexylvinyl)amino]phenyl}-N-

[2-(2,4-dichlorophenyl)ethyl]carboxamide. LC/MS m/z 595.6 (MH+), Rt 3.53 minutes.

{4-[((1Z)-2-aza-1-{[2-(dimethylamino)ethyl] benzylamino}-2-cyclohexylvinyl)amino]phenyl}-N-[2-(4-ethylphenyl)ethyl]carboxamide. LC/MS m/z 554.8 (MH+), Rt 3.53 minutes.

{4-[((1Z)-2-aza-1-{[2-(dimethylamino)ethyl] benzylamino}-2-cyclohexylvinyl)amino]phenyl}-N-[2-(2-methoxyphenyl)ethyl]carboxamide. LC/MS m/z 556.8 (MH+), Rt 3.23 minutes.

{4-[((1Z)-2-aza-1-{[2-(dimethylamino)ethyl] benzylamino}-2-cyclohexylvinyl)amino]phenyl}-N-(2-cyclohex-1-enylethyl)carboxamide. LC/MS m/z 530.8 (MH+), Rt 2.85 minutes.

{4-[((1Z)-2-aza-1-{[2-(dimethylamino)ethyl] benzylamino}-2-cyclohexylvinyl)amino]phenyl}-N-[2-(2-fluorophenyl)ethyl]carboxamide. LC/MS m/z 544.7 (MH+), Rt 2.02 minutes.

{4-[((1Z)-2-aza-1-{[2-(dimethylamino)ethyl] benzylamino}-2-cyclohexylvinyl)amino]phenyl}-N-[2-(2-chlorophenyl)ethyl]carboxamide. LC/MS m/z 561.2 (MH+), Rt 2.10 minutes.

{4-[((1Z)-2-aza-1-{[2-(dimethylamino)ethyl] benzylamino}-2-cyclohexylvinyl)amino]phenyl}-N-[2-(4-bromophenyl)ethyl]carboxamide. LC/MS m/z 605.6 (MH+), Rt 2.20 minutes.

{4-[((1Z)-2-aza-1-{[2-(dimethylamino)ethyl] benzylamino}-2-cyclohexylvinyl)amino]phenyl}-N-[2-(4-methylphenyl)ethyl]carboxamide. LC/MS m/z 540.8 (MH+), Rt 2.10 minutes.

{4-[((1Z)-2-aza-1-{[2-(dimethylamino)ethyl] benzylamino}-2-cyclohexylvinyl)amino]phenyl}-N-[2-(4-chlorophenyl)ethyl]carboxamide. LC/MS m/z 561.2 (MH+), Rt 2.10 minutes.

[4-({(1 E)-2-aza-1-[({1-[(4-chlorophenyl)methyl]-5-methylimidazol-4-yl}methyl)amino]-2-cyclohexylvinyl}amino)phenyl]-N-[2-(4-methoxyphenyl)ethyl]carboxamide. LC/MS m/z 614.2 (MH+), Rt 2.20 minutes.

{4-[((1Z)-2-aza-1-{[2-(dimethylamino)ethyl] benzylamino}-2-cyclohexylvinyl)amino]phenyl}-N-[2-(4-methoxyphenyl)ethyl]carboxamide. LC/MS m/z 556.8 (MH+), Rt 3.27 minutes.

(4-{[(1 E)-2-aza-2-cyclohexyl-1-(4-methylpiperidyl)vinyl]amino}phenyl)-N-[2-(2,4-dichlorophenyl)ethyl]carboxamide. LC/MS m/z 516.5 (MH+), Rt 3.35 minutes.

{4-[((1Z)-2-aza-2-cyclohexyl-1-piperazinylvinyl)amino] phenyl}-N-[2-(2,4-dichlorophenyl)ethyl]carboxamide. LC/MS m/z 503.5 (MH+), Rt 3.33 minutes.

{4-[((1Z)-2-aza-2-cyclohexyl-1-(1,4-diazaperhydroepinyl)vinyl)amino]-phenyl}-N-[2-(2,4-dichlorophenyl)ethyl]carboxamide. LC/MS m/z 517.5 (MH+), Rt 3.36 minutes.

(4-{[1-(2,5-trans-dimethylpiperazinyl)(1Z)-2-aza-2-cyclohexylvinyl]amino}phenyl)-N-[2-(2,4-dichlorophenyl)ethyl]carboxamide. LC/MS m/z 531.5 (MH+), Rt 3.42 minutes.

(4-{[(1Z)-2-aza-1-(2,5-diazabicyclo[4.4.0]dec-2-yl)-2-cyclohexylvinyl]amino}phenyl)-N-[2-(2,4-dichlorophenyl)ethyl]carboxamide. LC/MS m/z 557.6 (MH+), Rt 3.52 minutes.

(4-{[1-((3R)-3-methylpiperazinyl)(1Z)-2-aza-2-cyclohexylvinyl]-amino}phenyl)-N-[2-(2,4-dichlorophenyl)ethyl]carboxamide. LC/MS m/z 517.5 (MH+), Rt 3.36 minutes.

{4-[((1Z)-2-aza-1-{[2-(dimethylamino)ethyl][(4-ethylphenyl)methyl]-amino}-3-methylbut-1-enyl)amino]phenyl}-N-[2-(2,4-dichlorophenyl)ethyl]-carboxamide. LC/MS m/z 583.6 (MH+), Rt 3.58 minutes.

(4-{[1-((3S)-3-methylpiperazinyl)(1Z)-2-aza-2-cyclohexylvinyl]amino}-3-methoxyphenyl)-N-[2-(2,4-dichlorophenyl)ethyl]carboxamide. LC/MS m/z 547.5 (MH+), Rt 3.25 minutes.

(4-{[1-((3S)-3-methylpiperazinyl)(1Z)-2-aza-2-cyclohexylvinyl]amino}-2-chlorophenyl)-N-[2-(2,4-dichlorophenyl)ethyl]carboxamide. LC/MS m/z 552.0 (MH+), Rt 3.32 minutes.

(4-{[1-((3S)-3-methylpiperazinyl)(1Z)-2-aza-2-cyclohexylvinyl]amino}-3-methylphenyl)-N-[2-(2,4-dichlorophenyl)ethyl]carboxamide. LC/MS m/z 531.5 (MH+), Rt 3.30 minutes. (4-{[1-((3S)-3-methylpiperazinyl)(1Z)-2-aza-2-cyclohexylvinyl] amino}-5-chloro-2-methoxyphenyl)-N-[2-(2,4-dichlorophenyl)ethyl]carboxamide. LC/MS m/z 582.0 (MH+), Rt 3.48 minutes.

Example 42

Generic Experimentals for Examples 43–59

Step 1. Synthesis of Immobilized{4-[aza(triphenylylidene) methyl]phenyl}-N-[2-(2,4-dichlorophenyl)ethyl] carboxamide 1 mmol of resin bound triphenylphosphine in a round-bottomed flask was suspended in THF and cooled to 0° C. with stirring. 1 mmol of the azide ([4-(azadiazomvinyl) phenyl]-N-[2-(2,4-dichlorophenyl)ethyl]carboxamide) was then added slowly in small portions and the flask vented to release the evolved nitrogen. After 30 minutes at 0° C., the reaction was stirred at room temperature for 8 hours and then filtered and washed with dry DCM and the resin immobilized{4-[aza(triphenylylidene)methyl]phenyl}-N-[2-(2,4-dichlorophenyl)ethyl]carboxamide was dried in vacuo for 8 hours.

Step 2. Synthesis of Isocyanates from Amine Hydrochlorides

To 1 g of an amine hydrochloride in a round-bottomed flask fitted with a reflux condenser was added 6 ml of phosgene solution in toluene (20%), and the suspension heated to reflux (110° C.) till it turned clear (usually after about 2–8 hours). The solution was cooled and concentrated in vacuo and the resulting isocyanate was either distilled or used as such.

Step 3. Synthesis of Isocyanates from Carboxylic Acids

To 1 mmol of carboxylic acid dissolved in 5 ml of DCM was added 1 mmol of triethyl amine and 1 mmol of diphenylphosphorazidate, and the reaction was stirred under nitrogen for 30 minutes at 0° C. and then at 50° C. for 3 hours. The reaction was then cooled to room temperature, concentrated in vacuo and then dry THF was added to make up a stock solution of the isocyanate which was used without further purification.

Step 4. Synthesis of Carbodiimide

To resin bound phophinimine (Step 1 above; 1 mmol) suspended in dry THF was added 1 mmol of the isocyanate from Steps 2 or 3 above, and the suspension was stirred for 8 hours at 70° C. in a capped vial.

Step 5. Synthesis of Guanidine

The reaction in Step 4 above was cooled to room temperature, 2 equivalents of a piperazine were added, and the reaction mixture was heated at 70° C. with stirring for 2 hours and cooled. The reaction mixture was then filtered, washed with THF, and the combined filtrate was concentrated in vacuo and the residue purified by silica gel chromatography, eluting with 10% methanol in DCM with 2% triethyl amine. The final product could be further purified with reversed phase HPLC.

General Experimental Scheme for Examples 43–59

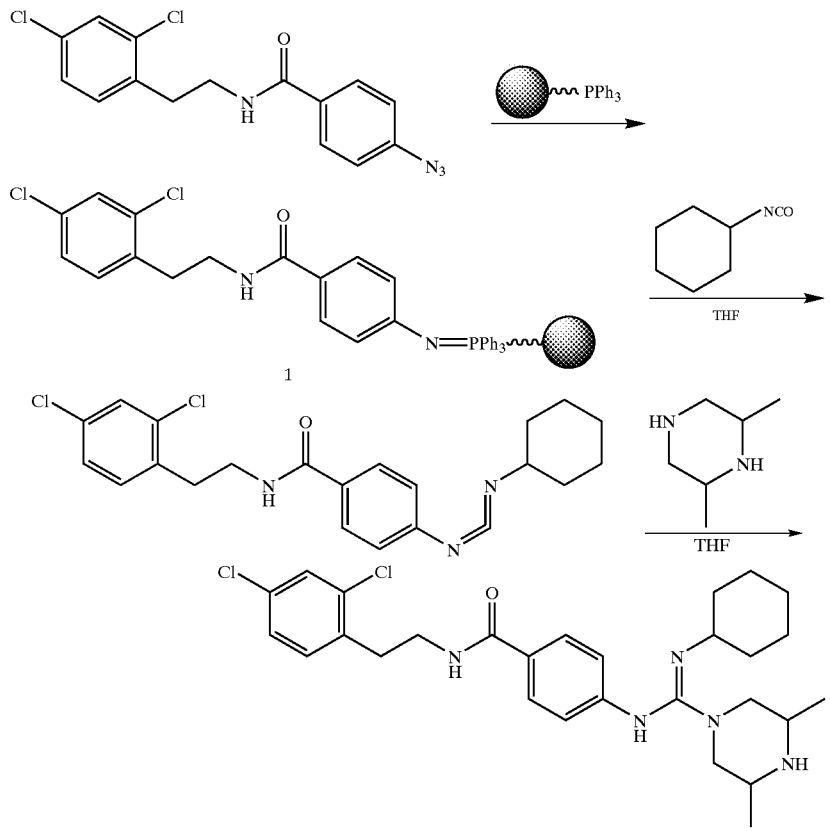

Example 43

Synthesis of (4-([trans-2-methylcyclohexyl)(1Z)-2-aza-1-(3,5-dimethylpiperazinyl)vinyl]amino}phenyl)-N-[2-(2,4-dichlorophenyl)ethyl]carboxamide Step 1. Synthesis of Immobilized{4-[aza(triphenylylidene)methyl]phenyl}-N-[2-(2,4-dichlorophenyl)ethyl]carboxamide 1 mmol of resin bound triphenylphosphine in a round-bottomed flask was suspended in THF and cooled to 0° C. with stirring. 1 mmol of the azide ([4-(azadiazomvinyl)phenyl]-N-[2-(2,4-dichlorophenyl)ethyl]carboxamide) was then added slowly in small portions and the flask vented to release the evolved nitrogen. After 30 minutes at 0° C., the reaction was stirred at room temperature for 8 hours and then filtered, washed with dry DCM, and the resin immobilized {4-[aza(triphenylylidene)methyl]phenyl}-N-[2-(2,4-dichlorophenyl) ethyl]carboxamide was dried in vacuo for 8 hours.

Step 2. Synthesis of Isocyanate from Amine Hydrochloride

To 1 g of trans-2-methylcyclohexylamine hydrochloride (synthesized by hydroboration of 2-methylcyclohexene as described by H. C. Brown et al., *Tetrahedron*, 43, No.18, 4071–4078 (1987)) in a round-bottomed flask fitted with a reflux condenser, was added 6 ml of phosgene solution in toluene (20%) and the suspension was heated to reflux (110° C.) until it turned clear (usually after about 2–8 hours). The solution was cooled and concentrated in vacuo and the resulting isocyanate was either distilled or used as such.

Step 3. Synthesis of Carbodiimide

To resin bound phophinimine (1 mmol) suspended in dry THF was added 1 mmol of the isocyanate from step 2 above, and the suspension was stirred for 8 hours at 70° C. in a capped vial.

Step 4. Synthesis of Guanidine

The product of step 3 above was cooled to room temperature, 2 equivalents of the (S)-(+)-2-methylpiperazine were added, and the reaction mixture was heated at 70° C. with stirring for 2 hours and cooled. The reaction mixture was then filtered, washed with THF, and the combined filtrate was concentrated in vacuo and the residue purified by silica gel chromatography, eluting with 10% methanol in DCM with 2% triethyl amine. The final product could be further purified with reverse phase HPLC.

HPLC: 7.55 minutes
MS: MH+=544.5

Example 44

Synthesis of (4-{[1-((3R)-3-methylpiperazinyl)-2-((1S,2S)-2-methylcyclohexyl)(1Z)-2-azavinyl]amino}phenyl)-N-[2-(2,4-dichlorophenyl)ethyl]carboxamide Step 1. Synthesis of Immobilized{4-[aza(triphenylylidene)methyl]phenyl}-N-[2-(2,4-dichlorophenyl)ethyl]carboxamide 1 mmol of resin bound triphenylphosphine in a round-bottomed flask was suspended in THF and cooled to 0° C. with stirring. 1 mmol of the azide ([4-(azadiazomvinyl)phenyl]-N-[2-(2,4-dichlorophenyl)ethyl]carboxamide) was then added slowly in small portions and the flask vented to release the evolved nitrogen. After 30 minutes at 0° C., the reaction was stirred at room temperature for 8 hours and then filtered, washed with dry DCM and the resin immobilized{4-[aza(triphenylylidene)methyl]phenyl}-N-[2-(2,4-dichlorophenyl)ethyl]carboxamide was dried in vacuo for 8 hours.

Step 2. Synthesis of Isocyanate from Amine Hydrochloride

To 1 g of trans-2-methylcyclohexylamine hydrochloride (synthesized by hydroboration of 2-methylcyclohexene as described by H. C. Brown et al, *Tetrahedron*, 43, No.18, 4071–4078(1987)) in a round-bottomed flask fitted with a reflux condenser was added 6 ml of phosgene solution in toluene (20%), and the suspension was heated to reflux (110° C.) until it turned clear (usually after about 2–8 hours). The solution was cooled and concentrated in vacuo, and the resulting isocyanate was either distilled or used as such.

Step 3. Synthesis of Carbodiimide

To resin bound phophinimine (1 mmol) suspended in dry THF was added 1 mmol of the isocyanate from step 2 above, and the suspension was stirred for 8 hours at 70° C. in a capped vial.

Step 4. Synthesis of Guanidine

The reaction product of step 3 above was cooled to room temperature and 2 equivalents of (S)-(+)-2-methylpiperazine were added. The reaction mixture was then heated at 70° C. with stirring for 2 hours and cooled. The resulting mixture was filtered, washed with THF, and the combined filtrate was concentrated in vacuo and the residue purified by silica gel chromatography, eluting with 10% methanol in DCM with 2% triethyl amine. The final product could be further purified with reversed phase HPLC.

HPLC: 7.27 minutes
MS: MH+=530.5

Example 45

Synthesis (4-{[(1Z)-2-aza-2-(2,6-dimethylcyclohexyl)-1-(3,5-dimethylpiperazinyl)vinyl]amino}phenyl)-N-[2-(2,4-dichlorophenyl)ethyl]carboxamide Step 1. Synthesis of Immobilized{4-[aza(triphenylylidene)methyl]phenyl}-N-[2-(2,4-dichlorophenyl)ethyl]carboxamide 1 mmol of resin bound triphenylphosphine in a round-bottomed flask was suspended in THF and cooled to 0° C. with stirring. 1 mmol of the azide ([4-(azadiazomvinyl)phenyl]-N-[2-(2,4-dichlorophenyl)ethyl]carboxamide) was then added slowly in small portions and the flask vented to release the evolved nitrogen. After 30 minutes at 0° C., the reaction was stirred at room temperature for 8 hours and then filtered, washed with dry DCM, and the resin immobilized {4-[aza(triphenylylidene)methyl]phenyl}-N-[2-(2,4-dichlorophenyl) ethyl]carboxamide was dried in vacuo for 8 hours.

Step 2. Synthesis of Isocyanate from Amine Hydrochloride

To 1 g of 2,6-dimethylcyclohexylamine hydrochloride (synthesized by the reductive amination of 2,6-dimethylcyclohexanone as in Sukanta Bhattacharyya et al, *Synlett.*, 11, 1781–1783 (1999)) in a round-bottomed flask fitted with a reflux condenser was added 6 ml of phosgene solution in toluene (20%), and the suspension was heated to reflux (110° C.) until it turned clear (usually after about 2–8 hours). The solution was cooled and concentrated in vacuo and the resulting isocyanate was either distilled or used as such.

Step 3. Synthesis of Carbodiimide

To resin bound phosphinimine (1 mmol) suspended in dry THF was added 1 mmol of the isocyanate from step 2 above, and the suspension was stirred for 8 hours at 70° C. in a capped vial.

Step 4. Synthesis of Guanidine

The reaction product of step 3 above was cooled to room temperature and 2 equivalents of the cis-2,6-dimethylpiperazine were added. The reaction mixture was then heated at 70° C. with stirring for 2 hours and cooled. The resulting mixture was then filtered, washed with THF, and the combined filtrate was concentrated in vacuo and the residue purified by silica gel chromatography, eluting with 10% methanol in DCM with 2% triethyl amine. The final product could be further purified with reversed phase HPLC.

HPLC: 7.6–7.9 minutes
MS: MH+=55

Example 46

Synthesis of (4-{[1-((3S,5S)-3,5-dimethylpiperazinyl)(1Z)-2-aza-2-cyclohexylvinyl]amino}phenyl)-N-[2-(2,4-dichlorophenyl)ethyl]carboxamide Step 1. Synthesis of Immobilized{4-[aza(triphenylylidene)methyl]phenyl}-N-[2-(2,4-dichlorophenyl)ethyl]carboxamide 1 mmol of resin bound triphenylphosphine in a round-bottomed flask was suspended in THF and cooled to 0° C. with stirring. 1 mmol of the azide ([4-(azadiazomvinyl)phenyl]-N-[2-(2,4-dichlorophenyl)ethyl]carboxamide) was then added slowly in small portions and the flask vented to release the evolved nitrogen. After 30 minutes at 0° C., the reaction was stirred at room temperature for 8 hours and then filtered, washed with dry DCM, and the immobilized {4-[aza(triphenylylidene)methyl]phenyl}-N-[2-(2,4-dichlorophenyl)ethyl]carboxamide was dried in vacuo for 8 hours.

Step 2. Synthesis of Isocyanate from Amine Hydrochloride

To 1 g of an amine hydrochloride in a round-bottomed flask fitted with a reflux condenser was added 6 ml of phosgene solution in toluene (20%). The suspension was heated to reflux (110° C.) until it turned clear (usually after about 2–8 hours). The solution was cooled and concentrated in vacuo, and the resulting isocyanate was either distilled or used as such.

Step 3. Synthesis of Carbodiimide

To resin bound phophinimine (1 mmol) suspended in dry THF was added 1 mmol of the isocyanate from step 2 above. The suspension was then stirred for 8 hours at 70° C. in a capped vial.

Step 4. Synthesis of Guanidine

The reaction product of step 3 above was cooled to room temperature and 2 equivalents of (2S,6S)-2,6-dimethylpiperazine (synthesized as in E. Jon Jacobson et al., *J. Org. Chem.*, 60, 4177–83 (1995)) were added and the reaction mixture was heated at 70° C. with stirring for 2 hours and cooled. The reaction mixture was then filtered, washed with THF, and the combined filtrate was concentrated in vacuo and the residue purified by silica gel chromatography, eluting with 10% methanol in DCM with 2% triethyl amine. The final product could be further purified with reversed phase HPLC.

HPLC: 7.3 minutes
MS: MH+=530.3

Example 47

Synthesis of (4-{[(1Z)-2-aza-2-(2,3-dimethylcyclohexyl)-1-(3,5-dimethylpiperazinyl)vinyl]amino}phenyl)-N-[2-(2,4-dichlorophenyl)ethyl]carboxamide Step 1. Synthesis of Immobilized{4-[aza(triphenylylidene)methyl]phenyl}-N-[2-(2,4-dichlorophenyl)ethyl]carboxamide 1 mmol of resin bound triphenylphosphine in a round-bottomed flask was suspended in THF and cooled to 0° C. with stirring. 1 mmol of the azide ([4-(azadiazomvinyl)phenyl]-N-[2-(2,4-dichlorophenyl)ethyl]carboxamide) was then added slowly in small portions and the flask vented to release the evolved nitrogen. After 30 minutes at 0° C., the reaction was stirred at room temperature for 8 hours and then filtered, washed with dry DCM, and the resin immobilized {4-[aza(triphenylylidene)methyl]phenyl}-N-[2-(2,4-dichlorophenyl) ethyl]carboxamide was dried in vacuo for 8 hours.

Step 2. Synthesis of Isocyanate from Amine Hydrochloride

To 1 g of 2,3-dimethylcyclohexylamine hydrochloride in a round-bottomed flask fitted with a reflux condenser, was added 6 ml of phosgene solution in toluene (20%). The suspension was then heated to reflux (110° C.) until it turned clear (usually after about 2–8 hours). The solution was cooled and concentrated in vacuo, and the resulting isocyanate was either distilled or used as such.

Step 3. Synthesis of Carbodiimide

To resin bound phophinimine (1 mmol) suspended in dry THF, was added 1 mmol of the isocyanate from step 2 above. The suspension was then stirred for 8 hours at 70° C. in a capped vial.

Step 4. Synthesis of Guanidine

The reaction product of step 3 above was cooled to room temperature and 2 equivalents of cis-2,6-dimethylpiperazine were added. The reaction mixture was then heated at 70° C. with stirring for 2 hours and cooled. The resulting mixture was filtered, washed with THF, and the combined filtrate was concentrated in vacuo and the residue purified by silica gel chromatography, eluting with 10% methanol in DCM with 2% triethyl amine. The final product could be further purified with reverse phase HPLC.

HPLC: 7.97 minutes
MS: MH+=558.5

Example 48

Synthesis of (4-{[1-((3S)-3-methylpiperazinyl)-2-(trans-2-methylcycloheptyl)(1Z)-2-azavinyl]amino}phenyl)-N-[2-(2,4-dichlorophenyl)ethyl]carboxamide Step 1. Synthesis of Immobilized{4-[aza(triphenylylidene)methyl]phenyl}-N-[2-(2,4-dichlorophenyl)ethyl]carboxamide 1 mmol of resin bound triphenylphosphine in a round-bottomed flask was suspended in THF and cooled to 0° C. with stirring. 1 mmol of the azide ([4-(azadiazomvinyl)phenyl]-N-[2-(2,4-dichlorophenyl)ethyl]carboxamide) was then added slowly in small portions and the flask vented to release the evolved nitrogen. After 30 minutes at 0° C., the reaction was stirred at room temperature for 8 hours. The reaction mixture was then filtered, washed with dry DCM, and the resin immobilized {4-[aza(triphenylylidene)methyl]phenyl}-N-[2-(2,4-dichlorophenyl) ethyl]carboxamide was dried in vacuo for 8 hours.

Step 2. Synthesis of Isocyanate from Amine Hydrochloride

To 1 g of trans-2-methylcycloheptylamine hydrochloride (synthesized by hydroboration of 2-methylcycloheptene as described by H. C. Brown et al, Tetrahedron, 43, No.18, 4071–4078 (1987)) in a round-bottomed flask fitted with a reflux condenser was added 6 ml of phosgene solution in toluene (20%). The suspension was then heated to reflux (110° C.) until it turned clear (usually after about 2–8 hours). The solution was cooled and concentrated in vacuo, and the resulting isocyanate was either distilled or used as such.

Step 3. Synthesis of Carbodiimide

To resin bound phophinimine (1 mmol) suspended in dry THF was added 1 mmol of the isocyanate from step 2 above. The suspension was then stirred for 8 hours at 70° C. in a capped vial.

Step 4. Synthesis of Guanidine

The reaction product of step 3 above was cooled to room temperature and 2 equivalents of the (S)-(+)-2-methylpiperazine were added. The reaction mixture was then heated at 70° C. with stirring for 2 hours and cooled. The resulting mixture was then filtered, washed with THF, and the combined filtrate was concentrated in vacuo and the residue purified by silica gel chromatography, eluting with 10% methanol in DCM with 2% triethyl amine. The final product could be further purified with reversed phase HPLC.

HPLC: 7.9 minutes
MS: MH+=544.3

Example 49

Synthesis of (4-{[1-((3R)-3-methylpiperazinyl)-2-((trans-2-methylcycloheptyl)(1Z)-2-azavinyl]amino}phenyl)-N-[2-(2,4-dichlorophenyl)ethyl]carboxamide Step 1. Synthesis of Immobilized{4-[aza(triphenylylidene)methyl]phenyl}-N-[2-(2,4-dichlorophenyl)ethyl]carboxamide 1 mmol of resin bound triphenylphosphine in a round-bottomed flask was suspended in THF and cooled to 0° C. with stirring. 1 mmol of the azide ([4-(azadiazomvinyl)phenyl]-N-[2-(2,4-dichlorophenyl)ethyl]carboxamide) was then added slowly in small portions and the flask vented to release the evolved nitrogen. After 30 minutes at 0° C., the reaction was stirred at room temperature for 8 hours. The reaction mixture was then filtered, washed with dry DCM, and the resin immobilized {4-[aza(triphenylylidene)methyl]phenyl}-N-[2-(2,4-dichlorophenyl) ethyl]carboxamide was dried in vacuo for 8 hours.

Step 2. Synthesis of Isocyanate from Amine Hydrochloride

To 1 g of trans-2methylcycloheptylamine hydrochloride (synthesized by hydroboration of 2-methylcycloheptene as described by H. C. Brown et al, *Tetrahedron*, 43, No.18, 4071–4078 (1987)) in a round-bottomed flask fitted with a reflux condenser, was added 6 ml of phosgene solution in toluene (20%). The suspension was heated to reflux (110° C.) till it turned clear (usually after about 2–8 hours). The solution was cooled and concentrated in vacuo, and the resulting isocyanate was either distilled or used as such.

Step 3. Synthesis of Carbodiimide

To resin bound phophinimine (1 mmol) suspended in dry THF was added 1 mmol of the isocyanate from step 2 above. The suspension was then stirred for 8 hours at 70° C. in a capped vial.

Step 4. Synthesis of Guanidine

The reaction product of step 3 above was cooled to room temperature and 2 equivalents of cis-2,6-dimethylpiperazine were added. The reaction mixture was heated at 70° C. with stirring for 2 hours and cooled. The resulting mixture was then filtered, washed with THF, and the combined filtrate was concentrated in vacuo and the residue purified by silica gel chromatography, eluting with 10% methanol in DCM with 2% triethyl amine. The final product could be further purified with reversed phase HPLC.

HPLC: 24.3 minutes
MS: MH+=558.5

Example 50

Synthesis of (4-{[1-((3S)-3-methylpiperazinyl)(1Z)-2-aza-2-(trans-4-methylcyclohexyl)vinyl]amino}phenyl)-N-[2-(2,4-dichlorophenyl)ethyl]carboxamide Step 1. Synthesis of Immobilized{4-[aza(triphenylylidene)methyl]phenyl}-N-[2-(2,4-dichlorophenyl)ethyl]carboxamide 1 mmol of resin bound triphenylphosphine in a round-bottomed flask was suspended in THF and cooled to 0° C. with stirring. 1 mmol of the azide ([4-(azadiazomvinyl)phenyl]-N-[2-(2,4-dichlorophenyl)ethyl]carboxamide) was then added slowly in small portions and the flask vented to release the evolved nitrogen. After 30 minutes at 0° C., the reaction was stirred at room temperature for 8 hours. The resulting mixture was then filtered, washed with dry DCM, and the resin immobilized{4-[aza(triphenylylidene)methyl]phenyl}-N-[2-(2,4-dichlorophenyl)ethyl]carboxamide was dried in vacuo for 8 hours.

Step 2. Synthesis of Isocyanate from Carboxylic Acid

To 1 mmol of trans-4-methylcyclohexanecarboxylic acid dissolved in 5 ml of DCM was added 1 mmol of triethyl amine and 1 mmol of diphenylphosphorazidate. The resulting mixture was stirred under nitrogen for 30 minutes at 0° C. and then at 50° C. for 3 hours. The resulting mixture was cooled to room temperature, concentrated in vacuo, and then dry THF was added to make up a stock solution of the isocyanate which was used without further purification.

Step 3. Synthesis of Carbodiimide

To resin bound phophinimine (1 mmol) suspended in dry THF was added 1 mmol of the isocyanate from step 2 above. The suspension was stirred for 8 hours at 70° C. in a capped vial.

Step 4. Synthesis of Guanidine

The reaction product of step 3 above was cooled to room temperature and 2 equivalents of (S)-(+)-2-methylpiperazine were added. The reaction mixture was heated at 70° C. with stirring for 2 hours and cooled. The resulting mixture was then filtered, washed with THF, and the combined filtrate was concentrated in vacuo and the residue purified by silica gel chromatography, eluting with 10% methanol in DCM with 2% triethyl amine. The final product was further purified with reversed phase HPLC.

HPLC: 7.59 minutes
MS: MH+=530.3

Example 51

Synthesis of (4-{[1-((3R)-3-methylpiperazinyl)(1Z)-2-aza-2-(trans-4-methylcyclohexyl)vinyl]amino}phenyl)-N-[2-(2,4-dichlorophenyl)ethyl]carboxamide Step 1. Synthesis of Immobilized{4-[aza(triphenylylidene)methyl]phenyl}-N-[2-(2,4-dichlorophenyl)ethyl]carboxamide 1 mmol of resin bound triphenylphosphine in a round-bottomed flask was suspended in THF and cooled to 0° C. with stirring. 1 mmol of the azide ([4-(azadiazomvinyl)phenyl]-N-[2-(2,4-dichlorophenyl)ethyl]carboxamide) was then added slowly in small portions and the flask vented to release the evolved nitrogen. After 30 minutes at 0° C., the reaction was stirred at room temperature for 8 hours. The reaction mixture was then filtered, washed with dry DCM, and the resin immobilized {4-[aza(triphenylylidene)methyl]phenyl}-N-[2-(2,4-dichlorophenyl) ethyl]carboxamide was dried in vacuo for 8 hours.

Step 2. Synthesis of Isocyanate from Carboxylic Acid

To 1 mmol of carboxylic acid dissolved in 5 ml of DCM was added 1 mmol of triethyl amine and 1 mmol of diphenylphosphorazidate. The reaction was then stirred under nitrogen for 30 minutes at 0° C. and then at 50° C. for 3 hours. The resulting mixture was then cooled to room temperature, concentrated in vacuo, and then dry THF was added to make up a stock solution of the isocyanate which was used without further purification.

Step 3. Synthesis of Carbodiimide

To resin bound phophinimine (1 mmol) suspended in dry THF was added 1 mmol of the isocyanate of step 3. The suspension was stirred for 8 hours at 17° C. in a capped vial.

Step 4. Synthesis of Guanidine

The reaction product of step 3 above was cooled to room temperature and 2 equivalents of cis-2,6-dimethylpiperazine were added. The reaction mixture was then heated at 70° C. with stirring for 2 hours and cooled. The resulting mixture was then filtered, washed with THF, and the combined filtrate was concentrated in vacuo and the residue purified by silica gel chromatography, eluting with 10% methanol in DCM with 2% triethyl amine. The final product was further purified by reversed phase HPLC.

HPLC: 7.92 minutes
MS: MH+=544.3

Example 52

Synthesis of [4-({1-((3S)-3-methylpiperazinyl)(1Z)-2-aza-2-[4-(trifluoromethyl)cyclohexyl]vinyl}amino)phenyl]-N-[2-(2,4-dichlorophenyl)ethyl]carboxamide Step 1. Synthesis of Immobilized{4-[aza(triphenylylidene)methyl]phenyl}-N-[2-(2,4-dichlorophenyl)ethyl]carboxamide 1 mmol of resin bound triphenylphosphine in a round-bottomed flask was suspended in THF and cooled to 0° C. with stirring. 1 mmol of the azide ([4-(azadiazomvinyl)phenyl]-N-[2-(2,4-dichlorophenyl)ethyl]carboxamide) was then added slowly in small portions and the flask vented to release the evolved nitrogen. After 30 minutes at 0° C., the reaction was stirred at room temperature for 8 hours. The resulting mixture was then filtered, washed with dry DCM, and the resin immobilized{4-[aza(triphenylylidene)methyl]phenyl}-N-[2-(2,4-dichlorophenyl)ethyl]carboxamide was dried in vacuo for 8 hours.

Step 2. Synthesis of Isocyanate from Carboxylic Acid

To 1 mmol of carboxylic acid dissolved in 5 ml of DCM was added 1 mmol of triethyl amine and 1 mmol of diphenylphosphorazidate. The reaction was then stirred under nitrogen for 30 minutes at 0° C. and then at 50° C. for 3 hours. The resulting mixture was then cooled to room temperature, concentrated in vacuo, and then dry THF was added to make up a stock solution of the isocyanate which was used without further purification.

Step 3. Synthesis of Carbodiimide

To resin bound phophinimine (1 mmol) suspended in dry THF was added 1 mmol of the isocyanate from step 2 above. The suspension was then stirred for 8 hours at 70° C. in a capped vial.

Step 4. Synthesis of Guanidine

The reaction product of step 3 above was cooled to room temperature and 2 equivalents (S)-(+)-2-methylpiperazine were added. The reaction mixture was then heated at 70° C. with stirring for 2 hours and cooled. The reaction mixture was then filtered, washed with THF, and the combined filtrate was concentrated in vacuo and the residue purified by silica gel chromatography, eluting with 10% methanol in DCM with 2% triethyl amine. The final product could be further purified with reversed phase HPLC.

HPLC: 7.59 minutes

MS: MH+=584.3

Example 53

Synthesis of (4-{[1-((3S)-3-methylpiperazinyl)(1Z)-2-aza-2-(3-methoxycyclohexyl)vinyl]amino}phenyl)-N-[2-(2,4-dichlorophenyl)ethyl]carboxamide Step 1. Synthesis of Immobilized{4-[aza(triphenylylidene)methyl]phenyl}-N-[2-(2,4-dichlorophenyl)ethyl]carboxamide 1 mmol of resin bound triphenylphosphine in a round-bottomed flask was suspended in THF and cooled to 0° C. with stirring. 1 mmol of the azide ([4-(azadiazomvinyl)phenyl]-N-[2-(2,4-dichlorophenyl)ethyl]carboxamide) was then added slowly in small portions and the flask vented to release the evolved nitrogen. After 30 minutes at 0° C., the reaction was stirred at room temperature for 8 hours. The reaction mixture was then filtered, washed with dry DCM, and the resin immobilized {4-[aza(triphenylylidene)methyl]phenyl}-N-[2-(2,4-dichlorophenyl) ethyl]carboxamide was dried in vacuo for 8 hours.

Step 2. Synthesis of Isocyanate from Carboxylic Acid

To 1 mmol of 3-methoxycyclohexanecarboxylic acid dissolved in 5 ml of DCM was added 1 mmol of triethyl amine and 1 mmol of diphenylphosphorazidate. The reaction mixture was then stirred under nitrogen for 30 minutes at 0° C. and then at 50° C. for 3 hours. The reaction mixture was then cooled to room temperature, concentrated in vacuo, and then dry THF was added to make up a stock solution of the isocyanate which was used without further purification.

Step 3. Synthesis of Carbodiimide

To resin bound phophinimine (1 mmol) suspended in dry THF was added 1 mmol of the isocyanate from step 2 above. The suspension was then stirred for 8 hours at 70° C. in a capped vial.

Step 4. Synthesis of Guanidine

The reaction product of step 3 above was cooled to room temperature and 2 equivalents of (S)-(+)-2-methylpiperazine were added. The reaction mixture was then heated at 70° C. with stirring for 2 hours and cooled. The resulting mixture was filtered, washed with THF, and the combined filtrate was concentrated in vacuo and the residue purified by silica gel chromatography, eluting with 10% methanol in DCM with 2% triethyl amine. The final product was further purified by reversed phase HPLC.

HPLC: 6.95 minutes

MS: MH+=546.3

Example 54

Synthesis of (4-{[1-((3S)-3-methylpiperazinyl)-2-((2S,3S,1S,5R)-2,6,6-trimethylbicyclo[3.1.1]hept-3-yl)(1Z)-2-azavinyl]amino}phenyl)-N-[2-(2,4-dichlorophenyl)ethyl]carboxamide Step 1. Synthesis of Immobilized{4-[aza(triphenylylidene)methyl]phenyl}-N-[2(2,4-dichlorophenyl)ethyl]carboxamide 1 mmol of resin bound triphenylphosphine in a round-bottomed flask was suspended in THF and cooled to OC with stirring. 1 mmol of the azide ([4-(azadiazomvinyl)phenyl]-N-[2-(2,4-dichlorophenyl)ethyl]carboxamide) was then added slowly in small portions and the flask vented to release the evolved nitrogen. After 30 minutes at 0° C., the reaction was stirred at room temperature for 8 hours. The resulting mixture was then filtered, washed with dry DCM, and the resin immobilized {4-[aza(triphenylylidene)methyl]phenyl}-N-[2-(2,4-dichlorophenyl) ethyl]carboxamide was dried in vacuo for 8 hours.

Step 2. Synthesis of Isocyanate from Amine Hydrochloride

To 1 g of (1S,2S,3S,5R)-(+)-isopinocampheylamine hydrochloride in a round-bottomed flask fitted with a reflux condenser, was added 6 ml of phosgene solution in toluene (20%). The resulting suspension was then heated to reflux (110° C.) until it turned clear (usually after about 2–8 hours). The solution was cooled and concentrated in vacuo, and the resulting isocyanate was either distilled or used as such.

Step 3. Synthesis of Carbodiimide

To resin bound phophinimine (1 mmol) suspended in dry THF was added 1 mmol of the isocyanate from step 2 above. The suspension was then stirred for 8 hours at 70° C. in a capped vial.

Step 4. Synthesis of Guanidine

The reaction product of step 3 above was cooled to room temperature and 2 equivalents of the (S)-(+)-2-methylpiperazine were added. The reaction mixture was heated at 70° C. with stirring for 2 hours and cooled. The resulting mixture was filtered, washed with THF, and the combined filtrate was concentrated in vacuo and the residue purified by silica gel chromatography, eluting with 10% methanol in DCM with 2% triethyl amine. The final product could be further purified with reversed phase HPLC.

HPLC: 8.68 minutes

MS: MH+=570

Example 55

Synthesis of (4-{[1-((3S)-3-methylpiperazinyl)(1Z)-2-aza-2-(2,2-dimethylcyclohexyl)vinyl]amino}phenyl)-N-[2-(2,4-dichlorophenyl)ethyl]carboxamide Step 1. Synthesis of Immobilized{4-[aza(triphenylylidene)methyl]phenyl}-N-[2-(2,4-dichlorophenyl)ethyl]carboxamide 1 mmol of resin bound triphenylphosphine in a round-bottomed flask was suspended in THF and cooled to 0° C. with stirring. 1 mmol of the azide ([4-(azadiazomvinyl)phenyl]-N-[2-(2,4-dichlorophenyl)ethyl]carboxamide) was then added slowly in small portions and the flask vented to release the evolved nitrogen. After 30 minutes at 0° C., the reaction was stirred at room temperature for 8 hours. The resulting mixture was then filtered, washed with dry DCM, and the resin immobilized {4-[aza(triphenylylidene)methyl]phenyl}-N-[2-(2,4-dichlorophenyl) ethyl]carboxamide was dried in vacuo for 8 hours.

Step 2. Synthesis of Isocyanate from Amine Hydrochloride

To 0.5 g of 2,2 dimethyl cyclohexamine hydrochloride in a round-bottomed flask fitted with a reflux condenser, was added 4.5 ml of phosgene solution in toluene (20%). The suspension was then heated to reflux (110° C.) until it turned clear (usually after about 2–8 hours). The solution was cooled and concentrated in vacuo, and the resulting isocyanate was either distilled or used as such.

Step 3. Synthesis of Carbodiimide

To resin bound phophinimine (1 mmol) suspended in dry THF was added 1 mmol of the isocyanate from step 2 above. The suspension was then stirred for 8 hours at 70° C. in a capped vial.

Step 4. Synthesis of Guanidine

The reaction product of step 3 above was cooled to room temperature and 1.2 equivalents of (S)-(+)-2-methylpiperazine were added. The reaction mixture was then heated at 70° C. with stirring for 2 hours and cooled. The resulting mixture was filtered, washed with THF, and the combined filtrate was concentrated in vacuo and the residue purified by silica gel chromatography, eluting with 10% methanol in DCM with 2% triethyl amine. The final product could be further purified with reversed phase HPLC.

HPLC: 7.93 minutes

MS: MH+=544

Example 56

Synthesis of (4-{[(1Z)-2-aza-2-(2,2-dimethylcyclohexyl)-1-(3,5-dimethylpiperazinyl) vinyl]amino}phenyl)-N-[2-(2,4-dichlorophenyl) ethyl]carboxamide Step 1. Synthesis of Immobilized{4-[aza(triphenylylidene) methyl]phenyl}-N-[2-(2,4-dichlorophenyl)ethyl] carboxamide 1 mmol of resin bound triphenylphosphine in a round-bottomed flask was suspended in THF and cooled to 0° C. with stirring. 1 mmol of the azide ([4-(azadiazomvinyl) phenyl]-N-[2-(2,4-dichlorophenyl)ethyl]carboxamide) was then added slowly in small portions and the flask vented to release the evolved nitrogen. After 30 minutes at 0° C., the reaction was stirred at room temperature for 8 hours. The reaction mixture was then filtered, washed with dry DCM, and the resin immobilized {4-[aza(triphenylylidene)methyl] phenyl}-N-[2-(2,4-dichlorophenyl) ethyl]carboxamide was dried in vacuo for 8 hours.

Step 2. Synthesis of Isocyanate from Amine Hydrochloride

To 0.5 g of 2,2 dimethyl cyclohexamine hydrochloride in a round-bottomed flask fitted with a reflux condenser, was added 4.5 ml of phosgene solution in toluene (20%). The resulting suspension was then heated to reflux (110° C.) until it turned clear (usually after about 2–8 hours). The solution was cooled and concentrated in vacuo, and the resulting isocyanate was either distilled or used as such.

Step 3. Synthesis of Carbodiimide

To resin bound phophinimine (1 mmol) suspended in dry THF was added 1 mmol of the isocyanate from step 2 above. The suspension was then stirred for 8 hours at 70° C. in a capped vial.

Step 4. Synthesis of Guanidine

The reaction product of step 3 above was cooled to room temperature and 1.2 equivalents of 2,6-dimethylpiperazine were added. The reaction mixture was then heated at 70° C. with stirring for 2 hours and cooled. The resulting mixture was filtered, washed with THF, and the combined filtrate was concentrated in vacuo and the residue purified by silica gel chromatography, eluting with 10% methanol in DCM with 2% triethyl amine. The final product could be further purified with reversed phase HPLC.

HPLC: 8.10 minutes

MS: MH+=558.6

Example 57

Synthesis of (4-{[(1Z)-2-aza-1-(3,5-dimethylpiperazinyl)-2-(2,6,6-trimethylbicyclo [3.1.1]hept-3-yl)vinyl]amino}phenyl)-N-[2-(2,4-dichlorophenyl)ethyl]carboxamide Step 1. Synthesis of Immobilized{4-[aza(triphenylylidene) methyl]phenyl}-N-[2-(2,4-dichlorophenyl)ethyl] carboxamide 1 mmol of resin bound triphenylphosphine in a round-bottomed flask was suspended in THF and cooled to 0° C. with stirring. 1 mmol of the azide ([4-(azadiazomvinyl) phenyl]-N-[2-(2,4-dichlorophenyl)ethyl]carboxamide) was then added slowly in small portions and the flask vented to release the evolved nitrogen. After 30 minutes at 0° C., the reaction was stirred at room temperature for 8 hours. The resulting mixture was then filtered, washed with dry DCM, and the resin immobilized {4-[aza(triphenylylidene)methyl] phenyl}-N-[2-(2,4-dichlorophenyl) ethyl]carboxamide was dried in vacuo for 8 hours.

Step 2. Synthesis of Isocyanate from Amine Hydrochloride

To 1 g of isopinocampheylamine hydrochloride in a round-bottomed flask fitted with a reflux condenser, was added 8 ml of phosgene solution in toluene (20%). The resulting suspension was then heated to reflux (110° C.) until it turned clear (usually after about 2–8 hours). The solution was cooled and concentrated in vacuo and the resulting isocyanate was either distilled or used as such.

Step 3. Synthesis of Carbodiimide

To resin bound phophinimine (1 mmol) suspended in dry THF was added 1 mmol of the isocyanate from step 2 above. The suspension was stirred for 8 hours at 70° C. in a capped vial.

Step 4. Synthesis of Guanidine

The reaction product of step 3 above was cooled to room temperature and 1.2 equivalents of 2,6-dimethylpiperazine were added. The resulting reaction mixture was heated at 70° C. with stirring for 2 hours and cooled. The resulting reaction mixture was filtered, washed with THF, and the combined filtrate was concentrated in vacuo and the residue purified by silica gel chromatography, eluting with 10% methanol in DCM with 2% triethyl amine. The final product could be further purified with reversed phase HPLC.

HPLC: 8.83 minutes

MS: MH+=584.6

Example 58

Synthesis of (4-{[1-((3S)-3-methylpiperazinyl)(1Z)-2-aza-2-(2,6,6-trimethylbicyclo[3.1.1]hept-3-yl) vinyl]amino}phenyl)-N-[2-(2,4-dichlorophenyl) ethyl]carboxamide Step 1. Synthesis of Immobilized{4-[aza(triphenylylidene) methyl]phenyl}-N-[2-(2,4-dichlorophenyl)ethyl] carboxamide 1 mmol of resin bound triphenylphosphine in a round-bottomed flask was suspended in THF and cooled to 0° C. with stirring. 1 mmol of the azide ([4-(azadiazomvinyl) phenyl]-N-[2-(2,4-dichlorophenyl)ethyl]carboxamide) was then added slowly in small portions and the flask vented to release the evolved nitrogen. After 30 minutes at 0° C., the reaction was stirred at room temperature for 8 hours. The resulting mixture was then filtered, washed with dry DCM, and the resin immobilized {4-[aza(triphenylylidene)methyl] phenyl}-N-[2-(2,4-dichlorophenyl) ethyl]carboxamide was dried in vacuo for 8 hours.

Step 2. Synthesis of Isocyanate from Amine Hydrochloride

To 1 g of isopinocampheylamine hydrochloride in a round-bottomed flask fitted with a reflux condenser was added 8 ml of phosgene solution in toluene (20%). The resulting suspension was then heated to reflux (110° C.) until it turned clear (usually after about 2–8 hours). The solution was cooled and concentrated in vacuo, and the resulting isocyanate was either distilled or used as such.

Step 3. Synthesis of Carbodiimide

To resin bound phophinimine (1 mmol) suspended in dry THF was added 1 mmol of the isocyanate from step 2 above. The suspension was then stirred for 8 hours at 70° C. in a capped vial.

Step 4. Synthesis of Guanidine

The reaction product of step 3 above was cooled to room temperature and 1.2 equivalents of (S)-(+)-2-methylpiperazine were added. The resulting reaction mixture was heated at 70° C. with stirring for 2 hours and cooled. The resulting mixture was then filtered, washed with THF, and the combined filtrate was concentrated in vacuo and the residue purified by silica gel chromatography, eluting with 10% methanol in DCM with 2% triethyl amine. The final product could be further purified with reversed phase HPLC.

HPLC: 8.73 minutes
MS: MH+=570.6

Example 59

Synthesis of (4-{[1-((3S,5S)-3,5-dimethylpiperazinyl)(1Z)-2-aza-2-(4-methylcyclohexyl)vinyl]amino}phenyl)-N-[2-(2,4-dichlorophenyl)ethyl]carboxamide Step 1. Synthesis of Immobilized{4-[aza(triphenylylidene)methyl]phenyl}-N-[2-(2,4-dichlorophenyl)ethyl]carboxamide 1 mmol of resin bound triphenylphosphine in a round-bottomed flask was suspended in THF and cooled to 0° C. with stirring. 1 mmol of the azide ([4-(azadiazomvinyl)phenyl]-N-[2-(2,4-dichlorophenyl)ethyl]carboxamide) was then added slowly in small portions and the flask vented to release the evolved nitrogen. After 30 minutes at 0° C., the reaction was stirred at room temperature for 8 hours. The resulting mixture was then filtered, washed with dry DCM, and the resin immobilized {4-[aza(triphenylylidene)methyl]phenyl}-N-[2-(2,4-dichlorophenyl) ethyl]carboxamide was dried in vacuo for 8 hours.

Step 2. Synthesis of Isocyanates from Carboxylic Acids

To 1 mmol of trans-4-methylcyclohexanecarboxylic acid dissolved in 5 ml of DCM was added 1 mmol of triethyl amine and 1 mmol of diphenylphosphorazidate. The reaction was then stirred under nitrogen for 30 minutes at 0° C. and then at 50° C. for 3 hours. The reaction was then cooled to room temperature, concentrated in vacuo, and then dry THF was added to make up a stock solution of the isocyanate which was used without further purification.

Step 3. Synthesis of Carbodiimide

To resin bound phophinimine (1 mmol) suspended in dry THF, was added 1 mmol of the isocyanate from step 2 above. The suspension was then stirred for 8 hours at 70° C. in a capped vial.

Step 4. Synthesis of Guanidine

The reaction product of step 3 above was cooled to room temperature and 1.2 equivalents of (2S,6S)-2,6-dimethylpiperazine (synthesized as in E. Jon Jacobson et al., *J. Org. Chem.*, 60, 4177–83 (1995)) were added. The reaction mixture was heated at 70° C. with stirring for 2 hours and cooled. The resulting mixture was filtered, washed with THF, and the combined filtrate was concentrated in vacuo and the residue purified by silica gel chromatography, eluting with 10% methanol in DCM with 2% triethyl amine. The final product could be further purified with reversed phase HPLC.

HPLC: 8.21 minutes
MS: MH+=544.5

Example 60

Synthesis of (acetyloxy)methyl (2S)-4-((E)-{[4-({[2-(2,4-dichlorophenyl)ethyl]amino}carbonyl)phenyl]amino}{[(1S,2S,3S,5R)-2,6,6-trimethyl bicyclo[3.1.1]hept-3-yl]imino}methyl)-2-methylpiperazine-1-carboxylate The synthesis of the above-named compound was accomplished by acylating the product prepared in Example 54 using the conditions set forth in J. Alexander et al. *J. Med. Chem.*, 31, 318–322 (1988).

Examples 61–113

Examples 61–113 in the table below were synthesized in a manner similar to the above-described procedures (e.g. Example 8) or according to the following general procedures.

General Synthesis of Carboxamides

To a solution of an amine (1.0 equivalent) and 4-azidobenzoic acid (1.0 equivalent) or 4-nitrobenzoic acid (1.0 equivalent) in THF was added EDCl (1.5 equivalent), and the mixture was stirred at room temperature (8–12 hours). THF was removed and the residue was resuspended in ethyl acetate, washed with water, dried with sodium sulfate, concentrated, and purified by silica gel chromatography eluting with ethyl acetate/hexane or chloroform/methanol.

General Synthesis of Guanidines
A. From Azidocarboxamides

To a solution of the corresponding azido carboxamide (1.0 equivalent) in THF was added triphenylphosphine (1.0 equivalent) at room temperature. After 8 hours, the corresponding isocyanate was added (1.3 equivalents) and the solution was heated at 55–80° C. overnight. To the mixture was added an amine (1.3 equivalents). After being heated at the same temperature for 2 hours, THF was removed. The residue was resuspended in ethyl acetate, washed with water, dried over anhydrous sodium sulfate, concentrated, and purified by silica gel chromatography(CHCl$_3$/MeOH 90:10+ 0.1% Et$_3$N 2% Et$_3$N). The final products could be further purified with reversed phase HPLC.

B. From Nitrocarboxamides

The nitrocarboxamide was taken up in ethanol (or methanol) and purged with dry nitrogen. To this solution was introduced activated Pd/C (10% w/w, 0.1 equivalent) and the mixture was hydrogenated for about 30 minutes or until complete by LC/MS. The mixture was then filtered through Celite, concentrated in vacuo, and taken on crude to the next step.

To a 0.5 M acetone solution (0° C. ice bath) containing the amine (1 equivalent) and sodium carbonate (3 equivalents) was added thiophosgene (3 equivalents) dropwise. After two hours at room temperature, the reaction mixture was concentrated in vacuo to remove solvent and excess thiophosgene. The residue was taken up in ethyl acetate and washed with water, dried with sodium sulfate, and then concentrated in vacuo to yield the isothiocyanate. To a solution of the resulting isothiocyanate in dry THF (0.5 M solution) was added an amine (1.5 equivalents). After stirring overnight, the reaction mixture was concentrated in vacuo and the thiourea product was dissolved in ethyl acetate or DCM and purified via flash chromatography.

To a solution of the thiourea in dry THF (0.1 M) was added EDC (2equivalents) and the solution was heated at reflux (~80° C. external temp.) for 60 minutes, after which it was cooled to room temperature and then placed in an ice bath for 15 minutes with stirring. A DCM solution containing an amine (2 equivalents) was added and the reaction was stirred at room temperature. After 20 minutes, the reaction was diluted with ethyl acetate and washed with water. The aqueous layer was back extracted with ethyl acetate and the combined organic layers, after concentration in vacuo, was purified by silica gel flash chromatography (typically eluting first with 10% MeOH in DCM followed by an addition of 2% triethyl amine to the mobile phase) and/or reverse phase prep-HPLC.

Starting Materials and Intermediates

The requisite starting materials and intermediates corresponding to the examples in the tables are commercially available or may be synthesized by methods familiar to one of skill in the art, by procedures shown in the preceding examples, or by the following procedures.

Preparation of Non-commercial Phenylethylamines

Phenyethyl amines used in the synthesis of Examples 83, 87 and 88 may be prepared as described in J. Weinstock et al., *J. Med. Chem.* 1166–1176 (1987), replacing nitromethane respectively with nitroethane, nitropropane and nitrobutane.

Preparation of [2S or R]-2-amino-3-[2, 4dichlorophenyl]propan-1-ol

Prepared from L or D 2,4 dichlorphenylalanine following the procedure as given in *J. Org. Chem.*, 65, No. 16, pp 503 (2000).

Preparation of 6-chloro-3,4-dihydro-1H-naphthalen-2-one

Prepared according to *Journal of Amer. Chem. Soc.*, 119, 12722–12726 (1997) and *Org Synthesis*, 51, pp 109 (1971).

Preparation of 6-chloro-1,2,3,4-tetrahydro-naphthalen-2-ylamine

Aza [6-chloro (2-1,2,3,4-tetrahydronaphthyl)]diazo methane may be prepared according to *J. Org. Chem.*, 60, 4324–4330 (1995) (following the prescribed procedure except that the mesylate intermediate was converted to azide without purification on silica gel column). Aza [6-chloro (2-1,2,3,4-tetrahydronaphthyl)]diazo methane (1.0 equivalent) was then dissolved in THF to which triphenylphosphine (1.0 equivalent) was added and reaction mixture allowed to stir at 70° C. for 1 hour. Thereafter, 5% KOH was poured and further THF was added to make one phase and the solution was stirred for another 1 hour at 70° C. All the THF was removed and the KOH layer was extracted with $CHCl_3$ (3×). Combined organic extracts were washed with 1N HCl (2×) and organic phase was discarded. The aqueous layer was further treated with 5% KOH (5 ml) and amine so formed was extracted in $CHCl_3$ washes (3×). $CHCl_3$ extracts were further washed with brine and dried over $Na_2SO_4$. The removal of solvent in vacuo gave the pure amine.

Preparation of 6-fluoro-3,4-dihydro-1H-naphthalen-2-one 4-fluorophenylacetic acid (1 equivalent) was dissolved in dichloroethane (1.3 M) containing $SOCl_2$ (3 equivalents), the mixture was refluxed for 90 minutes and the solvent was removed. Solution of this crude product in $CH_2Cl_2$ was added dropwise within 60 minutes to $AlCl_3$ (2 eq) in $CH_2Cl_2$ (0.4 M) while stirring at 0° C. Thereafter, ethylene was introduced at 0° C. over 45 minutes, whereupon the mixture was stirred further at room temperature for 1 hour, and thereafter was treated at 0° C. with ice-water. The organic phase was washed with 1N HCl (2×), $NaHCO_3$ (sat. sol.), dried and evaporated. The residue was triturated with hexane, yielding the product as a bright yellow solid.

Preparation of 6-fluoro-1,2,3,4-tetrahydro-naphthalen-2-ylamine

Over a solution of 6-fluorotetralone (6-fluoro-3,4-dihydro-1 H-naphthalen-2-one; 1 equivalent) and ammonium acetate (5 equivalents) in a 2:1 mixture of MeOH:THF (0.24 M), was carefully added $NaCNBH_3$ (2 eq), and the reaction mixture was stirred at room temperature for 2 hours. Concentrated HCl was added at 0° C. until the pH was less than 2, and the MeOH was removed in vacuo. The residue was taken up in water and extracted with $CHCl_3$ (2×). The aqueous solution was basified with solid KOH and extracted with $CHCl_3$ (3×). The combined extracts were dried ($MgSO_4$) and evaporated in vacuo to give the titled compound.

Preparation of 2-(4-bromo-2-fluoro) Nitrostyrene

4-Bromo-2-fluorobenzaldehyde 1 (1 equivalent) was dissolved in anhydrous methanol (0.3 M) and nitromethane (1 equivalent) was added and the reaction was chilled in ice. Excess DBU (11.04 mL, 73.8 mmol) was added dropwise to the reaction and stirring continued at 0° C. for 25 minutes. The reaction was then poured into 180 mL of 3 M HCl (22 equivalents). A solid precipitated out and was collected by filtration. The yellow solid was redissolved in ether and dried over $Na_2SO_4$, filtered and concentrated to afford 2-(4-bromo-2-fluoro)nitrostyrene as a yellow solid. MS: 247.9 (M+H).

Preparation of 2-(4-bromo-2-fluorophenyl) ethylamine

4-Bromo-2-fluoronitro styrene (1 equivalent) in THF (0.2 M) was cooled to 0° C. and treated with 1.0 M $BH_3$ in THF (5 equivalents). The reaction was heated to reflux overnight. The reaction was cooled to 0° C. and quenched with $H_2O$ then 1 N HCl until a pH of about 2 was achieved. The reaction was stirred for 30 minutes at room temperature and then extracted with ether (3×). The aqueous layer was made basic with 5% NaOH solution. The aqueous layer was then extracted into ether (3×). The combined organic layers were washed with brine, dried over $Na_2SO_4$, filtered, and concentrated to give crude 2-(4-bromo-2-fluorophenyl) ethylamine. Purification by flash chromatography eluting with 2%–5%–10% MeOH/$CH_2Cl_2$ gradients containing 1% concentrated ammonia afforded the desired compound. MS m/z 219.8 (M+H).

Preparation of 6-azido-N-[2-(2,4-dichlorophenyl) ethyl]pyridine-3-carboxamide

6-Chloro-N-[2-(2,4-dichlorophenyl)ethyl]pyridine-3-carboxamide (1 equivalent) and sodium azide (2.6 equivalents) were suspended in anhydrous DMSO (0.6 M) under nitrogen. The mixture was heated at 100° C. for four days. Ethyl acetate was added and the organic phase washed with water and brine, dried over anhydrous sodium sulfate, and filtered. The filtrate was evaporated to dryness and the resultant residue dissolved in a 1:1 ethyl acetate/DCM mixture. This solution was purified by flash chromatography over silica (1:1 ethyl acetate/DCM). The fractions coeluting with the major band (Rf 0.53, eluent: 1:1 ethyl acetate/DCM) were combined and evaporated to dryness. The residue was recrystallized from acetonitrile to give 6-azido-N-[2-(2,4-dichlorophenyl)ethyl]-pyridine-3-carboxamide as pale yellow needles. LCMS (MH+) 336.

Preparation of 4-Azido-N-[2-(2-fluoro-4-methoxy-phenyl)-ethyl]-benzamide

Step 1.

2-Fluoro-4-methoxy-benzaldehyde (1 equivalent) was dissolved in MeOH and chilled in an ice bath. Nitromethane (1 equivalent) was added. NaOH (1.05 equivalents) in water was added dropwise to the nitromethane/aldehyde solution, such that the temperature did not rise above 15° C. The reaction was then allowed to stir at 0° C. for 15 minutes. The reaction mixture was poured into concentrated HCl diluted with water. Product was extracted with EtOAc and washed with water, brine, and dried ($Na_2SO_4$). Solvent was removed to yield a yellow oil which was freeze-dried in 90% MeCN/$H_2O$ to give the product 2-fluoro-4-methoxy-1-(2-nitrovinyl)-benzene, which was used without further purification.

Step 2.

$LiAlH_4$ (3.5 equivalents) was suspended in THF and brought to reflux. 2-fluoro-4-methoxy-1-(2-nitro-vinyl)-benzene (1 equivalent) was dissolved in THF and added dropwise to the $LiAlH_4$. The reaction was allowed to proceed at reflux overnight. The reaction was then cooled in an ice bath and $H_2SO_4$ was added dropwise. The reaction was extracted with ether. The ether fractions were discarded. The aqueous layer was adjusted to pH 12 with 5% NaOH and extracted with ether (3×). Combined ether fractions were washed with brine and dried over $Na_2SO_4$. Solvent was removed to yield 2-(2-fluoro-4-methoxy-phenyl)-ethylamine as an oil, which was used without further purification.

Step 30

4-Azidobenzoic acid (1.5 equivalents) was dissolved in THF. EDC (1.5 equivalents), DIEA (1.5 equivalents) and DMAP (0.1 equivalents) were added followed by 2-(2-fluoro-4-methoxy-phenyl)-ethylamine (1 equivalent). The reaction was then allowed to stir overnight at room temperature. EtOAc was added and the reaction was washed with 10% citric acid, 10% sodium bicarbonate and brine. After drying over $Na_2SO_4$, solvent was removed and the residue was purified by flash chromatography 20% EtOAc/DCM to yield the title compounds as a white powder.

Preparation of 7-Methoxy-2,3,4,5-tetrahydro-1 H-benzo[d]azepine

Step 1.

2-(3-Methoxy-phenyl)-ethylamine (1 equivalent) was dissolved in anhydrous DCM (0.88 M) in a three necked round-bottomed flask under $N_2$ and stirred in an ice bath. Tosyl chloride (1.25 equivalents) was then dissolved in anhydrous DCM under $N_2$ and added to the stirring solution over 10 minutes (Caution! Exothermic reaction). A precipitate formed, DIEA (1.2 equivalents) was then added, and the reaction was stirred at room temperature overnight. The reaction was then washed with 10% citric acid, 10% sodium carbonate, and brine before being dried over sodium sulfate. The organic solvent was then removed under reduced pressure to leave a brown oil. This crude material was then purified via flash chromatography using 100% DCM running solvent to recover the product sulfonamide. (MH+) 306.1.

Step 2.

The Sulfonamide (1 equivalent) was dissolved in acetone and stirred in a round-bottomed flask with $K_2CO_3$ (6.9 equivalents). This was warmed to 78° C. and refluxed, ethyl bromoacetate (1.5 equivalents) was then added, and the reaction was allowed to proceed overnight. The $K_2CO_3$ was then filtered off and the solvent removed under reduced pressure. To this colorless oil was added NaOH (4.4 equivalents) dissolved in 50% EtOH (0.4 M) and then warmed to reflux at 90° C. and allowed to proceed overnight. The EtOH was then removed under reduced pressure. The residual oil was then washed with water and extracted with diethyl ether. The aqueous layer was then acidified with concentrated HCl and extracted with diethyl ether (2×). The organic layers were then combined and extracted with sodium carbonate (2×). The aqueous layers were then combined and acidified with concentrated HCl and extracted with diethyl ether (2×). The organic layers were then combined and dried over sodium sulfate. The organic solvent was then removed under reduce pressure. This material was then recrystallized from ethyl acetate/petroleum spirit to recover the alkylated product [[2-(3-Methoxy-phenyl)-ethyl]-(toluene-4-sulfonyl)-amino]-acetic acid. (MH+) 363.9.

Step 3.

[[2-(3-Methoxy-phenyl)-ethyl]-(toluene-4-sulfonyl)-amino]-acetic acid (1 equivalent) was dissolved in anhydrous DCM (0.13 M) and added to a stirring solution of $P_2O_5$ (5 equivalents) suspended in anhydrous DCM (0.13 M) at 0° C. under nitrogen. This reaction was then allowed to proceed at room temperature for two days before being worked up. The reaction mixture was then diluted with 3% NaOH and extracted with DCM. The organic layers were then combined and dried over sodium sulfate and the solvent removed under reduced pressure to recover the cyclized product 8-methoxy-3-(toluene-4-sulfonyl)-2,3,4,5-tetrahydro-benzo[d]azepin-1-one. Note the formation of the regio-isomer (ortho cyclized product). This material was then purified via flash chromatography using 20% acetone/petroleum spirit running solvent. Two separate fractions of the desired isomeric pure 8-methoxy-3-(toluene-4-sulfonyl)-2,3,4,5-tetrahydro-benzo[d]azepin-1-one were recovered. These two fractions were treated separately for the next reaction. (MH+) 346.1.

Step 4.

The ketone product from step 3 was dissolved in neat TFA and stirred under nitrogen. To this stirring solution was added triethylsilane (2.2 equivalents) and the reaction allowed to proceed overnight at room temperature. Aqueous sodium carbonate was then added and the solution extracted with ether (2×). The ether layers were then combined and dried over sodium sulfate and the solvent removed under reduced pressure to recover an orange oil. The crude material from the two reactions were then combined and purified via flash chromatography using 20% acetone/1% ammonia solution/petroleum spirit to give 7-methoxy-3-(toluene-4-sulfonyl)-2,3,4,5-tetrahydro-1 H-benzo[d]azepine. (MH+) 178.0.

Step 5.

Gaseous ammonia was first condensed into an oven-dried three necked round-bottomed flask in a dry ice/acetone bath under $N_2$. Sodium metal was then added to this vigorously stirring liquid ammonia to form sodium amide. Note the solution should hold a deep blue color to confirm that the liquid ammonia is anhydrous. The sulfonamide (1 equivalent) from step 4 was then dissolved in THF (0.1 M) in an oven-dried round-bottomed flask connected to a dry ice condenser. The anhydrous liquid ammonia was then distilled across into the round-bottomed flask containing the sulfonamide with vigorous stirring via the dry ice condenser connected in a series under a steady stream of $N_2$. Once the distillation had finished, the condenser and flask containing the sulfonamide was isolated. Sodium metal (2.1 equivalents) was then added until the solution again went a deep blue color. The reaction was stirred for a further 30 minutes before being quenched with $NH_4Cl$ (9.3 equivalents). The reaction was then extracted with diethyl ether and dried over sodium sulfate and the solvent removed under reduced pressure to give the product amine as a yellow oil. (MH+) 353.3.

Preparation of (4-Azido-phenyl)-(7-methoxy-1,2,4,5-tetrahydro-benzo[d]azepin-3-yl)-methanone 7-Methoxy-2,3,4,5-tetrahydro-1 H-benzo[d]azepine (1 equivalent) was dissolved in THF (0.1 M) along with azidobenzoic acid (1.5 equivalents), EDC (1.5 equivalents), DMAP (0.18 equivalents), and DIEA (1.5 equivalents). The reaction was stirred at room temperature overnight. The reaction was then washed with 10% citric acid, saturated sodium carbonate, and brine. The organic layer was then dried over sodium sulfate and the organic solvent removed under reduced pressure. The material was then purified via flash chromatography using 8% acetone/1% ammonia solution/petroleum spirit running solvent to give the title compound. (MH+) 323.2.

Preparation of 5-Methoxy-2-indamine

Step 1.

A mixture of 4-methoxyphenylacetic acid (1 equivalent), freshly distilled thionyl chloride (5.6 equivalents) and DMF was heated at reflux for 30 minutes. The mixture was allowed to cool and evaporated to dryness to give an orange oil. The crude product was used for the next step without further purification. A diazomethane solution was cooled in an ice bath. A solution of the crude product from the previous step in ether was added slowly. The flask was fitted with a calcium chloride drying tube and allowed to stand at room temperature for 16 hours. The mixture was evaporated to dryness by bubbling nitrogen through the reaction mixture with external heating at 30° C. The residue was purified by flash chromatography over silica (DCM, 5% ethyl acetate/DCM). The fractions coeluting with the major band were combined and evaporated to dryness to give 1-diazo-3-(4-methoxyphenyl)propan-2-one as an orange oil. (MH+) 191.

Step 2.

A solution of 1-diazo-3-(4-methoxyphenyl)propan-2-one (1 equivalent) in anhydrous DCM (0.1 M) was prepared under nitrogen. A suspension of rhodium (II) acetate dimer (0.02 equivalents) in anhydrous DCM (0.01 M) was prepared under nitrogen. The diazoketone solution was transferred to the rhodium acetate dimer suspension via cannula and the mixture stirred at room temperature for 90 minutes. The mixture was filtered (Whatmann No 1 filter paper) and the filtrate evaporated to dryness. The residue was purified by flash chromatography over silica (eluent DCM). The fractions coeluting with the major non-polar band (Rf 0.62) were combined and evaporated to dryness to give 5-methoxy-2-indanone as a yellow solid. (MH+) 162.

Step 3.

A mixture of 5-methoxy-2-indanone (1 equivalent) and methoxyamine hydrochloride (2.5 equivalents) was dissolved in a 1:1 mixture (0.24 M) of ethanol and pyridine. The mixture was heated at reflux for 30 minutes and allowed to cool. Water was added and the mixture was extracted with ethyl acetate. The ethyl acetate extracts were dried over anhydrous sodium sulfate and filtered. The filtrate was evaporated to dryness to give an orange oil which was used for the next step without further purification. The crude product from the previous step was dissolved in anhydrous THF under $N_2$. A borane-THF complex solution (1.0M, 4.7 equivalents) was added and the mixture heated at reflux under $N_2$ for 3 hours. Methanol was added and the mixture evaporated to dryness. HCl (3M, 24 equivalents) was added to the residue and the mixture heated at 90° C. for 1 hour. NaOH solution (10M, 25 equivalents) was added and the aqueous phase extracted with ethyl acetate (3x). The combined ethyl acetate extracts were dried over anhydrous sodium sulfate and filtered. The filtrate was evaporated to dryness and the residue purified by flash chromatography over silica (eluent 10% methanol, 1% concentrated ammonia solution in DCM). The fractions coeluting with the major band (Rf 0.31, eluent: 10% methanol, 1% concentrated ammonia solution in DCM, bands visualized by spraying with Ninhydrin and heating) were combined and evaporated to dryness to give 5-methoxy-2-indamine as a pale brown oil. (MH+) 164.2.

Table of Examples 61–113

| Example | Name | MH+ |
|---|---|---|
| 61 | 4-{[(Z)-(cyclopentylimino)(piperazin-1-yl)methyl]amino}-N-[2-(2,4-dichlorophenyl)ethyl]benzamide | 488 |
| 62 | 4-{[(Z)-(cyclopentylimino)(1,4-diazepan-1-yl)methyl]amino}-N-[2-(2,4-dichlorophenyl)ethyl]benzamide | 502 |
| 63 | N-[2-(2,4-dichlorophenyl)ethyl]-4-({(E)-[(3-methylcyclohexyl)imino][(3S)-3-methylpiperazin-1-yl]methyl}amino)benzamide | 530.5 |
| 64 | N-[2-(2,4-dichlorophenyl)ethyl]-4-{[(E)-[(3S)-3-methylpiperazin-1-yl](tricyclo[3.3.1.1~3,7~]dec-2-ylimino)methyl]amino}benzamide | 544.5 |
| 65 | N-[2-(2,4-dichlorophenyl)ethyl]-4-[((Z)-[(3S)-3-methylpiperazin-1-yl]{[4-(trifluoromethyl)cyclohexyl]imino}methyl)amino]benzamide | 584.4 |
| 66 | N-[2-(2,4-dichlorophenyl)ethyl]-4-({(E)-[(3S)-3-methylpiperazin-1-yl][(2-propylcyclohexyl)imino]methyl}amino)-benzamide | 558 |
| 67 | N-[2-(2,4-dichlorophenyl)ethyl]-4-({(E)-[(3R,5S)-3,5-dimethylpiperazin-1-yl][(2-propylcyclohexyl)imino]methyl}amino)-benzamide | 572.3 |
| 68 | N-[2-(2,4-dichlorophenyl)ethyl]-4-{[(E)-[(3S)-3-methylpiperazin-1-yl](tricyclo[3.3.1.1~3,7~]dec-2-ylimino)methyl]amino}benzamide | 568 |
| 69 | N-[2-(2,4-dichlorophenyl)ethyl]-4-({(E)-[(3R,5S)-3,5-dimethylpiperazin-1-yl][(1,7,7-trimethylbicyclo[2.2.1]hept-2-yl)imino]methyl}amino)benzamide | 584.3 |
| 70 | N-[2-(2,4-dichlorophenyl)ethyl]-4-({(E)-[(3S)-3-methylpiperazin-1-yl][(1,1,7-trimethylbicyclo[2.2.1]hept-2-yl)imino]methyl}amino)benzamide | 570.3 |
| 71 | N-[2-(2,4-difluorophenyl)ethyl]-4-({(E)-[(4-methylcyclohexyl)imino][(3S)-3-methylpiperazin-1-yl]methyl}amino)benzamide | 498.2 |
| 72 | N-[2-(2,4-dichlorophenyl)ethyl]-4-[((E)-[(3S)-3-methylpiperazin-1-yl]{[(1S,2R,3S,6R)-3,7,7-trimethylbicyclo[4.1.0]hept-2-yl]imino}methyl)amino]benzamide | 570.1 |

Table of Examples 61–113

| Example | Name | MH+ |
|---|---|---|
| 73 | N-[2-(2,4-dichlorophenyl)ethyl]-4-({(Z)-[(3R,5S)-3,5-dimethylpiperazin-1-yl][(4-ethylcyclohexyl)imino]methyl}amino)benzamide | 558.2 |
| 74 | 6-({(Z)-(cyclohexylimino)[(3S)-3-methylpiperazin-1-yl]methyl}amino)-N-[2-(2,4-dichlorophenyl)ethyl]pyridine-3-carboxamide | 517 |
| 75 | N-[2-(2,4-dichlorophenyl)ethyl]-4-({(E)-[(4-ethylcyclohexyl)imino][(3S)-3-methylpiperazin-1-yl]methyl}amino)benzamide | 544.2 |
| 76 | 4-({(Z)-(cyclohexylimino)[(3S)-3-methylpiperazin-1-yl]methyl}amino)-N-[2-(2,4-dichlorophenyl)-1-methylethyl]benzamide | 530.2 |
| 77 | N-{2-[2,4-bis(methyloxy)phenyl]ethyl}-4-({(Z)-[(4-methylcyclohexyl)imino][(3S)-3-methylpiperazin-1-yl]methyl}amino)benzamide | 522.4 |
| 78 | N-[2-(2,4-dichlorophenyl)-1-methylethyl]-4-({(Z)-[(4-methylcyclohexyl)imino][(3S)-3-methylpiperazin-1-yl]methyl}amino)benzamide | 544.2 |
| 79 | N-[2-(2,4-dichlorophenyl)ethyl]-4-{[(Z)-[(3R,5S)-3,5-dimethylpiperazin-1-yl]({(1S,2S)-2-[(phenylmethyl)oxy]cyclohexyl}imino)-methyl]amino}benzamide | 636.2 |
| 80 | N-[2-(2,4-dichlorophenyl)ethyl]-6-({(E)-[(4-methylcyclohexyl)imino][(3S)-3-methylpiperazin-1-yl]methyl}amino)pyridine-3-carboxamide | 531.2 |
| 81 | 4-({(Z)-(cyclohexylimino)[(3S)-3-methylpiperazin-1-yl]methyl}amino)-N-[2-(2,4-dimethylphenyl)ethyl]benzamide | 476 |
| 82 | N-{2-[2,4-bis(methyloxy)phenyl]ethyl}-4-[((Z)-[(3S)-3-methylpiperazin-1-yl]{[(1S,2S,3S,5R)-2,6,6-trimethylbicyclo[3.1.1]hept-3-yl]imino}methyl)amino]benzamide | 562.2 |
| 83 | N-[2-(2,4-dichlorophenyl)-1-methylethyl]-4-[((Z)-[(3S)-3-methylpiperazin-1-yl]{[(1S,2S,3S,5R)-2,6,6-trimethylbicyclo[3.1.1]hept-3-yl]imino}methyl)amino]benzamide | 584.2 |
| 84 | N-[2-(2,4-dimethylphenyl)ethyl]-4-[((E)-[(3S)-3-methylpiperazin-1-yl]{[(1S,2S,3S,5R)-2,6,6-trimethylbicyclo[3.1.1]hept-3-yl]imino}methyl)amino]benzamide | 530 |
| 85 | N-[2-(2,4-dimethylphenyl)ethyl]-4-[((E)-(3,5-dimethylpiperazin-1-yl){[(1S,2S,3S,5R)-2,6,6-trimethylbicyclo[3.1.1]hept-3-yl]imino}methyl)amino]benzamide | 544 |
| 86 | N-[2-(2,4-dichlorophenyl)ethyl]-6-[((E)-[(3S)-3-methylpiperazin-1-yl]{[(1S,2S,3S,5R)-2,6,6-trimethylbicyclo[3.1.1]hept-3-yl]imino}methyl)amino]pyridine-3-carboxamide | 571.2 |
| 87 | N-{1-[(2,4-dichlorophenyl)methyl]propyl}-4-[((Z)-[(3S)-3-methylpiperazin-1-yl]{[(1S,2S,3S,5R)-2,6,6-trimethylbicyclo[3.1.1]hept-3-yl]imino}methyl)amino]benzamide | 598.2 |
| 88 | N-{1-[(2,4-dichlorophenyl)methyl]butyl}-4-[((Z)-[(3S)-3-methylpiperazin-1-yl]{[(1S,2S,3S,5R)-2,6,6-trimethylbicyclo[3.1.1]hept-3-yl]imino}methyl)amino]benzamide | 612.2 |
| 89 | 4-[((Z)-[(3S)-3-methylpiperazin-1-yl]{[(1S,2S,3R,5R)-2,6,6-trimethylbicyclo[3.1.1]hept-3-yl]imino}methyl)amino]-N-[(2S)-2-phenylpropyl]benzamide | 516.3 |
| 90 | 4-[((Z)-[(3S)-3-methylpiperazin-1-yl]{[(1S,2S,3R,5R)-2,6,6-trimethylbicyclo[3.1.1]hept-3-yl]imino}methyl)amino]-N-[(2R)-2-phenylpropyl]benzamide | 516.3 |
| 91 | N-[2-(2,4-dichlorophenyl)ethyl]-4-[((E)-(3,5-dimethylpiperazin-1-yl){[(1S,2S,3S,5R)-2,6,6-trimethylbicyclo[3.1.1]hept-3-yl]imino}methyl)amino]benzamide | 584.7 |
| 92 | N-[2-(2,4-difluorophenyl)ethyl]-4-[((E)-[(3S)-3-methylpiperazin-1-yl]{[(1S,2S,3S,5R)-2,6,6-trimethylbicyclo[3.1.1]hept-3-yl]imino}methyl)amino]benzamide | 538.2 |
| 93 | N-[2-(2,4-dichlorophenyl)ethyl]-4-{[(E)-{[(1S,2S,3S,5R)-2,6,6-trimethylbicyclo[3.1.1]hept-3-yl]imino}(3,4,5-trimethylpiperazin-1-yl)methyl]amino}benzamide | 598.7 |
| 94 | N-{2-[2-fluoro-4-(methyloxy)phenyl]ethyl}-4-[((Z)-[(3S)-3-methylpiperazin-1-yl]{[(1S,2S,3S,5R)-2,6,6-trimethylbicyclo[3.1.1]hept-3-yl]imino}methyl)amino]benzamide | 550.2 |
| 95 | N-[(1S)-2-(2,4-dichlorophenyl)-1-(hydroxymethyl)ethyl]-4-[((E)-[(3S)-3-methylpiperazin-1-yl]{[(1S,2S,3S,5R)-2,6,6-trimethylbicyclo[3.1.1]hept-3-yl]imino}methyl)amino]benzamide | 600.4 |
| 96 | N-[(1R)-2-(2,4-dichlorophenyl)-1-(hydroxymethyl)ethyl]-4-[((E)-[(3S)-3-methylpiperazin-1-yl]{[(1S,2S,3S,5R)-2,6,6-trimethylbicyclo[3.1.1]hept-3-yl]imino}methyl)amino]benzamide | 600.5 |
| 97 | N-(6-chloro-1,2,3,4-tetrahydronaphthalen-2-yl)-4-[((Z)-[(3S)-3-methylpiperazin-1-yl]{[(1S,2S,3S,5R)-2,6,6-trimethylbicyclo[3.1.1]hept-3-yl]imino}methyl)amino]benzamide | 562.3 |
| 98 | N-[2-(2-fluoro-4-methylphenyl)ethyl]-4-({(E)-[(4-methylcyclohexyl)imino][(3S)-3-methylpiperazin-1-yl]methyl}amino)benzamide | 494.6 |
| 99 | N-[2-(2,4-dichlorophenyl)ethyl]-N-methyl-4-[((E)-[(3S)-3-methylpiperazin-1-yl]{[(1S,2S,3S,5R)-2,6,6-trimethylbicyclo[3.1.1]hept-3-yl]imino}methyl)amino]benzamide | 584.7 |
| 100 | N-[2-(2,4-dichlorophenyl)ethyl]-2-fluoro-4-[((E)-[(3S)-3-methylpiperazin-1-yl]{[(1S,2S,3S,5R)-2,6,6-trimethylbicyclo[3.1.1]hept-3-yl]imino}methyl)amino]benzamide | 588.6 |
| 701 | N-(6-fluoro-1,2,3,4-tetrahydronaphthalen-2-yl)-4-[((E)-[(3S)-3-methylpiperazin-1-yl]{[(1S,2S,3S,5R)-2,6,6-trimethylbicyclo[3.1.1]hept-3-yl]imino}methyl)amino]benzamide | 546 |
| 102 | N-[6-(methyloxy)-1,2,3,4-tetrahydronaphthalen-2-yl]-4-[((Z)-[(3S)-3-methylpiperazin-1-yl]{[(1S,2S,3S,5R)-2,6,6-trimethylbicyclo[3.1.1]hept-3-yl]imino}methyl)amino]benzamide | 558 |
| 103 | N-{2-[2-fluoro-4-(methyloxy)phenyl]ethyl}-4-({(Z)-{[(1S,2S)-2-methylcycloheptyl]imino}[(3S)-3-methylpiperazin-1-yl]methyl}amino)benzamide | 524.2 |
| 104 | N-[2-(4-bromo-2-fluorophenyl)ethyl]-4-[((E)-[(3S)-3-methylpiperazin-1-yl]{[(1S,2S,3S,5R)-2,6,6- | 598 |

Table of Examples 61–113

| Example | Name | MH+ |
|---|---|---|
| 105 | trimethylbicyclo[3.1.1]hept-3-yl]imino}methyl)amino]benzamide N-{2-[4-fluoro-2-(trifluoromethyl)phenyl]ethyl}-4-[((E)-[(3S)-3-methylpiperazin-1-yl]{[(1S,2S,3S,5R)-2,6,6-trimethylbicyclo[3.1.1]hept-3-yl]imino}methyl)amino]benzamide | 588 |
| 106 | N-[2-(4-bromo-2-fluorophenyl)-2-hydroxyethyl]-4-[((E)-[(3S)-3-methylpiperazin-1-yl]{[(1S,2S,3S,5R)-2,6,6-trimethylbicyclo[3.1.1]hept-3-yl]imino}methyl)amino]benzamide | 614 |
| 107 | N-[2-(2-fluoro-4-methylphenyl)ethyl]-4-({(Z)-{[(1S,2S)-2-methylcycloheptyl]imino}[(3S)-3-methylpiperazin-1-yl]methyl}amino)benzamide | 508.3 |
| 108 | N-[2-(4-bromo-2-fluorophenyl)ethyl]-4-[((Z)-[(3S)-3-methylpiperazin-1-yl]{[4-(trifluoromethyl)cyclohexyl]imino}methyl)amino]benzamide | 612.2 |
| 109 | N-[5-(methyloxy)-2,3-dihydro-1H-inden-2-yl]-4-[((Z)-[(3S)-3-methylpiperazin-1-yl]{[(1S,2S,3S,5R)-2,6,6-trimethylbicyclo[3.1.1]hept-3-yl]imino}methyl)amino]benzamide | 544.3 |
| 110 | 4-[((Z)-[(3R,5S)-3,5-dimethylpiperazin-1-yl]{[(1S,2S,3S,5R)-2,6,6-trimethylbicyclo[3.1.1]hept-3-yl]imino}methyl)amino]-N-{2-[2-fluoro-4-(methyloxy)phenyl]ethyl}benzamide | 564.3 |
| 111 | N-[2-(4-bromo-2-fluorophenyl)ethyl]-4-[((Z)-[(3R,5S)-3,5-dimethylpiperazin-1-yl]{[(1S,2S,3S,5R)-2,6,6-trimethylbicyclo[3.1.1]hept-3-yl]imino}methyl)amino]benzamide | 612 |
| 112 | N-[2-(4-bromo-2-fluorophenyl)ethyl]-4-({(Z)-[(4-methylcyclohexyl)imino][(3S)-3-methylpiperazin-1-yl]methyl}amino)benzamide | 558 |
| 113 | N-[2-(4-bromo-2-fluorophenyl)ethyl]-4-({(Z)-(cycloheptylimino)[(3S)-3-methylpiperazin-1-yl]methyl}amino)benzamide | 558 |

Examples 114–118

Examples 114–118 listed in the following Table were prepared using the general procedures described above.

Table of Examples 114–118

| Example | Name | MH+ |
|---|---|---|
| 114 | 4-[((1E)-[(3S)-3-methylpiperazin-1-yl]{[(1S,2S,3S,5R)-2,6,6-trimethylbicyclo[3.1.1]hept-3-yl]amino}methylidene)amino]-N-[(2R)-1,2,3,4-tetrahydronaphthalen-2-yl]benzamide | 528.3 |
| 115 | N-[(2R)-5-(methyloxy)-1,2,3,4-tetrahydronaphthalen-2-yl]-4-[((1E)-[(3S)-3-methylpiperazin-1-yl]{[(1S,2S,3S,5R)-2,6,6-trimethylbicyclo[3.1.1]hept-3-yl]amino}methylidene)amino]benzamide | 558.7 |
| 116 | N-[(2S)-7-(methyloxy)-1,2,3,4-tetrahydronaphthalen-2-yl]-4-[((1E)-[(3S)-3-methylpiperazin-1-yl]{[(1S,2S,3S,5R)-2,6,6-trimethylbicyclo[3.1.1]hept-3-yl]amino}methylidene)amino]-benzamide | 558.8 |
| 117 | 4-({(1E)-(cycloheptylamino)[(3S)-3-methylpiperazin-1-yl]methylidene}amino)-N-[(2R)-1,2,3,4-tetrahydronaphthalen-2-yl]benzamide | 488.6 |
| 118 | N-[(2S)-5-(methyloxy)-1,2,3,4-tetrahydronaphthalen-2-yl]-4-[((1E)-[(3S)-3-methylpiperazin-1-yl]{[(1S,2S,3S,5R)-2,6,6-trimethylbicyclo[3.1.1]hept-3-yl]amino}methylidene)amino]-benzamide | 558.7 |

Example 119

$EC_{50}$ values of test compounds were determined by treating cells expressing MC4-R with test compound and lysing the cells and measuring intercellular cAMP concentration with Amersham-Pharmacia RPA-559 cAMP Scintillation Proximity Assay (SPA) kit. The following compounds were synthesized and tested according to this assay. The compounds listed below displayed –log $EC_{50}$ values above about 3. The title compounds of Examples 61–118 also all displayed –log $EC_{50}$ values above about 3. For this reason each of the compound in the following list and each of the title compounds of Examples 61–118 are individually preferred and are preferred as a group. Furthermore, the groups corresponding to $R^1$ through $R^{10}$ for each of these compounds are also preferred. Nomenclature for these compounds was provided using Nomenclator (v.3.0 & v.5.0) from CmemInnovation Software, Inc. The following compounds are merely illustrative and should not be construed as limiting of the instant invention:

{4-[((1Z)-2-aza-2-cyclopentyl-1-piperazinylvinyl)amino]phenyl}-N-[2-(2,4-dichlorophenyl)ethyl]carboxamide, (4-{[1-((5S)-2,5-dimethylpiperazinyl)(1Z)-2--aza-3-methylbut-1-enyl]amino}phenyl)-N-[2,-(2,4-dichlorophenyl)ethyl]carboxamide, (4-{[(1Z)-2-aza-2-cyclohexyl-1-(3-oxopiperazinyl)vinyl]amino}phenyl)-N-[2-(2,4-dichlorophenyl)ethyl]carboxamide, {4-[((1Z)-2-aza-2-cyclohexyl-1-morpholin-4-ylvinyl)amino]phenyl}-N-[2-(2,4-dichlorophenyl)ethyl]carboxamide, {4-[((1Z)-2-aza-2-cyclohexyl-1-piperazinylvinyl)amino]phenyl}-N-[2-(2,4-dichlorophenyl)ethyl]carboxamide, (4-{[1-((3S)-3-methylpiperazinyl)(1Z)-2-aza-2-cyclopentylvinyl]amino}phenyl)-N-[2-(2,4-dichlorophenyl)ethyl]carboxamide, {4-[((1Z)-2-aza-2-cyclopentyl-1-(1,4-diazaperhydroepinyl)vinyl]amino]phenyl}-N-[2-(2,4-dichlorophenyl)ethyl]carboxamide, [4-({(1Z)-1-[(2-amino-2-methylpropyl)amino]-2-aza-2-cyclohexylvinyl}amino)phenyl]-N-[2-(2,4-dichlorophenyl)ethyl]carboxamide, (4-{[1-(2,5-diazabicyclo[2.2.1]hept-2-yl)(1Z)-2-aza-2-cyclohexylvinyl]amino}phenyl)-N-[2-(2,4-dichlorophenyl)ethyl]carboxamide, (4-{[1-((3S)-3-methylpiperazinyl)(1Z)-2-aza-2-cyclohex-3-enylvinyl]amino}phenyl)-N-[2-(2,4-dichlorophenyl)ethyl]carboxamide, (4-{[1-((3S)-3-methylpiperazinyl)(1Z)-2-aza-2-(4-oxocyclohexyl)vinyl]amino}phenyl)-N-[2-(2,4-dichlorophenyl)ethyl]carboxamide, (4-{[(1 E)-2-aza-2-cyclohexyl-1-(3- hydroxypiperidyl)vinyl]amino}phenyl)-N-[2-(2,4-dichlorophenyl)ethyl]carboxamide, (4-{[1-((3S)-3-methylpiperazinyl)(1Z)-2-aza-2-cyclohexylvinyl]amino}-2-chlorophenyl)-N-[2-(2,4-dichlorophenyl)ethyl]carboxamide, {4-[((1Z)-2-aza-2-cyclohexyl-1-(1,4-diazaperhydroepinyl)vinyl)amino]phenyl}-N-[2-(2,4-dichlorophenyl)ethyl]carboxamide, (4-{[1-((3R)-3-methylpiperazinyl)(1Z)-2-aza-2-cyclohexylvinyl]amino}phenyl)-N-[2-(2,4-dichlorophenyl)ethyl]carboxamide, (4-{[1-((3S)-3-methylpiperazinyl)(1Z)-2-aza-2-cyclohexylvinyl]amino}phenyl)-N-[2-(2,4-dichlorophenyl)ethyl]carboxamide, (4-{[((1Z)-2-aza-2-cyclohexyl-1-piperazinylvinyl)amino]methyl}phenyl)-N-[2-(2,4-dichlorophenyl)ethyl]carboxamide, (4-{[(1Z)-2-aza-1-(3,5-dimethylpiperazinyl)-2-cyclopentylvinyl]amino}phenyl)-N-[2-(2,4-dichlorophenyl)ethyl]carboxamide, (4-{[(1Z)-2-aza-1-(2,5-dimethylpiperazinyl)-2-cyclopentylvinyl]amino}phenyl)-N-[2-(2,4-dichlorophenyl)ethyl]carboxamide, {4-[((1Z)-2-aza-2-cycloheptyl-1-piperazinylvinyl)amino]phenyl}-N-[2-(2,4-dichlorophenyl)ethyl]carboxamide, (4-{[1-((3S)-3-methylpiperazinyl)(1Z)-2-aza-2-cyclohexylvinyl]amino}phenyl)-N-[2-(2,4-difluorophenyl)ethyl]carboxamide, (4-{[1-((3S)-3-methylpiperazinyl)(1Z)-2-aza-2-cyclohexylvinyl]amino}phenyl)-N-[2-(4-chlorophenyl)ethyl]carboxamide, (4-{[1-((3S)-3-methylpiperazinyl)(1Z)-2-aza-2-cyclohexylvinyl]amino}phenyl)-N-[2-(4-fluorophenyl)ethyl]carboxamide, (4-{[1-((3S)-3-methylpiperazinyl)(1Z)-2-aza-2-cyclohexylvinyl]amino}phenyl)-N-(2-phenylethyl)carboxamide, (4-{[(1E)-2-aza-2-(2,4-dichlorophenyl)-1-(3,5-dimethylpiperazinyl)vinyl]amino}phenyl)-N-[2-(2,4-dichlorophenyl)ethyl]carboxamide, (4-{[(1Z)-2-aza-2-cyclohexyl-1-(3-imino-1-oxo(2,5,6,7,8,8a-hexahydro-2,7-diazaindolizin-7-yl))vinyl]amino}phenyl)-N-[2-(2,4-dichlorophenyl)ethyl]carboxamide, [4-({1-((3S)-3-methylpiperazinyl)(1Z)-2-aza-2-[4-(trifluoromethyl)cyclohexyl]vinyl}amino)phenyl]-N-[2-(2,4-dichlorophenyl)ethyl]carboxamide, (4-{[(1Z)-2-aza-1-(3,5-dimethylpiperazinyl)-2-cyclohex-3-enylvinyl]amino}phenyl)-N-[2-(2,4-dichlorophenyl)ethyl]carboxamide, (4-{[1-((3S)-3-methylpiperazinyl)(1Z)-2-aza-2-bicyclo[2.2.1]hept-2-ylvinyl]amino}phenyl)-N-[2-(2,4-dichlorophenyl)ethyl]carboxamide, (4-{[(1 E)-2-aza-2-cyclohexyl-1-(4-methylpiperidyl)vinyl]amino}phenyl)-N-[2-(2,4-dichlorophenyl)ethyl]carboxamide, (4-{[1-((3S)-3-methylpiperazinyl)(1Z)-2-aza-2-cyclohexylvinyl]amino}-5-chloro-2-methoxyphenyl)-N-[2-(2,4-dichlorophenyl)ethyl]carboxamide, (4-{[(1Z)-2-aza-1-(3,5-dimethylpiperazinyl)-2-cyclohexylvinyl]amino}phenyl)-N-[2-(2,4-dichlorophenyl)ethyl]carboxamide, [4-({(1E)-1-[(3-aminocyclohexyl)amino]-2-aza-2-cyclohexylvinyl}amino)phenyl]-N-[2-(2,4-dichlorophenyl)ethyl]carboxamide, (4-{[1-((5S)-2,5-dimethylpiperazinyl)(1Z)-2-aza-2-cyclohexylvinyl]amino}phenyl)-N-[2-(2,4-dichlorophenyl)ethyl]carboxamide, (4-{[1-((3S)-3-methylpiperazinyl)(1Z)-2-aza-2-cyclohexylvinyl]amino}-3-methylphenyl)-N-[2-(2,4-dichlorophenyl)ethyl]carboxamide, [4-({[1-((3S)-3-methylpiperazinyl)(1Z)-2-aza-2-cyclohexylvinyl]amino}methyl)phenyl]-N-[2-(2,4-dichlorophenyl)ethyl]carboxamide, (4-{[((1Z)-2-aza-2-cyclohexyl-1-(1,4-diazaperhydroepinyl)vinyl)amino]methyl}phenyl)-N-[2-(2,4-dichlorophenyl)ethyl]carboxamide, [4-({(1E)-1-[((1S,2R)-2-aminocyclohexyl)amino]-2-aza-2-cyclohexylvinyl}amino)phenyl]-N-[2-(2,4-dichlorophenyl)ethyl]carboxamide, (4-{[1-((3S)-3-methylpiperazinyl)(1Z)-2-aza-2-cycloheptylvinyl]amino}phenyl)-N-[2-(2,4-dichlorophenyl)ethyl]carboxamide, (4-{[1-((3S)-3-ethylpiperazinyl)(1Z)-2-aza-2-cyclohexylvinyl]amino}phenyl)-N-[2-(2,4-dichlorophenyl)ethyl]carboxamide, (4-{[1-((3S)-3-methylpiperazinyl)(1Z)-2-aza-2-(2-methylcyclohexyl)vinyl]amino}phenyl)-N-[2-(2,4-dichlorophenyl)ethyl]carboxamide, (4-{[1-((3S)-3,4-dimethylpiperazinyl)(1Z)-2-aza-2-cyclohexylvinyl]amino}phenyl)-N-[2-(2,4-dichlorophenyl)ethyl]carboxamide, (4-{[((1Z)-2-aza-1-(3,3-dimethylpiperazinyl)-2-cyclohexylvinyl]amino}phenyl)-N-[2-(2,4-dichlorophenyl)ethyl]carboxamide, (4-{[1-((3R,5R)-3,5-dimethylpiperazinyl)(1Z)-2-aza-2-cyclohexylvinyl]amino}phenyl)-N-[2-(2,4-dichlorophenyl)ethyl]carboxamide, (4-{[1-((3S)-3-methylpiperazinyl)(1Z)-2-aza-3-cyclohexylprop-1-enyl]amino}phenyl)-N-[2-(2,4-dichlorophenyl)ethyl]carboxamide, (4-{[(1E)-1-((3S)-3-methylpiperazinyl)-2-aza-2-(3-methylcyclohexyl)vinyl]amino}phenyl)-N-[2-(2,4-dichlorophenyl)ethyl]carboxamide, (4-{[(1E)-1-((3S)-3-methylpiperazinyl)-2-aza-2-(4-methylcyclohexyl)vinyl]amino}phenyl)-N-[2-(2,4-dichlorophenyl)ethyl]carboxamide, (4-{[(1Z)-2-aza-1-(2,6-dimethylpiperazinyl)-2-cyclohexylvinyl]amino}phenyl)-N-[2-(2,4-dichlorophenyl)ethyl]carboxamide, (4-{[(1E)-2-((1R,2R)-2-methylcyclohexyl)-1-((3S)-3-methylpiperazinyl)-2-azavinyl]amino}phenyl)-N-[2-(2,4-dichlorophenyl)ethyl]carboxamide, (4-{[1-((3S)-3-methylpiperazinyl)(1Z)-2-aza-2-(4-methylcyclohexyl)vinyl]amino}phenyl)-N-[2-(2,4-dichlorophenyl)ethyl]carboxamide, (4-{[1-((3S)-3-methylpiperazinyl)(1Z)-2-aza-2-cyclohexylvinyl]amino}-3-methoxyphenyl)-N-[2-(2,4-dichlorophenyl)ethyl]carboxamide, (4-{[(1E)-1-((3S)-3-methylpiperazinyl)-2-aza-2-(2-methoxycyclohexyl)vinyl]amino}phenyl)-N-[2-(2,4-dichlorophenyl)ethyl]carboxamide, (4-{[(1E)-1-((3S)-3-methylpiperazinyl)-2-aza-2-(4-methoxycyclohexyl)vinyl]amino}phenyl)-N-[2-(2,4-dichlorophenyl)ethyl]carboxamide, (4-{[(1Z)-2-aza-1-(3,5-dimethylpiperazinyl)-2-cyclohexylvinyl]amino}phenyl)-N-[2-(4-chlorophenyl)ethyl]carboxamide, [4-({(1E)-2-aza-1-(3,5-dimethylpiperazinyl)-2-[4-(trifluoromethyl)cyclohexyl]vinyl}amino)phenyl]-N-[2-(2,4-dichlorophenyl)ethyl]carboxamide, (4-{[(1Z)-2-aza-1-(3,6-diazabicyclo[4.3.0]non-3-yl)-2-cyclohexylvinyl]amino}phenyl)-N-[2-(2,4-dichlorophenyl)ethyl]carboxamide, (4-{[1-(3,5-dimethylpiperazinyl)(1Z)-2-aza-2-bicyclo[2.2.1]hept-2-ylvinyl]amino}phenyl)-N-[2-(2,4-dichlorophenyl)ethyl]carboxamide, (4-{[(1Z)-2-aza-1-(3,5-dimethyl piperidyl)-2-cyclohexylvinyl]amino}phenyl)-N-[2-(2,4-dichlorophenyl)ethyl]carboxamide, (4-{[(1Z)-2-aza-1-(3,5-dimethylpiperazinyl)-2-cyclohexylvinyl]amino}-5-chloro-2-methoxyphenyl)-N-[2-(2,4-dichlorophenyl)ethyl]carboxamide, (4-{[1-((3S)-3-methylpiperazinyl)(1Z)-2-aza-2-cyclohexylvinyl]amino}phenyl)-N-(2-indol-2-ylethyl)carboxamide, [4-({[(1Z)-2-aza-1-(3,5-dimethylpiperazinyl)-2-cyclohexylvinyl]amino}methyl)phenyl]-N-[2-(2,4-dichlorophenyl)ethyl]carboxamide, [4-({[(1Z)-2-aza-1-(2,5-dimethylpiperazinyl)-2-cyclohexylvinyl]amino}methyl)phenyl]-N-[2-(2,4-dichlorophenyl)ethyl]carboxamide, (4-{[1-((3S,5R)-3,5-dimethylpiperazinyl)(1Z)-2-aza-2-cycloheptylvinyl]amino}phenyl)-N-[2-(2,4-dichlorophenyl)ethyl]carboxamide, [4-({1-[(3S)-3-(methylethyl)piperazinyl](1Z)-2-aza-2-cyclohexylvinyl}amino)phenyl]-N-[2-(2,4-dichlorophenyl)ethyl]carboxamide, (4-{[(1Z)-2-aza-1-(3,5-dimethylpiperazinyl)-2-(2-methylcyclohexyl)vinyl]amino}phenyl)-N-[2-(2,4-dichlorophenyl)ethyl]carboxamide, (4-{[(1Z)-2-aza-1-(3,5-dimethylpiperazinyl)-3-cyclohexylprop-1-enyl]amino}phenyl)-N-[2-(2,4-dichlorophenyl)ethyl]carboxamide, (4-{[(1E)-1-((3S)-3-methylpiperazinyl)-2-aza-2-cyclooctylvinyl]

amino}phenyl)-N-[2-(2,4-dichlorophenyl)ethyl]carboxamide, (4-{[1-((3S,5R)-3,5-dimethylpiperazinyl)(1Z)-2-aza-2-(3-methylcyclohexyl)vinyl]amino}phenyl)-N-[2-(2,4-dichlorophenyl)ethyl]carboxamide, (4-{[1-((3S,5R)-3,5-dimethylpiperazinyl)(1Z)-2-aza-2-(4-methylcyclohexyl)vinyl]amino}phenyl)-N-[2-(2,4-dichlorophenyl)ethyl]carboxamide, (4-{[(1E)-2-((2S, 1R)-2-methylcyclohexyl)-2-aza-1-(3,5-dimethylpiperazinyl)vinyl]amino}phenyl)-N-[2-(2,4-dichlorophenyl)ethyl]carboxamide, (4-{[(1E)-2-((1R,2R)-2-methylcyclohexyl)-2-aza-1-(3,5-dimethylpiperazinyl)vinyl]amino}phenyl)-N-[2-(2,4-dichlorophenyl)ethyl]carboxamide, (4-{[(1E)-2-((1R,2R)-2-methylcycloheptyl)-1-((3S)-3-methylpiperazinyl)-2-azavinyl]amino}phenyl)-N-[2-(2,4-dichlorophenyl)ethyl]carboxamide, (4-{[(1E)-1-((3S)-3-methylpiperazinyl)-2-aza-2-(2,2-dimethylcyclohexyl)vinyl]amino}phenyl)-N-[2-(2,4-dichlorophenyl)ethyl]carboxamide, (4-{[1-((3S,5S)-3,5-dimethylpiperazinyl)(1Z)-2-aza-2-(4-methylcyclohexyl)vinyl]amino}phenyl)-N-[2-(2,4-dichlorophenyl)ethyl]carboxamide, [4-({1-[(3S)-3-(2-methylthioethyl)piperazinyl](1Z)-2-aza-2-cyclohexylvinyl}amino)phenyl]-N-[2-(2,4-dichlorophenyl)ethyl]carboxamide, (4-{[(1Z)-2-aza-1-(3,5-dimethylpiperazinyl)-2-cyclohexylvinyl]amino}-3-methoxyphenyl)-N-[2-(2,4-dichlorophenyl)ethyl]carboxamide, (4-{[(1 E)-2-aza-1-(3,5-dimethylpiperazinyl)-2-(2-methoxycyclohexyl)vinyl]amino}phenyl)-N-[2-(2,4-dichlorophenyl)ethyl]carboxamide, (4-{[(1E)-2-aza-1-(3,5-dimethylpiperazinyl)-2-(4-methoxycyclohexyl)vinyl]amino}phenyl)-N-[2-(2,4-dichlorophenyl)ethyl]carboxamide, (4-{[(1Z)-2-aza-1-(3,5-dimethylpiperazinyl)-2-cyclohexylvinyl]amino}phenyl)-N-[2-(4-methoxyphenyl)ethyl]carboxamide, {4-[((1E)-2-aza-1-{[2-(diethylamino)ethyl]amino}-2-cyclohexylvinyl)amino]phenyl}-N-[2-(4-methoxyphenyl)ethyl]carboxamide, (4-{[(1E)-1-((3S)-3-methylpiperazinyl)-2-aza-2-indan-2-ylvinyl]amino}phenyl)-N-[2-(4-fluorophenyl)ethyl]carboxamide, [4-({(1E)-1-((3S)-3-methylpiperazinyl)-2-aza-2-[2-(methylethyl)phenyl]vinyl}amino)phenyl]-N-[2-(4-chlorophenyl)ethyl]carboxamide, {4-[((1Z)-2-aza-1-{[2-(dimethylamino)ethyl]benzylamino}-3-methylbut-1-enyl)amino]phenyl}-N-[2-(2,4-dichlorophenyl)ethyl]carboxamide, [4-({(1 E)-2-aza-1-[({5-[(dimethylamino)methyl](2-furyl)}methyl)amino]-2-cyclohexylvinyl}amino)phenyl]-N-[2-(2,4-dichlorophenyl)ethyl]carboxamide, (4-{[(1Z)-2-aza-1-(2,5-diazabicyclo[4.4.0]dec-2-yl)-2-cyclohexylvinyl]amino}phenyl)-N-[2-(2,4-dichlorophenyl)ethyl]carboxamide, (4-{[(1Z)-2-aza-1-(3,5-dimethylpiperazinyl)-2-cyclohexylvinyl]amino}phenyl)-N-(2-indol-3-ylethyl)carboxamide, [4-({(1E)-2-aza-2-[4-(tert-butyl)cyclohexyl]-1-piperazinylvinyl}amino)phenyl]-N-[2-(2,4-dichlorophenyl)ethyl]carboxamide, [4-({1-[(3S)-3-(2-methylpropyl)piperazinyl](1Z)-2-aza-2-cyclohexylvinyl}amino)phenyl]-N-[2-(2,4-dichlorophenyl)ethyl]carboxamide, (4-{[(1 E)-1-((3S)-3-methylpiperazinyl)-2-aza-2-(3,3,5-trimethylcyclohexyl)vinyl]amino}phenyl)-N-[2-(2,4-dichlorophenyl)ethyl]carboxamide, (4-{[1-((3S,5R)-3,5-dimethylpiperazinyl)(1Z)-2-aza-2-cyclooctylvinyl]amino}phenyl)-N-[2-(2,4-dichlorophenyl)ethyl]carboxamide, (4-{[(1E)-2-aza-2-(2,6-dimethylcyclohexyl)-1-(3,5-dimethylpiperazinyl)vinyl]amino}phenyl)-N-[2-(2,4-dichlorophenyl)ethyl]carboxamide, (4-{[(1E)-2-aza-2-(2,3-dimethylcyclohexyl)-1-(3,5-dimethylpiperazinyl)vinyl]amino}phenyl)-N-[2-(2,4-dichlorophenyl)ethyl]carboxamide, (4-{[(1E)-2-((1R,2R)-2-methylcycloheptyl)-2-aza-1-(3,5-dimethylpiperazinyl)vinyl]amino}phenyl)-N-[2-(2,4-dichlorophenyl)ethyl]carboxamide, (4-{[(1 E)-2-((1R,2R)-2-ethylcyclohexyl)-1-((3S,5R)-3,5-dimethyl piperazinyl)-2-azavinyl]amino}phenyl)-N-[2-(2,4-dichlorophenyl)ethyl]carboxamide, (4-{[(1E)-2-aza-2-(2,2-dimethylcyclohexyl)-1-(3,5-dimethylpiperazinyl)vinyl]amino}phenyl)-N-[2-(2,4-dichlorophenyl)ethyl]carboxamide, (4-{[(1E)-1-((3S)-3-methylpiperazinyl)-2-aza-2-(2-propylcyclohexyl)vinyl]amino}phenyl)-N-[2-(2,4-dichlorophenyl)ethyl]carboxamide, (4-{[(1 E)-1-((3S)-3-methylpiperazinyl)-2-aza-2-(1,2,3,4-tetrahydronaphthyl)vinyl]amino}phenyl)-N-[2-(2,4-dichlorophenyl)ethyl]carboxamide, [4-({(1Z)-2-aza-2-cyclohexyl-1-[4-(2-furylcarbonyl)piperazinyl]vinyl}amino)phenyl]-N-[2-(2,4-dichlorophenyl)ethyl]carboxamide, {4-[((1Z)-2-aza-1-{[2-(dimethylamino)ethyl]benzylamino}hex-1-enyl)amino]phenyl}-N-[2-(2,4-dichlorophenyl)ethyl]carboxamide, {4-[((1Z)-2-aza-1-{[2-(dimethylamino)ethyl][(4-methylphenyl)methyl]amino}-3-methylbut-1-enyl)amino]phenyl}-N-[2-(2,4-dichlorophenyl)ethyl]carboxamide, (4-{[(1E)-1-((3S)-3-methylpiperazinyl)-2-adamantan-2-yl-2-azavinyl]amino}phenyl)-N-[2-(2,4-dichlorophenyl)ethyl]carboxamide, [4-({(1E)-1-((3S)-3-methylpiperazinyl)-2-aza-2-[2-(methylethyl)phenyl]vinyl}amino)phenyl]-N-[2-(4-methoxyphenyl)ethyl]carboxamide, (4-{[(1 E)-2-((1R,5R)-2,6,6-trimethylbicyclo[3.1.1]hept-3-yl)-1-((3S)-3-methylpiperazinyl)-2-azavinyl]amino}phenyl)-N-[2-(2,4-dichlorophenyl)ethyl]carboxamide, (4-{[(1E)-1-((3S)-3-methylpiperazinyl)-2-((2S,3S, 1R,5R)-2,6,6-trimethylbicyclo[3.1.1]hept-3-yl)-2-azavinyl]amino}phenyl)-N-[2-(2,4-dichlorophenyl)ethyl]carboxamide, (4-{[(1 E)-1-((3S)-3-methylpiperazinyl)-2-((1S,5S,2R,3R)-2,6,6-trimethylbicyclo[3.1.1]hept-3-yl)-2-azavinyl]amino}phenyl)-N-[2-(2,4-dichlorophenyl)ethyl]carboxamide, {4-[((1Z)-2-aza-1-{[2-(dimethylamino)ethyl]benzylamino}-2-cyclohexylvinyl)amino]phenyl}-N-(2-(2-thienyl)ethyl)carboxamide, [4-({(1E)-1-((3S)-3-methylpiperazinyl)-2-aza-2-[4-(tert-butyl)cyclohexyl]vinyl}amino)phenyl]-N-[2-(2,4-dichlorophenyl)ethyl]carboxamide, (4-{[(1E)-1-((3S,5R)-3,5-dimethylpiperazinyl)-2-aza-2-(3,3,5-trimethylcyclohexyl)vinyl]amino}phenyl)-N-[2-(2,4-dichlorophenyl)ethyl]carboxamide, (4-{[(1 E)-1-((3S,5R)-3,5-dimethylpiperazinyl)-2-aza-2-(2-propylcyclohexyl)vinyl]amino}phenyl)-N-[2-(2,4-dichlorophenyl)ethyl]carboxamide, (4-{[(1Z)-2-aza-2-cyclohexyl-1-(3-phenylpiperazinyl)vinyl]amino}phenyl)-N-[2-(2,4-dichlorophenyl)ethyl]carboxamide, (4-{[(1E)-2-aza-1-(3,5-dimethylpiperazinyl)-2-(1,2,3,4-tetrahydronaphthyl)vinyl]amino}phenyl)-N-[2-(2,4-dichlorophenyl)ethyl]carboxamide, (4-{[(1Z)-2-aza-1-(3,5-dimethylpiperazinyl)-2-indan-2-ylvinyl]amino}phenyl)-N-[2-(4-methoxyphenyl)ethyl]carboxamide, {4-[((1Z)-2-aza-1-{[2-(dimethylamino)ethyl][(4-ethylphenyl)methyl]amino}-3-methylbut-1-enyl)amino]phenyl}-N-[2-(2,4-dichlorophenyl)ethyl]carboxamide, (4-{[(1E)-2-adamantan-2-yl-2-aza-1-(3,5-dimethylpiperazinyl)vinyl]amino}phenyl)-N-[2-(2,4-dichlorophenyl)ethyl]carboxamide, {6-[((1Z)-2-aza-1-{[2-(dimethylamino)ethyl]benzylamino}-2-cyclohexylvinyl)amino](3-pyridyl)}-N-(2-phenylethyl)carboxamide, (4-{[(1E)-2-aza-1-(3,5-dimethylpiperazinyl)-2-(2,6,6-trimethylbicyclo[3.1.1]hept-3-yl)vinyl]amino}phenyl)-N-[2-(2,4-dichlorophenyl)ethyl]carboxamide, [4-({(1E)-1-(3,5-dimethylpiperazinyl)-2-aza-2-[4-(tert-butyl)cyclohexyl]vinyl}amino)phenyl]-N-[2-(2,4-dichlorophenyl)ethyl]carboxamide, [4-({(1Z)-2-aza-2-cyclohexyl-1-[(imidazol-2-ylmethyl)benzylamino]vinyl}amino)phenyl]-N-(2-phenylethyl)carboxamide, (4-{[(1 E)-1-((3S)-3-methylpiperazinyl)-2-aza-2-(4-phenylcyclohexyl)vinyl]

aminophenyl)-N-[2-(2,4-dichlorophenyl)ethyl] carboxamide, {4-[((1Z)-2-aza-1-{[2-(dimethylamino)ethyl]benzylamino}-2-cyclohexylvinyl)amino]phenyl}-N-[2-(2,4-dichlorophenyl)ethyl]carboxamide, {4-[((1Z)-2-aza-1-{[2-(dimethylamino)ethyl]benzylamino}-2-cyclohexylvinyl)amino]phenyl}-N-[2-(4-bromophenyl)ethyl]carboxamide, {4-[((1Z)-2-aza-1-{[2-(dimethylamino)ethyl]benzylamino}-2-cyclohexylvinyl)amino]phenyl}-N-[2-(3-chlorophenyl)ethyl]carboxamide, {4-[((1Z)-2-aza-1-{[2-(dimethylamino)ethyl]benzylamino}-2-cyclohexylvinyl)amino]phenyl}-N-[2-(2-chlorophenyl)ethyl]carboxamide, {4-[((1Z)-2-aza-1-{[2-(dimethylamino)ethyl]benzylamino}-2-cyclohexylvinyl)amino]phenyl}-N-[2-(4-chlorophenyl)ethyl]carboxamide, {4-[((1Z)-2-aza-1-{[2-(dimethylamino)ethyl]benzylamino}-2-cyclohexylvinyl)amino]phenyl}-N-[2-(2-fluorophenyl)ethyl]carboxamide, {4-[((1Z)-2-aza-1-{[2-(dimethylamino)ethyl]benzylamino}-2-cyclohexylvinyl)amino]phenyl}-N-[2-(2-fluorophenyl)ethyl]carboxamide, {4-[((1Z)-2-aza-1-{[2-(dimethylamino)ethyl]benzylamino}-2-cyclohexylvinyl)amino]phenyl}-N-(2-phenylethyl)carboxamide, {4-[((1Z)-2-aza-1-{[2-(dimethylamino)ethyl]benzylamino}-2-cyclohexylvinyl)amino]phenyl}-N-[2-(4-hydroxyphenyl)ethyl]carboxamide, {4-[((1Z)-2-aza-1-{[2-(dimethylamino)ethyl]benzylamino}-2-cyclohexylvinyl)amino]phenyl}-N-(2-cyclohex-1-enylethyl)carboxamide, (4-{[(1E)-2-aza-1-(3,5-dimethylpiperazinyl)-2-(4-phenylcyclohexyl)vinyl]amino}phenyl)-N-[2-(2,4-dichlorophenyl)ethyl]carboxamide, {4-[((1Z)-2-aza-1-{[2-(dimethylamino)ethyl][(4-methylphenyl)methyl]amino}-2-cyclohexylvinyl)amino]phenyl}-N-[2-(2,4-dichlorophenyl)ethyl]carboxamide, {4-[((1Z)-2-aza-1-{[(2,4-dichlorophenyl)methyl][2-(dimethylamino)ethyl]amino}-2-cyclohexylvinyl)amino]phenyl}-N-[2-(4-methoxyphenyl)ethyl]carboxamide, {4-[((1Z)-2-aza-1-{[2-(dimethylamino)ethyl][(4-chlorophenyl)methyl]amino}-2-cyclohexylvinyl)amino]phenyl}-N-[2-(4-methoxyphenyl)ethyl]carboxamide, {4-[((1Z)-2-aza-1-{[2-(dimethylamino)ethyl][(2-chlorophenyl)methyl]amino}-2-cyclohexylvinyl)amino]phenyl}-N-[2-(4-methoxyphenyl)ethyl]carboxamide, {4-[((1Z)-2-aza-1-{[2-(dimethylamino)ethyl][(3-chlorophenyl)methyl]amino}-2-cyclohexylvinyl)amino]phenyl}-N-[2-(4-methoxyphenyl)ethyl]carboxamide, {4-[((1Z)-2-aza-1-[2-(dimethylamino)ethyl]benzylamino}-2-cyclohexylvinyl)amino]phenyl}-N-methyl-N-(2-phenylethyl)carboxamide, {4-[((1Z)-2-aza-1-{[2-(dimethylamino)ethyl]benzylamino}-2-cyclohexylvinyl)amino]phenyl}-N-[2-(4-methylphenyl)ethyl]carboxamide, {4-[((1Z)-2-aza-1-{[2-(dimethylamino)ethyl]benzylamino}-2-cyclohexylvinyl)amino]phenyl}-N-[2-(4-methoxyphenyl)ethyl]carboxamide, {4-[((1Z)-2-aza-1-{[2-(dimethylamino)ethyl]benzylamino}-2-cyclohexylvinyl)amino]phenyl}-N-[2-(3-methoxyphenyl)ethyl]carboxamide, {4-[((1Z)-2-aza-1-{[2-(dimethylamino)ethyl]benzylamino}-2-cyclohexylvinyl)amino]phenyl}-N-[2-(4-1-hydroxyphenyl)ethyl]carboxamide, {4-[((1Z)-2-aza-1-{[2-(dimethylamino)ethyl]benzylamino}-2-cyclohexylvinyl)amino]phenyl}-N-[2-(4-methoxyphenyl)ethyl]carboxamide, {4-[((1Z)-2-aza-2-cyclohexyl-1-{[(4-fluorophenyl)methyl](2-pyridylmethyl)amino}vinyl)amino]phenyl}-N-(2-phenylethyl)carboxamide, [4-({(1 E)-2-aza-1-[({1-[(4-chlorophenyl)methyl]-5-methylimidazol-4-yl}methyl)amino]-2-cyclohexylvinyl}amino)phenyl]-N-[2-(4-methoxyphenyl)ethyl]carboxamide, {4-[((1Z)-2-aza-1-{[2-(dimethylamino)ethyl][(4-ethylphenyl)methyl]amino}-2-cyclohexylvinyl)amino]phenyl}-N-[2-(2,4-dichlorophenyl)ethyl]carboxamide, {4-[((1E)-2-aza-2-cyclohexyl-1-{[1-benzyl(4-piperidyl)]amino}vinyl)amino]phenyl}-N-[2-(4-methoxyphenyl)ethyl]carboxamide, 3-{4-[((1Z)-2-aza-1-{[2-(dimethylamino)ethyl]benzylamino}-2-cyclohexylvinyl)amino]phenyl}-N-(2-phenylethyl)propanamide, {4-[((1Z)-2-aza-1-{[2-(dimethylamino)ethyl]benzylamino}-2-cyclohexylvinyl)amino]phenyl}-N-[2-(2,4-dichlorophenyl)ethyl]carboxamide, {4-[((1Z)-2-aza-1-{[2-(dimethylamino)ethyl][(3-methylphenyl)methyl]amino}-2-cyclohexylvinyl)amino]phenyl}-N-[2-(4-methoxyphenyl)ethyl]carboxamide, {4-[((1Z)-2-aza-1-{[2-(dimethylamino)ethyl]benzylamino}-2-cyclohexylvinyl)amino]phenyl}-N-[2-(3,4-dimethoxyphenyl)ethyl]carboxamide, {4-[((1Z)-2-aza-1-{[2-(dimethylamino)ethyl]benzylamino}-2-cyclohexylvinyl)amino]phenyl}-N-[2-(2,5-dimethoxyphenyl)ethyl]carboxamide, {4-[((1Z)-2-aza-1-{[2-(dimethylamino)ethyl][(4-methoxyphenyl)methyl]amino}-2-cyclohexylvinyl)amino]phenyl}-N-[2-(4-methoxyphenyl)ethyl]carboxamide, {4-[((1Z)-2-aza-1-{[2-(dimethylamino)ethyl][(3-methoxyphenyl)methyl]amino}-2-cyclohexylvinyl)amino]phenyl}-N-[2-(4-methoxyphenyl)ethyl]carboxamide, {4-[((1Z)-2-aza-1-{[2-(dimethylamino)ethyl][(4-ethylphenyl)methyl]amino}-2-cyclohexylvinyl)amino]phenyl}-N-[2-(4-methoxyphenyl)ethyl]carboxamide, {4-[((1Z)-2-aza-1-{[2-(dimethylamino)ethyl](4-quinolylmethyl)amino}-2-cyclohexylvinyl)amino]phenyl}-N-[2-(4-methoxyphenyl)ethyl]carboxamide, {4-[((1Z)-2-aza-1-{[2-(dimethylamino)ethyl]benzylamino}-2-cy Example 120

In Vivo Studies of MC4-R Agonists on Energy Intake, Body Weight, Hyperinsulinemia, and Glucose Levels In vivo studies were conducted to observe the effect of MCR-4 agonists on energy intake, body weight, hyperinsulinemia, and glucose levels. All studies were conducted with male 9–10 week old ob/ob mice which display early onset of obesity, insulin resistance and diabetes due to leptin deficiency. Mice were acclimated in the facility for 1 week before studies and are caged individually. Vehicle-treated (control) and drug treated mice studies were always run in parallel. In multi-day studies, mice (8–15 per group) were monitored for baseline body weight, fasting levels of glucose, insulin, blood lipids and energy expenditure and then injected twice daily (9 a.m. and 5 p.m.) with 3 mg/kg of the MC4-R agonist 4-[(N-cyclohexyl-3,5-dimethyl-piperazine-1-carboximidoyl)-amino]-N-[2-(2,4-dichlorophenyl)-ethyl]-benzamide for 4 weeks. Body weight as well as food and water intake were monitored daily. Animals were fasted overnight for measurements of fasting levels of glucose, insulin, and lipids once a week until the end of the study. Energy expenditure (resting metabolic rate, i.e., O2 consumption and CO2 production) were monitored in air tight chambers at the end of the study on fed animals. $O_2$ consumption and $CO_2$ production were measured using Oxymax systems (Columbus Instruments). Oral glucose tolerance test (OGTT—a routine test for diabetes and glucose intolerance) was performed on overnight fasted mice at the end of the study. Blood glucose and oral glucose tolerance were measured using a glucose monitor (Onetouch sold by Lifescan). Free fatty acids were measured using an non-esterified free fatty acids enzymatic assay (Waco Chemicals). Serum Insulin levels were measured by immunoassay (Alpco).

Results

The effect of 4-[(N-cyclohexyl-3,5-dimethyl-piperazine-1-carboximidoyl)-amino]-N-[2-(2,4-dichlorophenyl)- ethyl]-benzamide on food intake is shown in FIG. 1. FIG. 1 shows total food intake as represented as grams/mouse/day throughout the 4 week study. Food is monitored every morning. Cumulative food intake represents the total amount of grams the mice consumed during the study. Each group (vehicle or drug) had 15 mice. As shown in FIG. 1, a significant reduction in food intake was demonstrated in those mice treated IP with 4-[(N-cyclohexyl-3,5-dimethyl-piperazine-1-carboximidoyl)-amino]-N-[2-(2,4-dichlorophenyl)-ethyl]-benzamide for 4 weeks.

Figure 2:
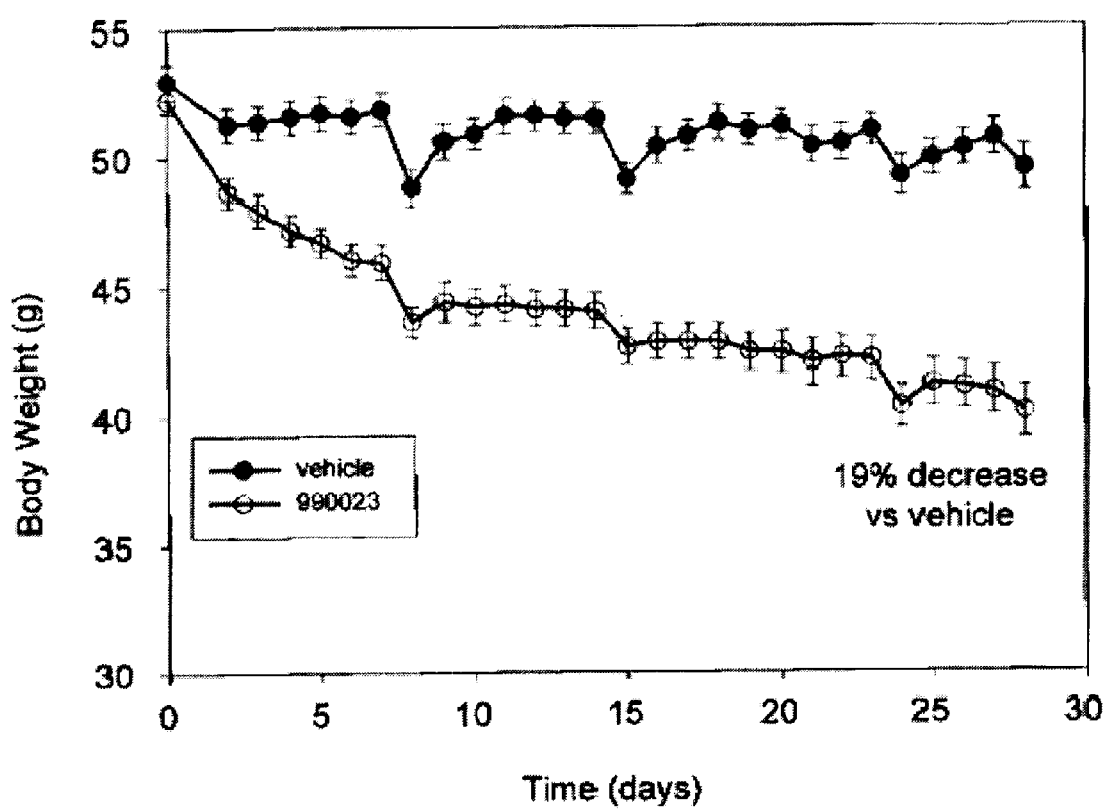
FIG. 2 is a graph showing the reduction in body weight in obese mice treated IP with 4-[(N-cyclohexyl-3,5-dimethyl-piperazine-1-carboximidoyl)-amino]-N-[2-(2,4-dichlorophenyl)-ethyl]-benzamide for 4 weeks.

The effect of 4-[(N-cyclohexyl-3,5-dimethyl-piperazine-1-carboximidoyl)-amino]-N-[2-(2,4-dichlorophenyl)-ethyl]-benzamide on body weight is shown in FIG. 2. FIG. 2 shows body weight reduction as represented as grams/mouse throughout the 4 weeks of the study. Mice were weighed every morning. At the end of the study, drug treated mice weighed 19% less than the vehicle treated mice. Each group (vehicle or drug) had 15 mice. As shown in FIG. 2, significant body weight reduction was demonstrated in those mice treated IP with 4-[(N-cyclohexyl-3,5-d imethyl-piperazine-1-carboximidoyl)-amino]-N-[2-(2,4-dichlorophenyl)-ethyl]-benzamide for 4 weeks.

Figure 3:
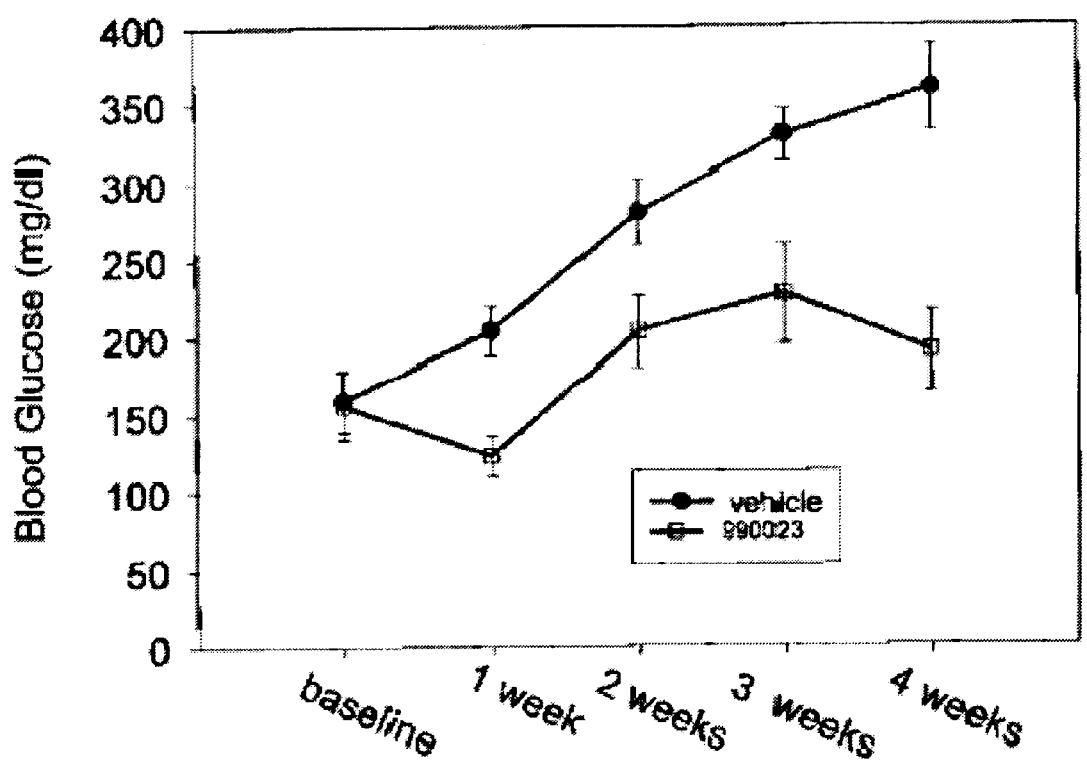
FIG. 3 is a graph showing the reduction in fasting glucose levels in obese mice treated IP with 4-[(N-cyclohexyl-3,5-dimethyl-piperazine-1-carboximidoyl)-amino]-N-[2-(2,4-dichlorophenyl)-ethyl]-benzamide for 4 weeks.

The effect of 4-[(N-cyclohexyl-3,5-dimethyl-piperazine-1-carboximidoyl)-amino]-N-[2-(2,4-dichlorophenyl)-ethyl]-benzamide on blood glucose levels in shown in FIG. 3. FIG. 3 shows blood glucose levels as represented as mg of glucose/di of blood. Mice were fasted overnight and glucose levels were measured at 8 a.m. the following morning. Vehicle treated mice showed an increase in blood glucose consistent with the rapid progression of diabetes in this mouse strain whereas, diabetes was slowed down considerably (47% decrease) in drug treated mice. Each group (vehicle or drug) had 8 mice. As shown in FIG. 3, a significant reduction in fasting glucose levels were demonstrated in those mice treated IP with 4-[(N-cyclohexyl-3,5-dimethyl-piperazine-1-carboximidoyl)-amino]-N-[2-(2,4-dichlorophenyl)-ethyl]-benzamide for 4 weeks.

Figure 4:
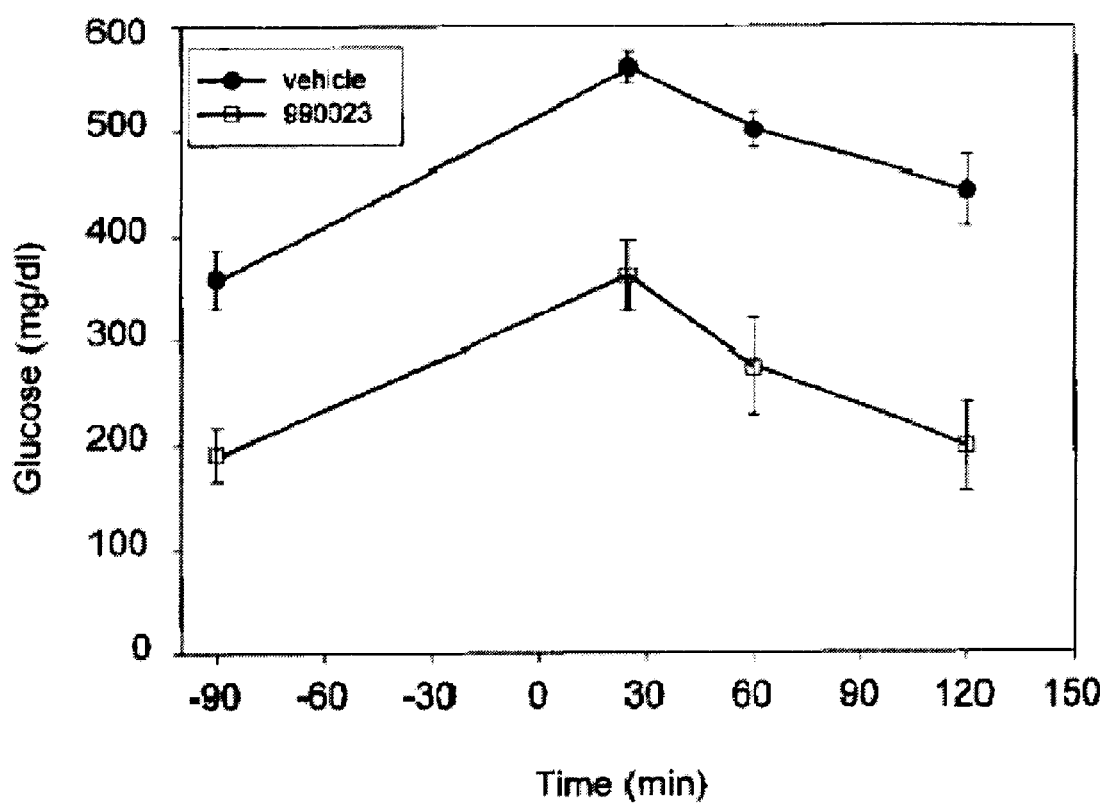
FIG. 4 is a graph showing glucose levels during oral glucose tolerance tests in obese mice treated IP with 4-[(N-cyclohexyl-3,5-dimethyl-piperazine-1-carboximidoyl)-amino]-N-[2-(2,4-dichlorophenyl)-ethyl]-benzamide.

The effect of 4-[(N-cyclohexyl-3,5-dimethyl-piperazine-1-carboximidoyl)-amino]-N-[2-(2,4-dichlorophenyl)-ethyl]-benzamide on glucose levels during oral glucose tolerance test (OGTT) is shown in FIG. 4. FIG. 4 shows OGTT as performed on overnight fasted mice at the end of the study. Blood glucose is represented as mg of glucose/dl of blood. Glucose levels were measured the following morning: 90 minutes before and 25, 60 and 120 minutes after an oral glucose load (2 mg/kg). Orally administered glucose quickly elevated blood glucose, similar to a meal, and the response to this exogenous glucose gave a measure of how well the body regulated glucose horneostasis. As shown in FIG. 4, vehicle treated mice showed an elevated response to glucose consistent with their diabetic state, whereas drug treated mice showed a very much improved glucose disposal, illustrated as a 45% decrease of the area under the curve. Each group (vehicle or drug) had 15 mice.

Figure 5:
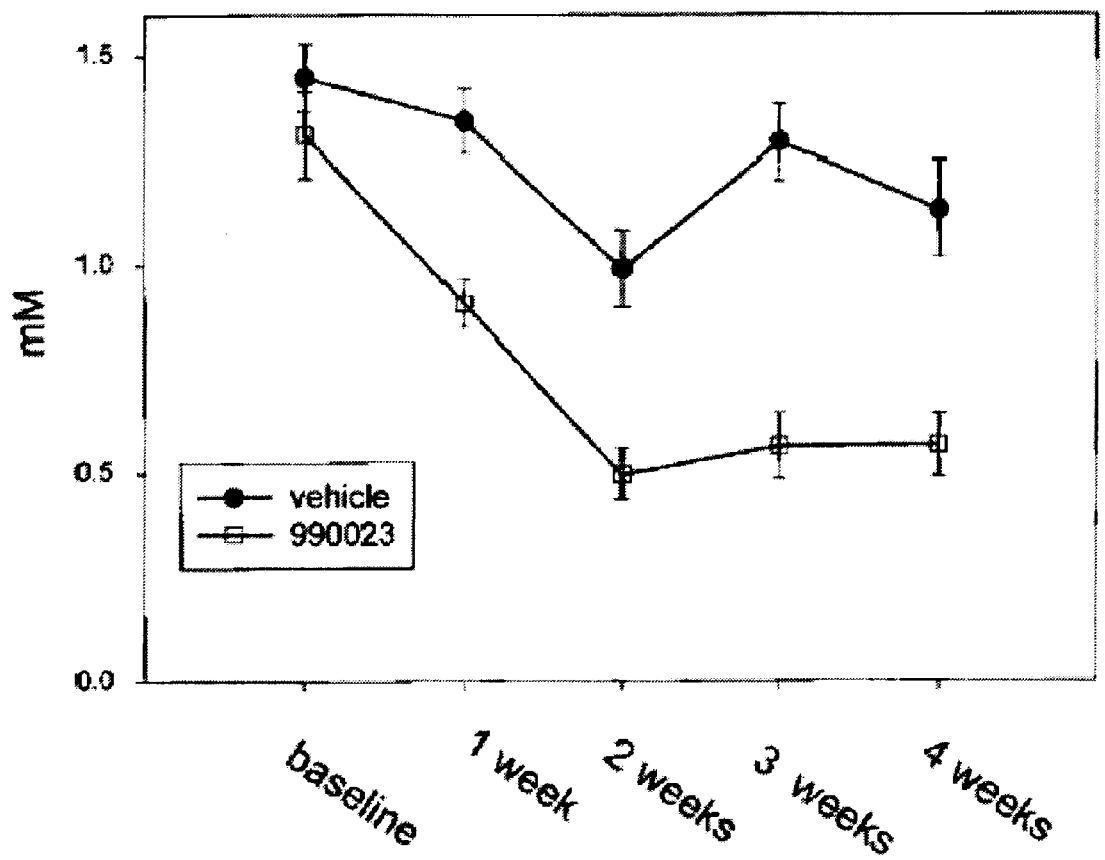
FIG. 5 is a graph showing the reduction in free fatty acid levels in obese mice treated IP with 4-[(N-cyclohexyl-3,5-dimethyl-piperazine-1-carboximidoyl)-amino]-N-[2-(2,4-dichlorophenyl)-ethyl]-benzamide.

The effect of 4-[(N-cyclohexyl-3,5-dimethyl-piperazine-1-carboximidoyl)-amino]-N-[2-(2,4-dichlorophenyl)-ethyl]-benzamide on free fatty acid (FFA) levels is shown in FIG. 5. FIG. 5 shows FFA represented as mmoles of FFA/L of serum. Mice were fasted overnight and free fatty acid levels were measured at 8 a.m. the following morning. As shown in FIG. 5, vehicle treated mice showed elevated levels of FFA throughout the study consistent with their obese state, whereas the drug treated mice diabetes showed a dramatic 50% decrease. Each group (vehicle or drug) had 8 mice.

Figure 6:
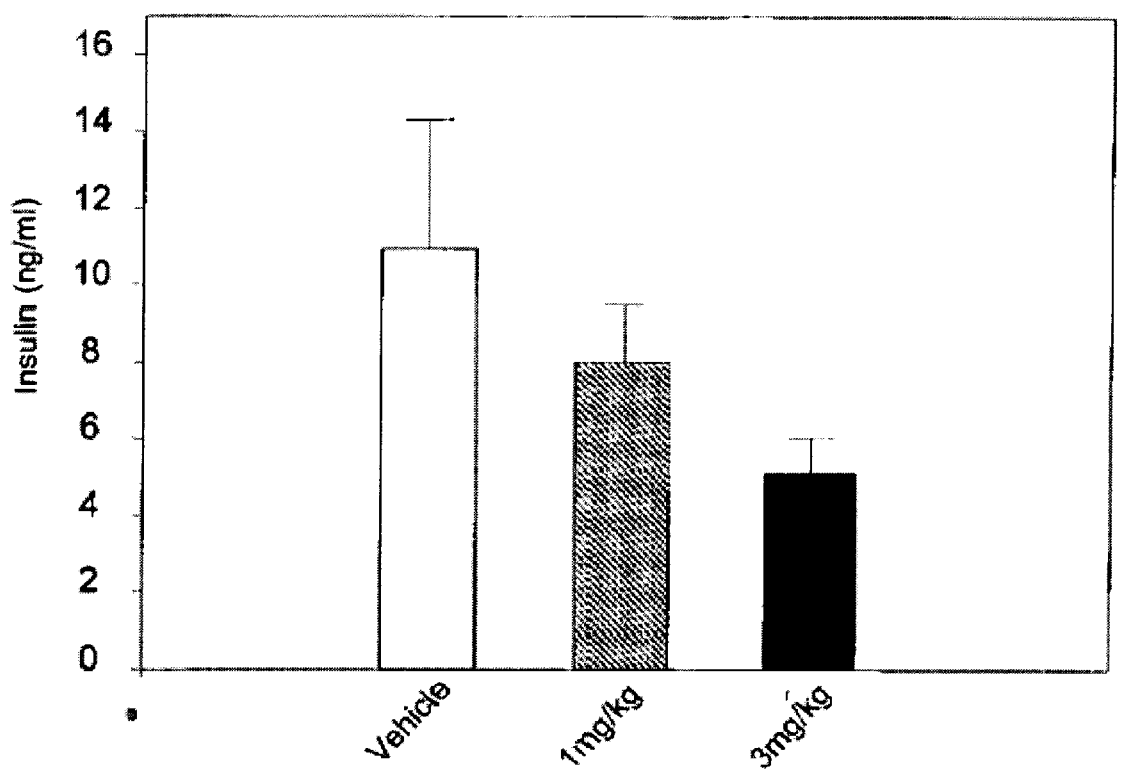
FIG. 6 is a graph showing the acute effect of IP treatment of 4-[(N-cyclohexyl-3,5-dimethyl-piperazine-1-carboximidoyl)-amino]-N-[2-(2,4-dichlorophenyl)-ethyl]-benzamide on insulin levels.

The effect of 4-[(N-cyclohexyl-3,5-dimethyl-piperazine-1-carboximidoyl)-amino]-N-[2-(2,4-dichlorophenyl)-ethyl]-benzamide on serum insulin levels is shown in FIG. 6. Serum insulin levels were measured one hour after single IP dosing of 1 and 3 mg/kg in overnight fasted ob/ob mice. In FIG. 6, serum insulin levels are represented as ng of insulin/ml of serum. As shown in FIG. 6, drug treated mice showed a dose dependent decrease of 27% and 55% respectively relative to vehicle. Each group (vehicle, or drug) had 6 mice.

What is claimed is:

1. A compound of formula IA or IB

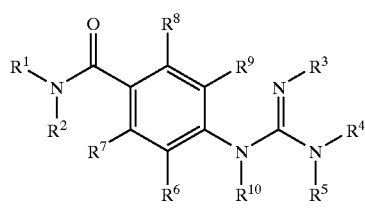

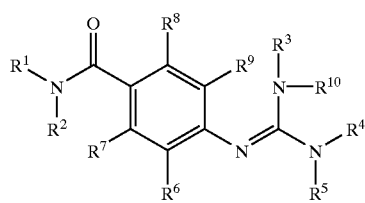

wherein $R^1$ is selected from the group consisting of H, and substituted and unsubstituted arylalkyl, heteroarylalkyl, aryl, heteroaryl, heterocyclyl, cycloalkyl, heterocyclylalkyl, cycloalkylalkyl, alkenyl, alkynyl, and alkyl groups;

$R^2$ is selected from the group consisting of substituted and unsubstituted arylalkyl, alkenyl, heteroarylalkyl, heterocyclylalkyl, cycloalkyl, and cycloalkylalkyl groups;

$R^3$ is selected from the group consisting of substituted and unsubstituted alkyl, alkenyl, alkynyl, cycloalkyl, heteroaryl, heterocyclyl, heterocyclylalkyl, arylalkyl, heteroarylalkyl, and cycloalkylalkyl groups;

$R^4$ is selected from the group consisting of H, and substituted and unsubstituted alkyl, alkenyl, alkynyl, cycloalkyl, aryl, heteroaryl, heterocyclyl, arylalkyl, heteroarylalkyl, and cycloalkylalkyl groups;

$R^5$ is selected from the group consisting of substituted and unsubstituted alkyl, alkenyl, alkynyl, cycloalkyl, aryl, heteroaryl, heterocyclyl, arylalkyl, heteroarylalkyl, and cycloalkylalkyl groups;

or $R^4$ and $R^5$, together with the nitrogen to which they are bound, form a substituted or unsubstituted heterocyclyl or heteroaryl group;

$R^6$, $R^7$, $R^8$, and $R^9$ may be the same or different, and are each independently selected from the group consisting of H, Cl, I, F, Br, OH, $NH_2$, CN, $NO_2$, and substituted and unsubstituted alkoxy, amino, alkyl, alkenyl, alkynyl, alkylamino, dialkylamino, cycloalkyl, heterocyclylamino, heteroarylamino, aminocarbonyl, alkylaminocarbonyl, d lalkylaminocarbonyl, cycloalkylaminocarbonyl, arylaminocarbonyl, heterocyclylaminocarbonyl, and heteroarylaminocarbonyl groups;

$R^{10}$ is selected from the group consisting of H, and substituted and unsubstituted alkyl, alkenyl, alkynyl, cycloalkylalkyl, aryl, and arylalkyl groups; and prodrugs thereof, pharmaceutically acceptable salts thereof, stereoisomers thereof, tautomers thereof, hydrates thereof, hydrides thereof, or solvates thereof.

2. The compound according to claim 1, wherein $R^2$ is selected from the group consisting of substituted and unsubstituted arylalkyl, alkenyl, heteroarylalkyl, and heterocyclylalkyl groups.

3. The compound according to claim 1, wherein $R^3$ is selected from the group consisting of substituted and unsubstituted cycloalkyl, alkenyl, alkyl, and aryl groups.

4. The compound according to claim 1, wherein $R^4$ and $R^5$ may be the same or different and are each independently selected from the group consisting of substituted and unsubstituted alkyl, arylalkyl, and heteroarylalkyl groups.

5. The compound according to claim 1, wherein $R^4$ and $R^5$, together with the nitrogen to which they are bound, form a substituted or unsubstituted heterocyclyl group.

6. The compound according to claim 5, wherein $R^4$ and $R^5$, together with the N atom to which they are bound, form a substituted or unsubstituted saturated heterocyclyl group comprising at least one heteroatom selected from the group consisting of O, S, and N in addition to the N atom to which $R^4$ and $R^5$ are bound.

7. The compound according to claim 1, wherein $R^2$ is selected from the group consisting of substituted and unsubstituted arylalkyl groups.

8. The compound according to claim 1, wherein $R^2$ is a 2,4-disubstituted phenethyl group.

9. The compound according to claim 1, wherein $R^2$ is a 2,4-dihalophenethyl group or a 2,4-dialkylphenethyl group.

10. The compound according to claim 1, wherein $R^2$ is selected from the group consisting of phenethyl, 2,4-dichlorophenethyl, 4-methoxyphenethyl, 4-bromophenethyl, 4-methylphenethyl, 4-chlorophenethyl, 4-chlorobenzyl, 4-ethyiphenethyl, cyclohexenylethyl, 2-methoxyphenethyl, 2-chlorophenethyl, 2-fluorophenethyl, 3-methoxyphenethyl, 3-fluorophenethyl, thienylethyl, indolylethyl, 4-hydroxyphenethyl, 3,4-dimethoxyphenethyl, 2-chloro-4-iodophenethyl, 2-fluoro-4-methylphenethyl, 2-fluoro-4-bromopheflethyl, 2-fluoro-4-methoxyphenethyl, 2-trifluoromethyl-4-fluoropheflethyl, 2,4-difluorophenethyl, 2,4-dimethyiphenethyl, and 2,4-dimethoxyphenethyl groups.

11. The compound according to claim 1, wherein $R^3$ is selected from the group consisting of substituted and unsubstituted cycloalkyl groups, substituted and unsubstituted polycyclic cycloalkyl groups, substituted and unsubstituted alkenyl groups, substituted and unsubstituted alkyl groups, and substituted and unsubstituted aryl groups.

12. The compound according to claim 1, wherein $R^1$ is H.

13. A composition comprising the compound according to claim 1 and a pharmaceutically acceptable carrier.

14. A method of treating an MC4-R mediated disease, comprising administering to a subject in need thereof, the compound according to claim 1, wherein the MC4-R mediated disease is obesity or type II diabetes.

* * * * *

UNITED STATES PATENT AND TRADEMARK OFFICE
CERTIFICATE OF CORRECTION

PATENT NO.    : 6,638,927 B2
DATED         : October 28, 2003
INVENTOR(S)   : Paul A. Renhowe et al.

It is certified that error appears in the above-identified patent and that said Letters Patent is hereby corrected as shown below:

Column 6,
Line 45, delete the "s" on the end of the word "includes" to read -- include --.

Column 7,
Line 55, delete the space in the word "oxad iazole," and replace it with -- oxadiazole --.

Column 8,
Line 23, delete the word "amides" and replace it with -- imides --.
Line 60, delete the "s" on the end of the word "includes" to read -- include --.

Column 23,
Line 61, please delete "WO 00133813" and replace it with -- WO 00/33813 --.

Column 26,
Line 13, delete the space in "DM F" and replace it with -- DMF --.

Column 32,
Line 26, of the title for Example 15, delete the space in "dimethyl but-l-enyl]" and replace it with -- dimethylbut-l-enyl] --.
Line 38, of Example 15, delete the space in "dimethyl but-1-enyl]" and replace it with -- dimethylbut-l-enyl] --.

Column 42,
Line 6, please move "Example 39" down two lines so that it appears on a line of its own before the heading "General Procedure for the Preparation of Polystyrene-Bound P-Benzamido Iminophosphoranes."
Line 36, delete the word "p-benzamdio" and replace it with -- p-benzamido --.

Column 44,
Lines 19-23, please move "(4-{[1-((3S)-3-methylpiperazinyl)..." down two lines so that it appears as an independent entry.

Column 54,
Line 10, delete "OC" and replace it with -- 0C --.

Column 59,
Line 2, delete "(2equivalents)" and replace it with -- (2 equivalents) --.

UNITED STATES PATENT AND TRADEMARK OFFICE
CERTIFICATE OF CORRECTION

PATENT NO. : 6,638,927 B2
DATED : October 28, 2003
INVENTOR(S) : Paul A. Renhowe et al.

It is certified that error appears in the above-identified patent and that said Letters Patent is hereby corrected as shown below:

Column 61,
Line 39, delete "Step 30" and replace it with -- Step 3 --.

Column 62,
Line 20, add a -- d -- to the end of "reduce" to read -- reduced --.

Column 63,
Line 17, delete the space in "...-tetrahydro-1 H-benzo[d]azepine" and replace it with -- ...-tetrahydro-lH-benzol[d]azepine --.

Column 64,
Line 2, of Example 70 in the Table of Examples 61-113, delete "[1,1,7-" and replace it with -- [1,7,7,- --.

Column 68,
Line 44, of Example 119, delete the double dash between "2--aza" and replace it with -- 2-aza --.

Column 72,
Line 1, delete the space between "dimethyl piperazinyl)" to read
-- dimethylpiperazinyl) --.

Column 73,
Line 55, delete "[2-(4-1-hydroxyphenyl)ethyl]" and replace it with
-- [2-(4-hydroxyphenyl)ethyl] --.

Column 74,
Line 27, delete "cy" and add the missing text to read -- cyclohexylvinyl)amino]phenyl}-N-(2,2-diphenylethyl)carboxamide, {4-[((1Z)-2-aza-1-{[2-(dimethylamino)ethyl]benzylamino}-2-cyclohexylvinyl)amino]phenyl}-N-(2,2-diphenylethyl)carboxamide, {4-[((1Z)-2-aza-1-{[2-(dimethylamino)ethyl]benzylamino}-2-cyclohexylvinyl)amino]phenyl}-N-(2-phenylethyl)-N-benzylcarboxamide, and (acetyloxy)methyl (2S)-4-((E)-{[4-({[2-(2,4-dichlorophenyl)ethyl]amino}carbonyl)phenyl]amino} {[(1S,2S,3S,5R)-2,6,6-trimethylbicyclo[3.1.1]hept-3-yl]imino}methyl)-2-methylpiperazine-1 -carboxylate. --.

UNITED STATES PATENT AND TRADEMARK OFFICE
CERTIFICATE OF CORRECTION

PATENT NO. : 6,638,927 B2
DATED : October 28, 2003
INVENTOR(S) : Paul A. Renhowe et al.

It is certified that error appears in the above-identified patent and that said Letters Patent is hereby corrected as shown below:

Column 75,
Line 20, delete the space between "d imethyl" and replace it with -- dimethyl --.
Line 27, delete "glucose/di" and replace it with -- glucose/dl --.
Line 25, delete the words "levels in shown" and replace them with -- levels is shown --.
Line 49, delete the word "horneostasis" and replace it with -- homeostasis --.

Column 76,
Line 61, delete "d lalkylaminocarbonyl," and replace it with -- dialkylaminocarbonyl --.

Column 78,
Line 5, delete "4-ethyiphenethyl," and replace it with -- 4-ethylphenethyl, --.
Line 10, delete "bromopheflethyl," and replace it with -- bromophenethyl, --.
Line 11, delete "fluoropheflethyl" and replace it with -- fluorophenethyl --.
Line 12, delete "dimethyiphenethyl," and replace it with -- uimethylphenethyl, --.

Signed and Sealed this

Fourteenth Day of June, 2005

JON W. DUDAS
*Director of the United States Patent and Trademark Office*

UNITED STATES PATENT AND TRADEMARK OFFICE
CERTIFICATE OF CORRECTION

PATENT NO.    : 6,638,927 B2
DATED         : October 28, 2003
INVENTOR(S)   : Paul A. Renhowe et al.

It is certified that error appears in the above-identified patent and that said Letters Patent is hereby corrected as shown below:

Column 6,
Line 45, delete the "s" on the end of the word "includes" to read -- include --.

Column 7,
Line 55, delete the space in the word "oxad iazole," and replace it with -- oxadiazole --.

Column 8,
Line 23, delete the word "amides" and replace it with -- imides --.
Line 60, delete the "s" on the end of the word "includes" to read -- include --.

Column 23,
Line 61, please delete "WO 00133813" and replace it with -- WO 00/33813 --.

Column 26,
Line 13, delete the space in "DM F" and replace it with -- DMF --.

Column 32,
Line 26, of the title for Example 15, delete the space in "dimethyl but-l-enyl]" and replace it with -- dimethylbut-l-enyl] --.
Line 38, of Example 15, delete the space in "dimethyl but-1-enyl]" and replace it with -- dimethylbut-l-enyl] --.

Column 42,
Line 6, please move "Example 39" down two lines so that it appears on a line of its own before the heading "General Procedure for the Preparation of Polystyrene-Bound P-Benzamido Iminophosphoranes."
Line 36, delete the word "p-benzamdio" and replace it with -- p-benzamido --.

Column 44,
Lines 19-23, please move "(4-{[1-((3S)-3-methylpiperazinyl)..." down two lines so that it appears as an independent entry.

Column 54,
Line 10, delete "OC" and replace it with -- 0C --.

Column 59,
Line 2, delete "(2equivalents)" and replace it with -- (2 equivalents) --.

UNITED STATES PATENT AND TRADEMARK OFFICE
CERTIFICATE OF CORRECTION

PATENT NO. : 6,638,927 B2
DATED : October 28, 2003
INVENTOR(S) : Paul A. Renhowe et al.

It is certified that error appears in the above-identified patent and that said Letters Patent is hereby corrected as shown below:

Column 61,
Line 39, delete "Step 30" and replace it with -- Step 3 --.

Column 62,
Line 20, add a -- d -- to the end of "reduce" to read -- reduced --.

Column 63,
Line 17, delete the space in "...-tetrahydro-1 H-benzo[d]azepine" and replace it with -- ...-tetrahydro-lH-benzol[d]azepine --.

Column 64,
Line 2, of Example 70 in the Table of Examples 61-113, delete "[1,1,7-" and replace it with -- [1,7,7,- --.

Column 68,
Line 44, of Example 119, delete the double dash between "2--aza" and replace it with -- 2-aza --.

Column 72,
Line 1, delete the space between "dimethyl piperazinyl)" to read
-- dimethylpiperazinyl) --.

Column 73,
Line 55, delete "[2-(4-1-hydroxyphenyl)ethyl]" and replace it with
-- [2-(4-hydroxyphenyl)ethyl] --.

Column 74,
Line 27, delete "cy" and add the missing text to read -- cyclohexylvinyl)amino]phenyl}-N-(2,2-diphenylethyl)carboxamide, {4-[((1Z)-2-aza-1-{[2-(dimethylamino)ethyl]benzylamino}-2-cyclohexylvinyl)amino]phenyl}-N-(2,2-diphenylethyl)carboxamide, {4-[((1Z)-2-aza-1-{[2-(dimethylamino)ethyl]benzylamino}-2-cyclohexylvinyl)amino]phenyl}-N-(2-phenylethyl)-N-benzylcarboxamide, and (acetyloxy)methyl (2S)-4-((E)-{[4-({[2-(2,4-dichlorophenyl)ethyl]amino}carbonyl)phenyl]amino} {[(1S,2S,3S,5R)-2,6,6-trimethylbicyclo[3.1.1]hept-3-yl]imino}methyl)-2-methylpiperazine-1 -carboxylate. --.

UNITED STATES PATENT AND TRADEMARK OFFICE
CERTIFICATE OF CORRECTION

PATENT NO. : 6,638,927 B2
DATED : October 28, 2003
INVENTOR(S) : Paul A. Renhowe et al.

It is certified that error appears in the above-identified patent and that said Letters Patent is hereby corrected as shown below:

Column 75,
Line 20, delete the space between "d imethyl" and replace it with -- dimethyl --.
Line 27, delete "glucose/di" and replace it with -- glucose/dl --.
Line 25, delete the words "levels in shown" and replace them with -- levels is shown --.
Line 49, delete the word "horneostasis" and replace it with -- homeostasis --.

Column 76,
Line 61, delete "d lalkylaminocarbonyl," and replace it with -- dialkylaminocarbonyl --.

Column 78,
Line 5, delete "4-ethyiphenethyl," and replace it with -- 4-ethylphenethyl, --.
Line 10, delete "bromopheflethyl," and replace it with -- bromophenethyl, --.
Line 11, delete "fluoropheflethyl" and replace it with -- fluorophenethyl --.
Line 12, delete "dimethyiphenethyl," and replace it with -- dimethylphenethyl, --.

This certificate supersedes Certificate of Correction issued June 14, 2005.

Signed and Sealed this

Sixth Day of September, 2005

JON W. DUDAS
*Director of the United States Patent and Trademark Office*